US012672781B2

(12) United States Patent
Fengler et al.

(10) Patent No.: US 12,672,781 B2
(45) Date of Patent: Jul. 7, 2026

(54) SYSTEMS AND METHODS FOR IMAGING USING A CONFIGURABLE PLATFORM

(71) Applicant: Stryker Corporation, Kalamazoo, MI (US)

(72) Inventors: John Josef Paul Fengler, North Vancouver (CA); Robert Anthony Stead, North Vancouver (CA)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/662,484

(22) Filed: May 13, 2024

(65) Prior Publication Data

US 2024/0366089 A1    Nov. 7, 2024

Related U.S. Application Data

(63) Continuation of application No. 17/658,815, filed on Apr. 11, 2022, now Pat. No. 11,980,441, which is a
(Continued)

(51) Int. Cl.
   *A61B 5/00*        (2006.01)
   *A61B 1/00*        (2006.01)
   (Continued)

(52) U.S. Cl.
   CPC ........ *A61B 5/0071* (2013.01); *A61B 1/00186* (2013.01); *A61B 1/043* (2013.01);
   (Continued)

(58) Field of Classification Search
   CPC ... A61B 5/0071; A61B 1/00186; A61B 1/043; A61B 1/051; A61B 1/0638;
   (Continued)

(56) References Cited

U.S. PATENT DOCUMENTS 1,290,744 A    1/1919   Hollander
2,453,336 A    11/1948  Orser
          (Continued)

FOREIGN PATENT DOCUMENTS

CN      2076516 U      5/1991
CN    101242789 A      8/2008
          (Continued)

OTHER PUBLICATIONS

US 6,692,429 B1, 02/2004, Imaizumi et al. (withdrawn)
          (Continued)

*Primary Examiner* — Boubacar Abdou Tchoussou
(74) *Attorney, Agent, or Firm* — Morrison & Foerster LLP

(57)          ABSTRACT

Provided herein are systems for fluorescence imaging of an object and methods of use thereof, the systems comprising: an image sensor assembly comprising at least one image sensor; and an optical assembly configured to transmit light emitted from the object to the image sensor assembly, the optical assembly comprising at least one notch filter configured to block light in a plurality of fluorescence excitation wavebands while transmitting fluorescence light that is emitted from the object, wherein the optical assembly is configured to project the emitted fluorescence light as one or more fluorescence images onto the at least one image sensor of the image sensor assembly.

31 Claims, 24 Drawing Sheets

Related U.S. Application Data continuation of application No. 17/234,461, filed on Apr. 19, 2021, now Pat. No. 11,298,024, which is a continuation of application No. 15/416,876, filed on Jan. 26, 2017, now Pat. No. 10,980,420.

(60) Provisional application No. 62/354,611, filed on Jun. 24, 2016, provisional application No. 62/287,415, filed on Jan. 26, 2016.

(51) Int. Cl.

| | |
|---|---|
| *A61B 1/04* | (2006.01) |
| *A61B 1/05* | (2006.01) |
| *A61B 1/06* | (2006.01) |
| *G01J 1/00* | (2006.01) |
| *G01J 1/58* | (2006.01) |
| *G01J 3/02* | (2006.01) |
| *G01J 3/10* | (2006.01) |
| *G01J 3/36* | (2006.01) |
| *G01J 3/44* | (2006.01) |
| *G02B 21/16* | (2006.01) |
| *G02B 27/10* | (2006.01) |
| *H04N 23/11* | (2023.01) |
| *H04N 23/16* | (2023.01) |
| *H04N 23/56* | (2023.01) |
| *H04N 23/60* | (2023.01) |
| *H04N 23/667* | (2023.01) |
| *H04N 23/74* | (2023.01) |
| *H04N 23/75* | (2023.01) |
| *H04N 25/11* | (2023.01) |
| *H04N 13/204* | (2018.01) |

(52) U.S. Cl.
CPC ............ *A61B 1/051* (2013.01); *A61B 1/0638* (2013.01); *A61B 1/0684* (2013.01); *G01J 1/00* (2013.01); *G01J 1/58* (2013.01); *G01J 3/0205* (2013.01); *G01J 3/0208* (2013.01); *G01J 3/021* (2013.01); *G01J 3/0248* (2013.01); *G01J 3/10* (2013.01); *G01J 3/36* (2013.01); *G01J 3/4406* (2013.01); *G02B 21/16* (2013.01); *G02B 27/1013* (2013.01); *G02B 27/106* (2013.01); *H04N 23/11* (2023.01); *H04N 23/16* (2023.01); *H04N 23/56* (2023.01); *H04N 23/60* (2023.01); *H04N 23/667* (2023.01); *H04N 23/74* (2023.01); *H04N 23/75* (2023.01); *H04N 25/11* (2023.01); *A61B 5/0035* (2013.01); *A61B 5/0084* (2013.01); *H04N 13/204* (2018.05); *H04N 2209/049* (2013.01)

(58) Field of Classification Search
CPC ... A61B 1/0684; A61B 5/0035; A61B 5/0084; G01J 1/00; G01J 1/58; G01J 3/0205; G01J 3/0208; G01J 3/021; G01J 3/0248; G01J 3/10; G01J 3/36; G01J 3/4406; G02B 21/16; G02B 27/1013; G02B 27/106; H04N 23/11; H04N 23/16; H04N 23/56; H04N 23/60; H04N 23/667; H04N 23/74; H04N 23/75; H04N 25/11; H04N 13/204; H04N 2209/049
See application file for complete search history.

(56) References Cited

U.S. PATENT DOCUMENTS

| | | |
|---|---|---|
| 2,857,523 A | 10/1958 | Corso |
| 3,215,029 A | 11/1965 | Woodcock |
| 3,582,178 A | 6/1971 | Boughton et al. |
| 3,671,098 A | 6/1972 | Rotter |
| 3,749,494 A | 7/1973 | Hodges |
| 3,762,801 A | 10/1973 | Baker |
| 3,790,248 A | 2/1974 | Kellow |
| 3,931,593 A | 1/1976 | Marshall |
| 3,970,373 A | 7/1976 | Pledger |
| 3,971,068 A | 7/1976 | Gerhardt et al. |
| 4,037,866 A | 7/1977 | Price |
| 4,066,330 A | 1/1978 | Jones |
| 4,115,812 A | 9/1978 | Akatsu |
| 4,149,190 A | 4/1979 | Wessler et al. |
| 4,158,504 A | 6/1979 | de Ponteves et al. |
| 4,200,801 A | 4/1980 | Schuresko |
| 4,260,217 A | 4/1981 | Traeger et al. |
| 4,318,395 A | 3/1982 | Tawara |
| 4,355,325 A | 10/1982 | Nakamura et al. |
| 4,378,571 A | 3/1983 | Handy |
| 4,449,535 A | 5/1984 | Renault |
| 4,471,766 A | 9/1984 | Terayama |
| 4,532,918 A | 8/1985 | Wheeler |
| 4,556,057 A | 12/1985 | Hiruma et al. |
| 4,575,632 A | 3/1986 | Lange |
| 4,597,630 A | 7/1986 | Brandstetter et al. |
| 4,611,888 A | 9/1986 | Prenovitz et al. |
| 4,638,365 A | 1/1987 | Kato |
| 4,656,508 A | 4/1987 | Yokota |
| 4,660,982 A | 4/1987 | Okada |
| 4,688,905 A | 8/1987 | Okamura |
| 4,717,952 A | 1/1988 | Kohayakawa et al. |
| 4,742,388 A | 5/1988 | Cooper et al. |
| 4,768,513 A | 9/1988 | Suzuki |
| 4,786,813 A | 11/1988 | Svanberg et al. |
| 4,799,104 A | 1/1989 | Hosoya et al. |
| 4,806,005 A | 2/1989 | Schneider et al. |
| 4,821,117 A | 4/1989 | Sekiguchi |
| 4,837,625 A | 6/1989 | Douziech et al. |
| 4,852,985 A | 8/1989 | Fujihara et al. |
| 4,856,495 A | 8/1989 | Tohjoh et al. |
| 4,885,634 A | 12/1989 | Yabe |
| 4,895,145 A | 1/1990 | Joffe et al. |
| 4,930,516 A | 6/1990 | Alfano et al. |
| 4,930,883 A | 6/1990 | Salzman |
| 4,951,135 A | 8/1990 | Sasagawa et al. |
| 4,953,539 A | 9/1990 | Nakamura et al. |
| 4,954,897 A | 9/1990 | Ejima et al. |
| 4,974,936 A | 12/1990 | Ams et al. |
| 5,001,556 A | 3/1991 | Nakamura et al. |
| 5,007,408 A | 4/1991 | Ieoka |
| 5,028,128 A | 7/1991 | Onuki |
| 5,034,888 A | 7/1991 | Uehara et al. |
| 5,041,852 A | 8/1991 | Misawa et al. |
| 5,115,308 A | 5/1992 | Onuki |
| 5,121,220 A | 6/1992 | Nakamoto |
| 5,128,803 A | 7/1992 | Sprafke |
| 5,132,837 A | 7/1992 | Kitajima |
| 5,134,662 A | 7/1992 | Bacus et al. |
| 5,159,398 A | 10/1992 | Maekewa et al. |
| 5,165,079 A | 11/1992 | Schulz-Hennig |
| 5,205,280 A | 4/1993 | Dennison, Jr. et al. |
| 5,208,651 A | 5/1993 | Buican |
| 5,212,593 A | 5/1993 | Williamson et al. |
| 5,214,503 A | 5/1993 | Chiu et al. |
| 5,225,883 A | 7/1993 | Carter et al. |
| 5,255,087 A | 10/1993 | Nakamura et al. |
| 5,278,642 A | 1/1994 | Danna et al. |
| 5,282,082 A | 1/1994 | Espie et al. |
| 5,295,017 A | 3/1994 | Brown |
| RE34,622 E | 5/1994 | Ledley |
| 5,365,057 A | 11/1994 | Morley et al. |
| 5,371,355 A | 12/1994 | Wodecki |
| 5,377,686 A | 1/1995 | O'Rourke et al. |
| 5,379,756 A | 1/1995 | Pileski et al. |
| 5,408,263 A | 4/1995 | Kikuchi et al. |
| 5,410,363 A | 4/1995 | Capen et al. |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,424,841 A | 6/1995 | Van Gelder et al. |

(56) References Cited

U.S. PATENT DOCUMENTS

| | | |
|---|---|---|
| 5,426,530 A | 6/1995 | Copenhaver et al. |
| 5,430,476 A | 7/1995 | Häfele et al. |
| D362,435 S | 9/1995 | Charych |
| 5,467,223 A | 11/1995 | Cleveland, Jr. et al. |
| 5,481,401 A | 1/1996 | Kita et al. |
| 5,485,203 A | 1/1996 | Nakamura et al. |
| 5,490,015 A | 2/1996 | Umeyama et al. |
| 5,507,287 A | 4/1996 | Palcic et al. |
| 5,515,449 A | 5/1996 | Tsuruoka et al. |
| 5,535,052 A | 7/1996 | Jörgens |
| 5,536,236 A | 7/1996 | Yabe et al. |
| 5,557,451 A | 9/1996 | Copenhaver et al. |
| 5,582,168 A | 12/1996 | Samuels et al. |
| 5,585,846 A | 12/1996 | Kim |
| 5,590,660 A | 1/1997 | MacAulay et al. |
| 5,591,119 A | 1/1997 | Adair |
| 5,596,654 A | 1/1997 | Tanaka |
| 5,630,782 A | 5/1997 | Adair |
| 5,646,680 A | 7/1997 | Yajima |
| 5,647,368 A | 7/1997 | Zeng et al. |
| 5,647,840 A | 7/1997 | D'Amelio et al. |
| 5,667,472 A | 9/1997 | Finn et al. |
| 5,677,724 A | 10/1997 | Takizawa et al. |
| 5,682,567 A | 10/1997 | Spruck et al. |
| 5,689,354 A | 11/1997 | Orino |
| 5,695,049 A | 12/1997 | Bauman |
| 5,697,373 A | 12/1997 | Richards-Kortum et al. |
| 5,713,364 A | 2/1998 | DeBaryshe et al. |
| 5,729,382 A | 3/1998 | Morita et al. |
| 5,749,830 A | 5/1998 | Kaneko et al. |
| 5,769,792 A | 6/1998 | Palcic et al. |
| 5,772,355 A | 6/1998 | Ross et al. |
| 5,772,580 A | 6/1998 | Utsui et al. |
| 5,803,905 A | 9/1998 | Allred et al. |
| 5,827,190 A | 10/1998 | Palcic et al. |
| 5,833,617 A | 11/1998 | Hayashi |
| 5,838,001 A | 11/1998 | Minakuchi et al. |
| 5,840,017 A | 11/1998 | Furuswaba et al. |
| 5,852,498 A | 12/1998 | Youvan et al. |
| 5,879,621 A | 3/1999 | Faries, Jr. et al. |
| 5,891,016 A | 4/1999 | Utsui et al. |
| 5,897,269 A | 4/1999 | Ross et al. |
| 5,971,918 A | 10/1999 | Zanger |
| 5,973,315 A | 10/1999 | Saldana et al. |
| 5,984,861 A | 11/1999 | Crowley |
| 5,986,271 A | 11/1999 | Lazarev et al. |
| 5,986,642 A | 11/1999 | Ueda et al. |
| 5,990,996 A | 11/1999 | Sharp |
| 5,999,240 A | 12/1999 | Sharp et al. |
| 6,002,137 A | 12/1999 | Hayashi |
| 6,004,263 A | 12/1999 | Nakaichi et al. |
| 6,008,889 A | 12/1999 | Zeng et al. |
| 6,021,344 A | 2/2000 | Lui et al. |
| 6,028,323 A | 2/2000 | Liu |
| 6,028,622 A | 2/2000 | Suzuki |
| 6,030,339 A | 2/2000 | Tatsuno et al. |
| 6,059,719 A | 5/2000 | Yamamoto et al. |
| 6,059,720 A | 5/2000 | Furusawa et al. |
| 6,061,591 A | 5/2000 | Freitag et al. |
| 6,069,689 A | 5/2000 | Zeng et al. |
| 6,070,096 A | 5/2000 | Hayashi |
| 6,095,982 A | 8/2000 | Richards-Kortum et al. |
| 6,099,466 A | 8/2000 | Sano et al. |
| 6,110,106 A | 8/2000 | MacKinnon et al. |
| 6,120,435 A | 9/2000 | Eino |
| 6,147,705 A | 11/2000 | Krauter et al. |
| 6,148,227 A | 11/2000 | Wagnières et al. |
| 6,161,035 A | 12/2000 | Furusawa |
| 6,181,414 B1 | 1/2001 | Raz et al. |
| 6,192,267 B1 | 2/2001 | Scherninski et al. |
| 6,212,425 B1 | 4/2001 | Irion et al. |
| 6,226,126 B1 | 5/2001 | Conemac |
| 6,258,576 B1 | 7/2001 | Richards-Kortum et al. |
| D446,524 S | 8/2001 | Bontly et al. |
| 6,280,378 B1 | 8/2001 | Kazuhiro et al. |
| 6,293,911 B1 | 9/2001 | Imaizumi et al. |
| 6,315,712 B1 | 11/2001 | Rovegno |
| 6,332,092 B1 | 12/2001 | Deckert et al. |
| 6,364,829 B1 | 4/2002 | Fulghum |
| 6,364,831 B1 | 4/2002 | Crowley |
| 6,377,842 B1 | 4/2002 | Pogue et al. |
| D456,809 S | 5/2002 | Schieffers |
| 6,419,628 B1 | 7/2002 | Rudischhauser et al. |
| 6,422,994 B1 | 7/2002 | Kaneko et al. |
| 6,462,770 B1 | 10/2002 | Cline et al. |
| 6,510,338 B1 | 1/2003 | Irion et al. |
| 6,526,213 B1 | 2/2003 | Ilenda et al. |
| 6,529,239 B1 | 3/2003 | Dyck et al. |
| 6,529,768 B1 | 3/2003 | Hakamata |
| 6,537,211 B1 | 3/2003 | Wang et al. |
| 6,544,102 B2 | 4/2003 | Schäfer et al. |
| 6,571,119 B2 | 5/2003 | Hayashi |
| 6,596,996 B1 | 7/2003 | Stone et al. |
| 6,603,552 B1 | 8/2003 | Cline et al. |
| 6,639,664 B2 | 10/2003 | Haan et al. |
| 6,652,452 B1 | 11/2003 | Seifert et al. |
| D483,668 S | 12/2003 | Le Roux |
| 6,750,971 B2 | 6/2004 | Overbeck et al. |
| 6,772,003 B2 | 8/2004 | Kaneko et al. |
| 6,773,392 B2 | 8/2004 | Kikuchi et al. |
| 6,786,865 B2 | 9/2004 | Dhindsa |
| 6,821,245 B2 | 11/2004 | Cline et al. |
| 6,826,424 B1 | 11/2004 | Zeng et al. |
| 6,898,458 B2 | 5/2005 | Zeng et al. |
| 6,899,675 B2 | 5/2005 | Cline et al. |
| 6,922,583 B1 | 7/2005 | Perelman et al. |
| 6,958,862 B1 | 10/2005 | Joseph |
| 6,960,165 B2 | 11/2005 | Ueno et al. |
| 7,043,291 B2 | 5/2006 | Sendai |
| D524,985 S | 7/2006 | Lukan et al. |
| D524,987 S | 7/2006 | Lukan et al. |
| 7,123,416 B1* | 10/2006 | Erdogan ............... C23C 14/547 |
| | | 359/580 |
| 7,150,552 B2 | 12/2006 | Weidel |
| 7,179,222 B2 | 2/2007 | Imaizumi et al. |
| 7,235,045 B2 | 6/2007 | Wang et al. |
| 7,236,815 B2 | 6/2007 | Richards-Kortum et al. |
| 7,253,894 B2 | 8/2007 | Zeng et al. |
| 7,268,878 B2 | 9/2007 | Wolf et al. |
| 7,324,674 B2 | 1/2008 | Ozawa et al. |
| 7,333,270 B1 | 2/2008 | Pochapsky et al. |
| 7,341,557 B2 | 3/2008 | Cline et al. |
| 7,385,772 B2 | 6/2008 | Forkey et al. |
| 7,420,151 B2 | 9/2008 | Fengler et al. |
| 7,479,990 B2 | 1/2009 | Imaizumi et al. |
| D599,799 S | 9/2009 | Di Bari et al. |
| D603,408 S | 11/2009 | Fitch |
| D606,544 S | 12/2009 | Di Bari et al. |
| 7,697,975 B2 | 4/2010 | Zeng |
| 7,704,206 B2 | 4/2010 | Suzuki et al. |
| 7,722,534 B2 | 5/2010 | Cline et al. |
| 7,777,191 B2 | 8/2010 | Olcott et al. |
| 7,798,955 B2 | 9/2010 | Ishihara et al. |
| 7,811,229 B2 | 10/2010 | Sugimoto |
| 7,928,352 B2 | 4/2011 | Toda |
| 8,035,067 B2 | 10/2011 | Toda |
| 8,068,899 B2 | 11/2011 | Llewellyn et al. |
| D653,811 S | 2/2012 | BenZion |
| 8,140,147 B2 | 3/2012 | Maynard et al. |
| 8,285,015 B2 | 10/2012 | Demos |
| 8,294,757 B2 | 10/2012 | Yu et al. |
| 8,294,977 B2 | 10/2012 | Kirby et al. |
| 8,337,400 B2 | 12/2012 | Mizuyoshi |
| 8,361,775 B2 | 1/2013 | Flower |
| D677,258 S | 3/2013 | Mistkawi |
| 8,408,269 B2 | 4/2013 | Fengler et al. |
| 8,408,772 B2 | 4/2013 | Li |
| D682,277 S | 5/2013 | Tasselli et al. |
| 8,448,867 B2 | 5/2013 | Liu et al. |
| 8,473,035 B2 | 6/2013 | Frangioni |
| 8,498,695 B2 | 7/2013 | Westwick et al. |
| D692,004 S | 10/2013 | Man |
| D692,576 S | 10/2013 | Steinman et al. |
| D692,892 S | 11/2013 | Mistkawi |

(56) References Cited

U.S. PATENT DOCUMENTS

| | | | |
|---|---|---|---|
| D693,802 S | 11/2013 | Wikel | |
| 8,630,698 B2 | 1/2014 | Ueno et al. | |
| 8,721,532 B2 | 5/2014 | Takei et al. | |
| 8,736,748 B2 | 5/2014 | Takita | |
| 8,759,243 B2 | 6/2014 | Coffy et al. | |
| 8,773,756 B2 | 7/2014 | Tesar et al. | |
| 8,788,021 B1 | 7/2014 | Flusberg et al. | |
| 8,790,253 B2 | 7/2014 | Sunagawa et al. | |
| 8,796,699 B2 | 8/2014 | So et al. | |
| 8,830,339 B2 | 9/2014 | Velarde et al. | |
| 8,849,380 B2 | 9/2014 | Patwardhan | |
| D719,574 S | 12/2014 | Alegiani et al. | |
| 8,961,403 B2 | 2/2015 | Cline et al. | |
| D723,563 S | 3/2015 | Alegiani | |
| 8,977,331 B2 * | 3/2015 | Kim | A61B 5/4893 |
| | | | 382/128 |
| 8,979,301 B2 | 3/2015 | Moore | |
| D726,186 S | 4/2015 | Jenkins et al. | |
| 9,054,262 B2 | 6/2015 | Lewis et al. | |
| D734,339 S | 7/2015 | Zhou et al. | |
| 9,082,922 B2 | 7/2015 | Ban et al. | |
| 9,125,552 B2 | 9/2015 | Dunki-Jacobs et al. | |
| 9,143,746 B2 | 9/2015 | Westwick et al. | |
| D742,509 S | 11/2015 | Anderson | |
| 9,173,554 B2 | 11/2015 | Fengler et al. | |
| D749,598 S | 2/2016 | Ray et al. | |
| 9,282,305 B2 | 3/2016 | Kikuchi | |
| 9,294,691 B2 | 3/2016 | Ooki | |
| 9,295,392 B2 | 3/2016 | Douplik et al. | |
| 9,354,370 B1 * | 5/2016 | Erdogan | G02B 5/285 |
| 9,357,931 B2 | 6/2016 | Nahm et al. | |
| 9,386,909 B2 | 7/2016 | Fengler et al. | |
| D764,565 S | 8/2016 | Tekunoff et al. | |
| 9,407,838 B2 | 8/2016 | Butte et al. | |
| 9,435,496 B2 | 9/2016 | Moore | |
| 9,472,597 B2 | 10/2016 | Mohseni | |
| 9,577,012 B2 | 2/2017 | Ooki | |
| D782,901 S | 4/2017 | Richter | |
| 9,642,532 B2 | 5/2017 | Fengler et al. | |
| D791,137 S | 7/2017 | Wang et al. | |
| 9,814,378 B2 | 11/2017 | Moore | |
| D815,928 S | 4/2018 | Rummel et al. | |
| D826,234 S | 8/2018 | Zhou et al. | |
| D834,583 S | 11/2018 | Janzen et al. | |
| 10,134,815 B2 | 11/2018 | So et al. | |
| D835,284 S | 12/2018 | Barker et al. | |
| D835,285 S | 12/2018 | Barker et al. | |
| 10,356,334 B2 | 7/2019 | Moore et al. | |
| 10,721,410 B2 | 7/2020 | Moore et al. | |
| 10,779,734 B2 | 9/2020 | Fengler et al. | |
| 10,869,645 B2 | 12/2020 | Fengler et al. | |
| D916,294 S | 4/2021 | Murray et al. | |
| 10,992,848 B2 | 4/2021 | Murray et al. | |
| D919,810 S | 5/2021 | Murray et al. | |
| D919,811 S | 5/2021 | Murray et al. | |
| D919,812 S | 5/2021 | Murray et al. | |
| 11,025,867 B2 | 6/2021 | Westwick et al. | |
| 2001/0016679 A1 | 8/2001 | Futatsugi et al. | |
| 2001/0028458 A1 | 10/2001 | Xiao | |
| 2001/0049473 A1 | 12/2001 | Hayashi | |
| 2002/0013937 A1 | 1/2002 | Ostanevich et al. | |
| 2002/0016533 A1 | 2/2002 | Marchitto et al. | |
| 2002/0021355 A1 | 2/2002 | Utsui et al. | |
| 2002/0035330 A1 | 3/2002 | Cline et al. | |
| 2002/0076480 A1 | 6/2002 | Hsieh et al. | |
| 2002/0138008 A1 | 9/2002 | Tsujita et al. | |
| 2002/0143243 A1 | 10/2002 | Geordakoudi et al. | |
| 2002/0148902 A1 | 10/2002 | Schlieffers | |
| 2002/0155619 A1 | 10/2002 | Kurihara et al. | |
| 2002/0156380 A1 | 10/2002 | Feld et al. | |
| 2002/0161282 A1 | 10/2002 | Fulghum | |
| 2002/0161283 A1 | 10/2002 | Sendai | |
| 2002/0161284 A1 | 10/2002 | Tanaka | |
| 2002/0168096 A1 | 11/2002 | Hakamata et al. | |
| 2002/0175993 A1 | 11/2002 | Ueno et al. | |
| 2002/0177778 A1 | 11/2002 | Averback et al. | |
| 2002/0186478 A1 | 12/2002 | Watanabe et al. | |
| 2002/0196335 A1 | 12/2002 | Ozawa | |
| 2003/0001951 A1 | 1/2003 | Tsujita et al. | |
| 2003/0002036 A1 | 1/2003 | Haan et al. | |
| 2003/0042493 A1 | 3/2003 | Kazakevich | |
| 2003/0063398 A1 | 4/2003 | Abe et al. | |
| 2003/0080193 A1 | 5/2003 | Ryan et al. | |
| 2003/0117491 A1 | 6/2003 | Avni et al. | |
| 2003/0135092 A1 | 7/2003 | Cline et al. | |
| 2003/0153811 A1 | 8/2003 | Muckner | |
| 2003/0158470 A1 | 8/2003 | Wolters et al. | |
| 2003/0191368 A1 | 10/2003 | Wang et al. | |
| 2003/0216626 A1 | 11/2003 | Tsujita et al. | |
| 2003/0229270 A1 | 12/2003 | Suzuki et al. | |
| 2004/0006276 A1 | 1/2004 | Demos et al. | |
| 2004/0010183 A1 | 1/2004 | Dhindsa | |
| 2004/0020990 A1 | 2/2004 | Haven et al. | |
| 2004/0021859 A1 | 2/2004 | Cunningham | |
| 2004/0037454 A1 | 2/2004 | Ozawa et al. | |
| 2004/0044275 A1 | 3/2004 | Hakamata | |
| 2004/0046865 A1 | 3/2004 | Ueno et al. | |
| 2004/0133073 A1 | 7/2004 | Berci et al. | |
| 2004/0134990 A1 | 7/2004 | Fitch et al. | |
| 2004/0143162 A1 | 7/2004 | Krattiger et al. | |
| 2004/0148141 A1 | 7/2004 | Tsujita et al. | |
| 2004/0149998 A1 | 8/2004 | Henson et al. | |
| 2004/0156124 A1 | 8/2004 | Okada | |
| 2004/0186351 A1 | 9/2004 | Imaizumi et al. | |
| 2004/0218115 A1 | 11/2004 | Kawana et al. | |
| 2004/0225222 A1 | 11/2004 | Zeng et al. | |
| 2004/0245350 A1 | 12/2004 | Zeng | |
| 2004/0263643 A1 | 12/2004 | Imaizumi et al. | |
| 2005/0011954 A1 | 1/2005 | Hennick | |
| 2005/0027166 A1 | 2/2005 | Matsumoto et al. | |
| 2005/0051723 A1 | 3/2005 | Neagle et al. | |
| 2005/0088763 A1 | 4/2005 | Weaver et al. | |
| 2005/0096505 A1 | 5/2005 | Imaizumi et al. | |
| 2005/0140270 A1 | 6/2005 | Henson et al. | |
| 2005/0143627 A1 | 6/2005 | Cline et al. | |
| 2005/0146634 A1 | 7/2005 | Silverstein et al. | |
| 2005/0154319 A1 | 7/2005 | Cline et al. | |
| 2005/0171440 A1 | 8/2005 | Maki et al. | |
| 2005/0182291 A1 | 8/2005 | Hirata | |
| 2005/0182321 A1 | 8/2005 | Frangioni | |
| 2005/0203421 A1 | 9/2005 | Zeng et al. | |
| 2005/0225656 A1 | 10/2005 | Ihama | |
| 2005/0256373 A1 | 11/2005 | Bar-Or et al. | |
| 2005/0259318 A1 | 11/2005 | Armstrong | |
| 2005/0273011 A1 | 12/2005 | Hattery et al. | |
| 2005/0280783 A1 | 12/2005 | Yamasaki et al. | |
| 2005/0286130 A1 | 12/2005 | Bala | |
| 2005/0288593 A1 | 12/2005 | Geordakoudi et al. | |
| 2006/0002141 A1 | 1/2006 | Ouderkirk et al. | |
| 2006/0004292 A1 | 1/2006 | Beylin | |
| 2006/0017913 A1 | 1/2006 | Kawamata et al. | |
| 2006/0089554 A1 | 4/2006 | Ishihara et al. | |
| 2006/0094109 A1 | 5/2006 | Trainer | |
| 2006/0108509 A1 | 5/2006 | Franigioni et al. | |
| 2006/0146322 A1 | 7/2006 | Komachi et al. | |
| 2006/0149133 A1 | 7/2006 | Sugimoto et al. | |
| 2006/0155166 A1 | 7/2006 | Takahashi et al. | |
| 2006/0211915 A1 | 9/2006 | Takeuchi et al. | |
| 2006/0215406 A1 | 9/2006 | Thrailkill | |
| 2006/0217594 A1 | 9/2006 | Ferguson | |
| 2006/0241496 A1 | 10/2006 | Fengler et al. | |
| 2006/0247537 A1 | 11/2006 | Matsumoto | |
| 2006/0250696 A1 | 11/2006 | McGuire | |
| 2006/0256451 A1 | 11/2006 | Schaack | |
| 2006/0258910 A1 | 11/2006 | Stefanchik et al. | |
| 2007/0041195 A1 | 2/2007 | Chen | |
| 2007/0091634 A1 | 4/2007 | Sakurada | |
| 2007/0152161 A1 | 7/2007 | Olcott | |
| 2007/0177152 A1 | 8/2007 | Tearney et al. | |
| 2007/0203413 A1 | 8/2007 | Frangioni | |
| 2007/0213593 A1 | 9/2007 | Nakaoka | |
| 2007/0229309 A1 | 10/2007 | Tomita et al. | |
| 2007/0276184 A1 | 11/2007 | Okawa | |
| 2007/0276236 A1 | 11/2007 | Jong | |

(56)  References Cited

U.S. PATENT DOCUMENTS

| | | |
|---|---|---|
| 2008/0019615 A1 | 1/2008 | Schnee et al. |
| 2008/0021274 A1 | 1/2008 | Bayer et al. |
| 2008/0024868 A1 | 1/2008 | Okamura |
| 2008/0027280 A1 | 1/2008 | Fengler et al. |
| 2008/0039697 A1 | 2/2008 | Morishita |
| 2008/0064925 A1 | 3/2008 | Gill et al. |
| 2008/0074752 A1 | 3/2008 | Chaves et al. |
| 2008/0177140 A1 | 7/2008 | Cline et al. |
| 2008/0208006 A1 | 8/2008 | Farr |
| 2008/0217411 A1 | 9/2008 | Ledwith et al. |
| 2008/0246920 A1 | 10/2008 | Buczek et al. |
| 2008/0249368 A1 | 10/2008 | Takei |
| 2009/0012361 A1 | 1/2009 | MacKinnon et al. |
| 2009/0021739 A1 | 1/2009 | Tsujita et al. |
| 2009/0036734 A1 | 2/2009 | Dunki-Jacobs et al. |
| 2009/0040754 A1 | 2/2009 | Brukilacchio et al. |
| 2009/0052185 A1 | 2/2009 | Toriyama et al. |
| 2009/0114799 A1 | 5/2009 | Maeda |
| 2009/0114803 A1 | 5/2009 | Yamaguchi |
| 2009/0122135 A1 | 5/2009 | Matsui |
| 2009/0122152 A1 | 5/2009 | Yamaguchi et al. |
| 2009/0124854 A1 | 5/2009 | Yamaguchi et al. |
| 2009/0153797 A1 | 6/2009 | Allon et al. |
| 2009/0181339 A1 | 7/2009 | Liang et al. |
| 2009/0201577 A1 | 8/2009 | LaPlante et al. |
| 2009/0218405 A1 | 9/2009 | Joseph et al. |
| 2009/0236541 A1 | 9/2009 | Lommes et al. |
| 2009/0285762 A1 | 11/2009 | Flower |
| 2009/0290149 A1 | 11/2009 | Roth |
| 2010/0061604 A1 | 3/2010 | Nahm et al. |
| 2010/0065641 A1 | 3/2010 | Liu et al. |
| 2010/0079884 A1 | 4/2010 | Gere |
| 2010/0087741 A1 | 4/2010 | Douplik et al. |
| 2010/0094136 A1 | 4/2010 | Nakaoka et al. |
| 2010/0110168 A1 | 5/2010 | Avni et al. |
| 2010/0110393 A1 | 5/2010 | Chen et al. |
| 2010/0111361 A1 | 5/2010 | Tan et al. |
| 2010/0121146 A1 | 5/2010 | Sugimoto |
| 2010/0125164 A1 | 5/2010 | LaBombard |
| 2010/0155487 A1 | 6/2010 | Liu et al. |
| 2010/0157039 A1 | 6/2010 | Sugai |
| 2010/0168588 A1 | 7/2010 | Matsumoto et al. |
| 2010/0177180 A1 | 7/2010 | Yamaguchi et al. |
| 2010/0198010 A1 | 8/2010 | Cline et al. |
| 2010/0206731 A1 | 8/2010 | Lau et al. |
| 2010/0208487 A1 | 8/2010 | Li |
| 2010/0277817 A1 | 11/2010 | Durell |
| 2010/0308116 A1 | 12/2010 | Sani et al. |
| 2011/0019992 A1 | 1/2011 | Orf |
| 2011/0032350 A1 | 2/2011 | Kikuchi et al. |
| 2011/0071403 A1 | 3/2011 | Sevick-Muraca et al. |
| 2011/0073658 A1 | 3/2011 | Vassura et al. |
| 2011/0158914 A1 | 6/2011 | Yamada |
| 2011/0235017 A1 | 9/2011 | Iwasaki |
| 2011/0244506 A1 | 10/2011 | Sutter et al. |
| 2011/0270092 A1 | 11/2011 | Kang et al. |
| 2011/0279679 A1 | 11/2011 | Samuel |
| 2011/0290889 A1 | 12/2011 | Tamburini et al. |
| 2011/0306877 A1 | 12/2011 | Dvorsky et al. |
| 2011/0309275 A1 | 12/2011 | Azimi et al. |
| 2012/0006897 A1 | 1/2012 | Barkan et al. |
| 2012/0013773 A1 | 1/2012 | Yoshino et al. |
| 2012/0026325 A1 | 2/2012 | Bunker et al. |
| 2012/0044462 A1 | 2/2012 | Kaji |
| 2012/0150046 A1 | 6/2012 | Watson et al. |
| 2012/0256002 A1 | 10/2012 | O'Donnell et al. |
| 2012/0292530 A1 | 11/2012 | Ono et al. |
| 2012/0305650 A1 | 12/2012 | Prpa |
| 2012/0319645 A1 | 12/2012 | O'Donnell et al. |
| 2013/0008964 A1 | 1/2013 | Hawley et al. |
| 2013/0237762 A1 | 9/2013 | Fengler et al. |
| 2013/0306880 A1 | 11/2013 | Yamano et al. |
| 2014/0071328 A1 | 3/2014 | Miesak |
| 2014/0078378 A1 | 3/2014 | Demers et al. |
| 2014/0111652 A1 | 4/2014 | So et al. |

| | | |
|---|---|---|
| 2014/0139893 A1 | 5/2014 | Sugiyama et al. |
| 2014/0171764 A1* | 6/2014 | Kim ..................... A61B 5/0071 |
| | | 600/317 |
| 2014/0184769 A1 | 7/2014 | Ishihara et al. |
| 2014/0186351 A1 | 7/2014 | Britta |
| 2014/0187967 A1 | 7/2014 | Wood et al. |
| 2014/0192258 A1 | 7/2014 | Yang |
| 2014/0194687 A1 | 7/2014 | Fengler et al. |
| 2014/0217284 A1 | 8/2014 | So et al. |
| 2014/0261456 A1 | 9/2014 | Malackowski et al. |
| 2014/0264025 A1 | 9/2014 | Mohseni |
| 2015/0008390 A1 | 1/2015 | Lewis et al. |
| 2015/0018690 A1 | 1/2015 | Kang et al. |
| 2015/0083932 A1 | 3/2015 | Rizo |
| 2015/0184811 A1 | 7/2015 | Moore |
| 2015/0230698 A1 | 8/2015 | Cline et al. |
| 2015/0320296 A1 | 11/2015 | Morita |
| 2015/0341551 A1 | 11/2015 | Perrin |
| 2015/0381909 A1 | 12/2015 | Butte et al. |
| 2016/0035104 A1 | 2/2016 | Bigioi et al. |
| 2016/0041098 A1 | 2/2016 | Hirawake et al. |
| 2016/0044253 A1 | 2/2016 | Dainty et al. |
| 2016/0100763 A1 | 4/2016 | Fengler et al. |
| 2016/0173802 A1 | 6/2016 | Matsuo et al. |
| 2016/0245750 A1 | 8/2016 | Jiang et al. |
| 2016/0249019 A1 | 8/2016 | Westwick et al. |
| 2016/0360956 A1 | 12/2016 | Moore |
| 2017/0064257 A1 | 3/2017 | Westwick et al. |
| 2017/0064258 A1 | 3/2017 | Westwick et al. |
| 2017/0112369 A1 | 4/2017 | Czupalla et al. |
| 2017/0142314 A1 | 5/2017 | Moore et al. |
| 2017/0167980 A1 | 6/2017 | Dimitriadis et al. |
| 2017/0196527 A1 | 7/2017 | Kokubun |
| 2017/0245803 A1 | 8/2017 | Ahmed et al. |
| 2017/0273567 A1 | 9/2017 | Fengler et al. |
| 2017/0307355 A1 | 10/2017 | Seitz et al. |
| 2017/0354392 A1 | 12/2017 | Fengler et al. |
| 2018/0199801 A1* | 7/2018 | Tsuruta ................ A61B 1/0638 |
| 2018/0234603 A1 | 8/2018 | Moore et al. |
| 2019/0298471 A1 | 10/2019 | Holop |
| 2020/0154019 A1 | 5/2020 | Murray et al. |
| 2021/0105393 A1 | 4/2021 | Moore et al. |
| 2021/0166806 A1 | 6/2021 | Fengler et al. |
| 2021/0274131 A1 | 9/2021 | Westwick et al. |
| 2021/0307613 A1 | 10/2021 | Fengler et al. |
| 2022/0030149 A1 | 1/2022 | Moore et al. |
| 2023/0031797 A1 | 2/2023 | Fengler et al. |
| 2023/0172444 A1 | 6/2023 | Bauer |
| 2024/0029869 A1 | 1/2024 | Fengler et al. |
| 2024/0298091 A1 | 9/2024 | Moore et al. |
| 2024/0373115 A1 | 11/2024 | Moore et al. |

FOREIGN PATENT DOCUMENTS

| | | |
|---|---|---|
| CN | 101631508 A | 1/2010 |
| CN | 101726980 A | 6/2010 |
| CN | 101828139 A | 9/2010 |
| CN | 102026668 A | 4/2011 |
| CN | 201974160 U | 9/2011 |
| CN | 102257510 A | 11/2011 |
| CN | 102711652 A | 10/2012 |
| CN | 103543609 A | 1/2014 |
| CN | 104958111 A | 10/2015 |
| DE | 19535114 A1 | 3/1996 |
| DE | 19608027 A1 | 9/1996 |
| DE | 10028233 A1 | 1/2002 |
| DE | 20 2005 021 111 U1 | 5/2007 |
| EP | 0512965 A1 | 11/1992 |
| EP | 0672379 A1 | 9/1995 |
| EP | 0774865 A2 | 5/1997 |
| EP | 0792618 A1 | 9/1997 |
| EP | 0671706 B1 | 6/1999 |
| EP | 1374755 A1 | 1/2004 |
| EP | 1 496 690 A2 | 1/2005 |
| EP | 1883337 A1 | 2/2008 |
| EP | 2051603 A1 | 4/2009 |
| EP | 2859837 A1 | 4/2015 |
| EP | 2 988 654 B1 | 6/2020 |
| FR | 2671405 A1 | 7/1992 |

(56)                References Cited

FOREIGN PATENT DOCUMENTS

| | | | |
|----|----|----|----|
| JP | S60-246733 | A | 12/1985 |
| JP | S61-159936 | A | 7/1986 |
| JP | H-01-135349 | A | 5/1989 |
| JP | 03-97439 | A | 4/1991 |
| JP | 03-97441 | A | 4/1991 |
| JP | 03-97442 | A | 4/1991 |
| JP | 05-115435 | A | 5/1993 |
| JP | 06-125911 | A | 5/1994 |
| JP | H07-155285 | A | 6/1995 |
| JP | H07-155286 | A | 6/1995 |
| JP | H07-155290 | A | 6/1995 |
| JP | H07-155291 | A | 6/1995 |
| JP | H07-155292 | A | 6/1995 |
| JP | H07-204156 | A | 8/1995 |
| JP | H07-222712 | A | 8/1995 |
| JP | H07-250804 | A | 10/1995 |
| JP | H07-250812 | A | 10/1995 |
| JP | H07-327913 | A | 12/1995 |
| JP | H08-126605 | A | 5/1996 |
| JP | 08-140928 | A2 | 6/1996 |
| JP | 08-140929 | A2 | 6/1996 |
| JP | H08-224208 | A | 9/1996 |
| JP | H08-224209 | A | 9/1996 |
| JP | H08-224210 | A | 9/1996 |
| JP | H08-224240 | A | 9/1996 |
| JP | H08-252218 | A | 10/1996 |
| JP | H09-19408 | A | 1/1997 |
| JP | 09-066023 | A2 | 3/1997 |
| JP | 09-070384 | A2 | 3/1997 |
| JP | H9-294706 | A | 11/1997 |
| JP | H9-294707 | A | 11/1997 |
| JP | H10-14926 | A | 1/1998 |
| JP | H10-127563 | A | 5/1998 |
| JP | H10-151104 | A | 6/1998 |
| JP | 10-225427 | A2 | 8/1998 |
| JP | H10-201700 | A | 8/1998 |
| JP | H10-201707 | A | 8/1998 |
| JP | H10-225426 | A | 8/1998 |
| JP | H10-243915 | A | 9/1998 |
| JP | H10-243920 | A | 9/1998 |
| JP | H10-308114 | A | 11/1998 |
| JP | H10-309281 | A | 11/1998 |
| JP | H10-309282 | A | 11/1998 |
| JP | H10-321005 | A | 12/1998 |
| JP | H10-328129 | A | 12/1998 |
| JP | H11-47079 | A | 2/1999 |
| JP | 11-089789 | A2 | 4/1999 |
| JP | H11-95120 | A | 4/1999 |
| JP | H11-104059 | A | 4/1999 |
| JP | H11-104060 | A | 4/1999 |
| JP | H11-104061 | A | 4/1999 |
| JP | H11-104070 | A | 4/1999 |
| JP | H11-113839 | A | 4/1999 |
| JP | H11-155812 | A | 6/1999 |
| JP | H11-244220 | A | 9/1999 |
| JP | H11-332819 | A | 12/1999 |
| JP | 2000-504968 | A | 4/2000 |
| JP | 2000-230903 | A | 8/2000 |
| JP | 2000-245693 | A | 9/2000 |
| JP | 2000-354583 | A | 12/2000 |
| JP | 2001-78205 | A | 3/2001 |
| JP | 2001-518241 | A | 10/2001 |
| JP | 2002-000560 | A | 1/2002 |
| JP | 02-049302 | A | 2/2002 |
| JP | 2002-244122 | A | 8/2002 |
| JP | 2003-045210 | A | 2/2003 |
| JP | 2004-024611 | A | 1/2004 |
| JP | 2004-094043 | A | 3/2004 |
| JP | 2004-163902 | A | 6/2004 |
| JP | 2004-520105 | A | 7/2004 |
| JP | 2004-247156 | A | 9/2004 |
| JP | 2004-289545 | A | 10/2004 |
| JP | 2004-292722 | A | 10/2004 |
| JP | 2005-010315 | A | 1/2005 |
| JP | 2005-058618 | A2 | 3/2005 |
| JP | 2005-058619 | A2 | 3/2005 |
| JP | 2005-058620 | A2 | 3/2005 |
| JP | 2005-080819 | A2 | 3/2005 |
| JP | 2005-081079 | A2 | 3/2005 |
| JP | 2005-149996 | A | 6/2005 |
| JP | 2005-292404 | A | 10/2005 |
| JP | 2005-326777 | A | 11/2005 |
| JP | 2006-3103 | A1 | 1/2006 |
| JP | 2006-61376 | A | 3/2006 |
| JP | 2006-73767 | A | 3/2006 |
| JP | 2006-087764 | A | 4/2006 |
| JP | 2006-525494 | A | 11/2006 |
| JP | 2006-326153 | A | 12/2006 |
| JP | 2007-029453 | A | 2/2007 |
| JP | 2007-072392 | A | 3/2007 |
| JP | 2007-089840 | A | 4/2007 |
| JP | 2008-48787 | A | 3/2008 |
| JP | 2009-259703 | A | 11/2009 |
| JP | 2010-107751 | A | 5/2010 |
| JP | 2010-117442 | A | 5/2010 |
| JP | 2010-524194 | A | 7/2010 |
| JP | 2011-500921 | A | 1/2011 |
| JP | 2011-72424 | A | 4/2011 |
| JP | 2011-110272 | A | 6/2011 |
| JP | 2011-161046 | A | 8/2011 |
| JP | 2011-169819 | A | 9/2011 |
| JP | 2011-528918 | A | 12/2011 |
| JP | 5231625 | B2 | 7/2013 |
| JP | 2013-541370 | A | 11/2013 |
| JP | 2014-123941 | A | 7/2014 |
| JP | 2015-16332 | A | 1/2015 |
| JP | 2016-7234 | A | 1/2016 |
| JP | 5859578 | B2 | 2/2016 |
| RU | 99592 | U1 | 11/2010 |
| WO | WO-1993/04648 | A1 | 3/1993 |
| WO | WO-1994/13191 | A1 | 6/1994 |
| WO | WO-1995/26673 | A2 | 10/1995 |
| WO | WO-1998/24360 | A1 | 6/1998 |
| WO | WO-1999/01749 | A1 | 1/1999 |
| WO | WO-1999/53832 | A1 | 10/1999 |
| WO | WO-2000/42910 | A1 | 7/2000 |
| WO | WO-2000/54652 | A1 | 9/2000 |
| WO | WO-2002/007587 | A2 | 1/2002 |
| WO | WO-2002/50518 | A2 | 6/2002 |
| WO | WO-2003/059159 | A2 | 7/2003 |
| WO | WO-2003/059159 | A8 | 7/2003 |
| WO | WO-2006/116847 | A1 | 11/2006 |
| WO | WO-2007/070382 | A2 | 6/2007 |
| WO | WO-2007/081707 | A2 | 7/2007 |
| WO | WO-2008/011722 | A1 | 1/2008 |
| WO | WO-2008/071240 | A1 | 6/2008 |
| WO | WO-2009/033021 | A2 | 3/2009 |
| WO | WO-2011/120688 | A1 | 10/2011 |
| WO | WO-2013/160279 | A1 | 10/2013 |
| WO | WO-2014/066906 | A1 | 5/2014 |
| WO | WO-2014/176375 | A2 | 10/2014 |
| WO | 2015/164774 | A1 | 10/2015 |
| WO | WO-2016/055837 | A1 | 4/2016 |

OTHER PUBLICATIONS

Alfano, R.R et al. (Oct. 1987). "Fluorescence Spectra From Cancerous and Normal Human Breast and Lung Tissues," *IEEE Journal of Quantum Electronics* QE-23(10):1806-1811.

Andersson-Engels, S. et al. (Mar. 1989). "Tissue Diagnostics Using Laser Induced Fluorescence," *Ber. Bunsenges Physical Chemistry* 93(3):335-342.

Australian Notice of Allowance mailed on Jun. 26, 2019 for Australian Patent Application No. 2016351730 filed on Nov. 10, 2016, three pages.

Australian Office Action mailed on Jun. 28, 2018 for Australian Patent Application No. 2016351730 filed on Nov. 10, 2016, five pages.

Australian Office Action mailed on May 10, 2019 for Australian Patent Application No. 2016351730 filed on Nov. 10, 2016, ten pages.

(56)             References Cited

OTHER PUBLICATIONS

Bhunchet, E. et al. (Apr. 2002). "Fluorescein Electronic Endoscopy: A Novel Method for Detection of Early Stage Gastric Cancer Not Evident to Routine Endoscopy," *Gastrointestinal Endoscopy* 55(4):562-571.

Canadian Office Action mailed on Feb. 1, 2017 for Canadian Patent Application No. 171282, filed on Oct. 27, 2016, two pages.

Canadian Office Action mailed on Feb. 19, 2019 for CA Patent Application No. 2,998,920 filed on Mar. 16, 2018, four pages.

Chinese Notice of Allowance mailed on Jun. 19, 2017 for Chinese Patent Application No. 201280022284.3, filed on Nov. 7, 2013, four pages.

Chinese Office Action mailed on Jul. 29, 2016 for Chinese Patent Application No. 201280022284.3 filed on Mar. 8, 2012, eight pages.

Chinese Office Action mailed on Mar. 14, 2017 for Chinese Patent Application No. 201280022284.3, filed on Nov. 7, 2013, seven pages.

Chinese Office Action mailed on Nov. 24, 2015 for Chinese Patent Application No. 201280022284.3 filed on Mar. 8, 2012, sixteen pages.

Chinese Office Action mailed on Sep. 26, 2018 for Chinese Patent Application No. 2018092001857100, filed on Sep. 4, 2017, nineteen pages.

Dawson, J.B et al. (Jul. 1980). "A Theoretical and Experimental Study of Light Absorption and Scattering by In Vivo Skin," *Phys. Med. Biol.* 25(4):695-709.

European Notice of Allowance mailed on Feb. 28, 2018 for EP Patent Application No. 12754208.2 filed Oct. 4, 2013, six pages.

European Notice of Allowance mailed on Jul. 12, 2018 for EP Patent Application No. 12754208.2 filed Oct. 4, 2013, two pages.

European Notice of Allowance mailed on Jun. 22, 2017 for EP Patent Application No. 08706262.6 filed on Aug. 21, 2009, two pages.

European Notice of Allowance mailed on Mar. 6, 2018 for EP Patent Application No. 13180297.7 filed Aug. 13, 2013, seven pages.

European Notice of Allowance mailed on Mar. 18, 2019 for EP Patent Application No. 09819758.5, filed on May 4, 2011, seven pages.

European Notice of Allowance mailed on May 25, 2018 for EP Patent Application No. 13180297.7 filed Aug. 13, 2013, two pages.

European Notice of Allowance mailed on Nov. 25, 2016 for EP Patent Application No. 08706262.6 filed on Aug. 21, 2009, eight pages.

European Office Action mailed on Apr. 6, 2017, for EP Patent Application No. 09819758.5, filed on May 4, 2011, five pages.

European Office Action mailed on Apr. 13, 2017, for EP Patent Application No. 12754208.2 filed on Oct. 4, 2013, five pages.

European Office Action mailed on Dec. 3, 2015 for EP Patent Application No. 08706262.6 filed on Jan. 23, 2008; fifteen pages.

European Office Action mailed on Jan. 23, 2017 for EP Patent Application No. 16186321.2 filed on Aug. 30, 2016, two pages.

European Office Action mailed on Nov. 3, 2015 for EP Patent Application No. 12754208.2 filed Oct. 4, 2013, four pages.

European Office Action mailed on Nov. 19, 2015 for EP Patent Application No. 07 785 001.4, filed on Jul. 30, 2007, four pages.

European Office Action mailed on Sep. 29, 2015, for EP Patent Application No. 09721252.6 filed Mar. 18, 2009; five pages.

European Search Report mailed Dec. 21, 2016 for EP Patent Application No. 16186321.2 filed on Aug. 30, 2016, nine pages.

European Search Report mailed on Feb. 18, 2019 for EP Patent Application No. 18178620.3 filed on Jun. 19, 2018, eight pages.

European Search Report mailed on Jan. 24, 2012 for EP Patent Application No. 07785001.4 filed on Jul. 30, 2007, seven pages.

European Search Report mailed on Jul. 17, 2014 for EP Patent Application No. 09721252.6 filed Mar. 18, 2009; eleven pages.

European Search Report mailed on Oct. 1, 2014 for EP Patent Application No. 12754208.2 filed on Mar. 8, 2012, five pages.

European Search Report mailed on Oct. 9, 2013, for European Patent Application No. 06721854.5, filed on May 4, 2005, seven pages.

European Search Report mailed on Sep. 20, 2013 for EP Patent Application No. 08706262.6 filed on Jan. 23, 2008, five pages.

Georgakoudi, I et al. (2003). "Quantitative Characterization of Biological Tissue Using Optical Spectroscopy," in Chapter 31 of *Biomedical Photonics Handbook*, Tuan Vo-Dinh (ed.), CRC Press, New York, thirty three pages.

Georgakoudi, I et al. (Apr. 2005). "Characterization of Dysplastic Tissue Morphology and Biochemistry in Barrett's Esophagus using Diffuse Reflectance and Light Scattering Spectroscopy," *Techniques in Gastrointestinal Endoscopy* 7(2):100-105.

Hubel, P.M. et al. (2004). "Spatial Frequency Response of Color Image Sensors: Bayer Color Filters and Foveon X3," *Proceedings of SPIE* 5301:402-406.

Hung, J. et al. (1991). "Autofluorescence of Normal and Malignant Bronchial Tissue," *Lasers in Surgery and Medicine* 11(2):99-105.

Indian Office Action dated Jan. 31, 2018 for Indian Patent Application No. 6532/DELNP/2010 filed on Sep. 16, 2010, five pages.

Indian Office Action dated Jun. 26, 2018 for Indian Patent Application No. 8678/DELNP/2013 filed on Mar. 8, 2012, five pages.

International Preliminary Report on Patentability mailed on Dec. 27, 2018 for International Patent Application No. PCT/CA2017/050734 filed on Jun. 14, 2017, six pages.

International Preliminary Report on Patentability mailed on Feb. 3, 2009 for International Patent Application No. PCT/CA2007/001335 filed on Jul. 30, 2007, five pages.

International Preliminary Report on Patentability mailed on May 24, 2018 for International Patent Application No. PCT/CA2016/051315 filed on Nov. 10, 2016, nine pages.

International Preliminary Report on Patentability mailed on Nov. 6, 2007 for International Patent Application No. PCT/CA2006/000669, filed on Apr. 27, 2006, nine pages.

International Preliminary Report on Patentability mailed on Sep. 21, 2010 for International Patent Application No. PCT/US2009/037506, filed on Mar. 18, 2009, seven pages.

International Search Report and written Opinion mailed on Apr. 24, 2017 for International Patent Application No. PCT/CA2017/050083, filed on Jan. 26, 2017, seven pages.

International Search Report and written Opinion mailed on Feb. 10, 2017 for International Patent Application No. PCT/CA2016/051315 filed on Nov. 10, 2016, thirteen pages.

International Search Report and Written Opinion mailed on Sep. 18, 2017 for International Patent Application No. PCT/CA2017/050734, filed on Jun. 14, 2017, eight pages.

International Search Report mailed on Aug. 3, 2006, for International Patent Application No. PCT/CA2006/000669, filed on Apr. 27, 2006, three pages.

International Search Report mailed on Aug. 3, 2012, for International Patent Application No. PCT/IB2012/000601, filed on Mar. 8, 2012, three pages.

International Search Report mailed on Dec. 7, 2007, for International Patent Application No. PCT/CA2007/001335, filed on Jul. 30, 2007, two pages.

International Search Report mailed on Jan. 21, 2002 for International Patent Application No. PCT/US2001/022198, filed on Jul. 13, 2001, three pages.

International Search Report mailed on Jul. 22, 2009 for International Patent Application No. PCT/US09/37506, filed on Mar. 18, 2009, two pages.

International Search Report mailed on May 13, 2008 for Intentional Patent Application No. PCT/CA2008/00015, filed on Jan. 8, 2008, one page.

Invitation to Pay additional Fees and, where Applicable, Protest Fee, mailed on Dec. 22, 2016 for International Patent Application No. PCT/CA2016/051315, filed on Nov. 10, 2016, two pages.

Japanese Final Office Action mailed on Aug. 2, 2013 for Japanese Application No. 2008-509275, filed on Apr. 27, 2006, four pages.

Japanese Notice of Allowance mailed on Apr. 2, 2018 for Japanese Patent Application No. 2017-018858 filed on Feb. 3, 2017, six pages.

Japanese Notice of Allowance mailed on Jan. 5, 2017 for Japanese Patent Application No. 2015-238784, filed on Dec. 7, 2015, six pages.

(56)　　　　　　References Cited

OTHER PUBLICATIONS

Japanese Notice of Allowance mailed on Nov. 17, 2017 for Japanese Application No. 2016-253736 filed on Dec. 27, 2016, six pages.
Japanese Notice of Allowance mailed on Nov. 28, 2016 for Japanese Patent Application No. 2015-245598, filed on Mar. 8, 2012, six pages.
Japanese Office Action mailed on Apr. 3, 2015 for Japanese Patent Application No. 2013-058356, filed Mar. 18, 2009, four pages.
Japanese Office Action mailed on Apr. 20, 2012 for Japanese Patent Application No. 2011-500921, filed Mar. 18, 2009, four pages.
Japanese Office Action mailed on Dec. 8, 2017 for Japanese Patent Application No. 2017-018858 filed on Feb. 3, 2017, six pages.
Japanese Office mailed on Dec. 26, 2012 for Japanese Patent Application No. 2011-500921, filed on Mar. 18, 2009, two pages.
Japanese Office Action mailed on Feb. 17, 2012 for Japanese Application No. 2008-509275, filed on Apr. 27, 2006, six pages.
Japanese Office Action mailed on Jul. 22, 2014 for Japanese Patent Application No. 2013-557187 filed Mar. 8, 2012, seven pages.
Japanese Office Action mailed on Mar. 9, 2015 for Japanese Patent Application No. 2013-557187, filed Mar. 8, 2012, five pages.
Japanese Office Action mailed on May 26, 2014 in Japanese Patent Application No. 2013-058356, filed on Mar. 18, 2009, w/Concise Explanation of the Relevance, three pages.
Japanese Office Action mailed on Nov. 11, 2011 for Japanese Application No. 2009-521077, filed on Jul. 30, 2007, four pages.
Japanese Office Action mailed on Sep. 14, 2012 for Japanese Application No. 2008-509275, filed on Apr. 27, 2006, seven pages.
Japanese Office Action mailed on Sep. 19, 2014 for Japanese Application No. 2013-246636, filed on Apr. 27, 2006, six pages.
Korean Decision on the Trial Against Final Rejection from the Intellectual Property Tribunal (IPT) mailed on Sep. 25, 2017 for Korean Patent Application No. 2013-7026479, filed on Oct. 7, 2013, seventeen pages.
Korean Notice of Allowance mailed on Dec. 13, 2017 for Korean Patent Application No. 10-2017-7008654, filed on Mar. 29, 2017, three pages.
Korean Notice of Allowance mailed on Jan. 2, 2017 for Korean Patent Application No. 10- 2015-7033310, filed on Nov. 20, 2015, three pages.
Korean Office Action mailed on Aug. 20, 2015 for Korean Patent Application No. 2013-7026479 filed on Mar. 8, 2012, three pages.
Korean Office Action mailed on Aug. 30, 2016 for Korean Patent Application No. 10-2015-7033310 filed on Mar. 8, 2012, seven pages.
Korean Office Action mailed on Dec. 8, 2015 for Korean Patent Application No. 20157033310 filed on Mar. 8, 2012, seven pages.
Korean Office Action mailed on Jun. 27, 2017 for Korean Patent Application No. 2017-7008654, filed on Mar. 29, 2017, ten pages.
Lyon, R.E. et al. (2002). "Eyeing the Camera: Into the Next Century," 10 Color and Imaging Conference Final Program & Proceedings 349-355.
Russian Notice of Allowance mailed on Aug. 19, 2016 for Russian Patent Application No. 2013144845/07, filed on Mar. 8, 2012, thirteen pages.
Török, B. et al. (May 1996). "Simultane digitale Indocyaningrün- und Fluoreszeinangiographie (Simultaneous Digital ICG and Fluorescein Angiography)," Klin Monatsbl Augenheilkd 208(5):333-336, (with English Translation of the Introduction).
U.S. Final Office Action mailed on Apr. 24, 2015 for U.S. Appl. No. 12/933,512, filed Nov. 24, 2010, nineteen pages.
U.S. Final Office Action mailed on Aug. 7, 2017 for U.S. Appl. No. 15/343,038, filed Nov. 3, 2016, eleven pages.
U.S. Final Office Action mailed on Aug. 10, 2017 for U.S. Appl. No. 15/343,034, filed Nov. 3, 2016, twelve pages.
U.S. Final Office Action mailed on Aug. 11, 2017 for U.S. Appl. No. 14/860,687, filed Sep. 21, 2015, seventeen pages.
U.S. Final Office Action mailed on Dec. 14, 2018 for U.S. Appl. No. 15/584,405, filed May 2, 2017, seven pages.
U.S. Final Office Action mailed on Feb. 1, 2018 for U.S. Appl. No. 15/584,405, filed May 2, 2017, ten pages.

U.S. Final Office Action mailed on Feb. 27, 2017 for U.S. Appl. No. 15/247,419, filed Aug. 25, 2016, ten pages.
U.S. Final Office Action mailed on Jan. 11, 2019 for U.S. Appl. No. 15/343,038, filed Nov. 3, 2016, twelve pages.
U.S. Final Office Action mailed on Jan. 14, 2019 for U.S. Appl. No. 14/860,687, filed Sep. 21, 2015, sixteen pages.
U.S. Final Office Action mailed on Jan. 22, 2019 for U.S. Appl. No. 15/343,034, filed Nov. 3, 2016, twelve pages.
U.S. Final Office Action mailed on Jul. 23, 2008 for U.S. Appl. No. 11/122,267, filed May 4, 2016, six pages.
U.S. Final Office Action mailed on Jun. 5, 2014 for U.S. Appl. No. 12/761,462, filed Apr. 16, 2010, fourteen pages.
U.S. Final Office Action mailed on Jun. 18, 2015 for U.S. Appl. No. 14/154,177 filed on Jan. 13, 2014, eight pages.
U.S. Final Office Action mailed on Mar. 22, 2016 for U.S. Appl. No. 14/873,842, filed Oct. 2, 2015, eighteen pages.
U.S. Final Office Action mailed on May 11, 2011 for U.S. Appl. No. 11/412,715, filed Apr. 26, 2006, eight pages.
U.S. Final Office Action mailed on May 21, 2012 for U.S. Appl. No. 11/964,330, filed Dec. 26, 2007, twelve pages.
U.S. Final Office Action mailed on Nov. 24, 2009 for U.S. Appl. No. 11/009,965, filed Dec. 10, 2004, fourteen pages.
U.S. Non Final Office Action mailed on Apr. 2, 2009 for U.S. Appl. No. 11/009,965, filed Dec. 10, 2004, thirteen pages.
U.S. Non Final Office Action mailed on Aug. 15, 2018 for U.S. Appl. No. 15/348,664, filed Nov. 10, 2016, eleven pages.
U.S. Non Final Office Action mailed on Aug. 16, 2013 for U.S. Appl. No. 12/761,462, filed Apr. 16, 2010, ten pages.
U.S. Non Final Office Action mailed on Aug. 16, 2013 for U.S. Appl. No. 12/761,523, filed Apr. 16, 2010, nine pages.
U.S. Non Final Office Action mailed on Dec. 10, 2010 for U.S. Appl. No. 11/412,715, filed Apr. 26, 2006, ten pages.
U.S. Non Final Office Action mailed on Dec. 14, 2011 for U.S. Appl. No. 11/412,715, filed Apr. 26, 2006, eight pages.
U.S. Non Final Office Action mailed on Feb. 1, 2017 for U.S. Appl. No. 14/860,687, filed Sep. 21, 2015, fifteen pages.
U.S. Non Final Office Action mailed on Feb. 3, 2010 for U.S. Appl. No. 11/626,308, filed Jan. 23, 2007, eleven pages.
U.S. Non Final Office Action mailed on Feb. 5, 2019 for U.S. Appl. No. 15/623,100, filed Jun. 14, 2017, ten pages.
U.S. Non Final Office Action mailed on Jan. 2, 2008 for U.S. Appl. No. 11/122,267, filed May 4, 2005, five pages.
U.S. Non Final Office Action mailed on Jan. 20, 2016 for U.S. Appl. No. 14/629,473, filed Feb. 23, 2015, fifteen pages.
U.S. Non Final Office Action mailed on Jan. 26, 2017 for U.S. Appl. No. 15/343,034, filed Nov. 3, 2016, seventeen pages.
U.S. Non Final Office Action mailed on Jan. 27, 2017 for U.S. Appl. No. 15/343,038, filed Nov. 3, 2016, fifteen pages.
U.S. Non Final Office Action mailed on Jul. 2, 2013 for U.S. Appl. No. 12/933,512, filed Nov. 24, 2010, twelve pages.
U.S. Non Final Office Action mailed on Jul. 17, 2003 for U.S. Appl. No. 09/905,642, filed Jul. 13, 2001, six pages.
U.S. Non Final Office Action mailed on Jun. 1, 2007 for U.S. Appl. No. 10/899,648, filed Jul. 26, 2004, seven pages.
U.S. Non Final Office Action mailed on Jun. 5, 2018 for U.S. Appl. No. 14/860,687, filed Sep. 21, 2015, eighteen pages.
U.S. Non Final Office Action mailed on Jun. 8, 2018 for U.S. Appl. No. 15/343,034, filed Nov. 3, 2016, thirteen pages.
U.S. Non Final Office Action mailed on Jun. 8, 2018 for U.S. Appl. No. 15/584,405, filed May 2, 2017, eight pages.
U.S. Non Final Office Action mailed on Jun. 9, 2011 for U.S. Appl. No. 11/830,323, filed Jul. 30, 2007, five pages.
U.S. Non Final Office Action mailed on Jun. 20, 2008 for U.S. Appl. No. 11/009,398, filed Dec. 10, 2004, fifteen pages.
U.S. Non Final Office Action mailed on Jun. 23, 2010 for U.S. Appl. No. 11/009,965, filed Dec. 10, 2004, fifteen pages.
U.S. Non Final Office Action mailed on Jun. 27, 2014 for U.S. Appl. No. 13/415,561, filed Mar. 3, 2012, fourteen pages.
U.S. Non Final Office Action mailed on May 18, 2004 for U.S. Appl. No. 10/050,601, filed Jan. 15, 2002, eight pages.
U.S. Non Final Office Action mailed on May 25, 2018 for U.S. Appl. No. 15/343,038, filed Nov. 3, 2016, eleven pages.

(56) References Cited

OTHER PUBLICATIONS

U.S. Non Final Office Action mailed on Nov. 5, 2014 for U.S. Appl. No. 13/930,225, filed Jun. 28, 2013, six pages.
U.S. Non Final Office Action mailed on Nov. 23, 2009 for U.S. Appl. No. 11/969,974, filed Jan. 7, 2008, seven pages.
U.S. Non Final Office Action mailed on Oct. 5, 2016 for U.S. Appl. No. 15/247,419, filed Aug. 25, 2016, eight pages.
U.S. Non Final Office Action mailed on Oct. 7, 2011 for U.S. Appl. No. 11/964,330, filed Dec. 26, 2007; ten pages.
U.S. Non Final Office Action mailed on Oct. 23, 2013 for U.S. Appl. No. 13/415,561, filed Mar. 8, 2012, ten pages.
U.S. Non Final Office Action mailed on Sep. 6, 2016 for U.S. Appl. No. 14/873,842, filed Oct. 2, 2015, seven pages.
U.S. Non Final Office Action mailed on Sep. 12, 2014 for U.S. Appl. No. 14/154,177, filed on Jan. 13, 2014, four pages.
U.S. Non Final Office Action mailed on Sep. 25, 2017 for U.S. Appl. No. 15/584,405, filed May 2, 2017, eight pages.
U.S. Non Final Office Action with Restriction Requirement mailed on Mar. 4, 2011 for U.S. Appl. No. 11/830,323, filed Jul. 30, 2007, nine pages.
U.S. Appl. No. 15/810,911, filed Nov. 13, 2017. (Copy not submitted herewith pursuant to the waiver of 37 C.F.R. § 1.98(a)(2)(iii) issued by the Office on Sep. 21, 2004).
U.S. Notice of Allowance mailed on Apr. 7, 2004 for U.S. Appl. No. 09/905,642, filed Jul. 13, 2001, six pages.
U.S. Notice of Allowance mailed on Aug. 6, 2015 for U.S. Appl. No. 13/853,656, filed Mar. 29, 2013, seven pages.
U.S. Notice of Allowance mailed on Aug. 26, 2004 for U.S. Appl. No. 10/050,601, filed Jan. 15, 2002, eight pages.
U.S. Notice of Allowance mailed on Dec. 10, 2012 for U.S. Appl. No. 11/964,330, filed Dec. 26, 2007, seven pages.
U.S. Notice of Allowance mailed on Dec. 30, 2016 for U.S. Appl. No. 14/873,842, filed Oct. 2, 2015, eleven pages.
U.S. Notice of Allowance mailed on Feb. 25, 2010 for U.S. Appl. No. 11/969,974, filed Jan. 7, 2008, four pages.
U.S. Notice of Allowance mailed on Jan. 2, 2008 for U.S. Appl. No. 10/899,648, filed Jul. 26, 2004, three pages.
U.S. Notice of Allowance mailed on Jul. 10, 2017 for U.S. Appl. No. 15/247,419, filed Aug. 25, 2016, eight pages.
U.S. Notice of Allowance mailed on Jun. 25, 2015 for U.S. Appl. No. 12/933,512, filed Nov. 24, 2010 fourteen pages.
U.S. Notice of Allowability mailed on Mar. 10, 2005 for U.S. Appl. No. 10/050,601, filed Jan. 15, 2002, five pages.
U.S. Notice of Allowance mailed on Mar. 22, 2013 for U.S. Appl. No. 11/964,330, filed Dec. 26, 2007, eight pages.
U.S. Notice of Allowance mailed on Mar. 28, 2016 for U.S. Appl. No. 13/853,656, filed Mar. 29, 2013, eight pages.
U.S. Notice of Allowance mailed on May 18, 2015 for U.S. Appl. No. 13/930,225, filed Jun. 28, 2013, nine pages.
U.S. Notice of Allowance mailed on Nov. 23, 2015 for U.S. Appl. No. 13/853,656, filed Mar. 29, 2013, seven pages.
U.S. Notice of Allowance mailed on Oct. 5, 2007 for U.S. Appl. No. 10/899,648, filed Jul. 26, 2004, six pages.
U.S. Notice of Allowance mailed on Oct. 10, 2014 for U.S. Appl. No. 12/761,462, filed Apr. 16, 2010, ten pages.
U.S. Notice of Allowance mailed on Sep. 10, 2013 for U.S. Appl. No. 11/412,715, filed Apr. 26, 2006, eight pages.
U.S. Notice of Allowance mailed on Sep. 14, 2012 for U.S. Appl. No. 11/830,323, filed Jul. 30, 2007, eight pages.
U.S. Restriction Requirement mailed on Feb. 7, 2019 for U.S. Appl. No. 29/562,795, filed Apr. 28, 2016, seven pages.
Written Opinion of the International Searching Authority mailed on Aug. 3, 2006 for International Patent Application No. PCT/CA2006/000669, filed on Apr. 27, 2006, eight pages.
Written Opinion of the International Searching Authority mailed on Dec. 7, 2007 for International Patent Application No. PCT/CA2007/001335, filed on Jul. 30, 2007, four pages.
Brazilian Office Action mailed Aug. 5, 2019, for Patent Application No. BR112013022997-7, filed Mar. 8, 2012, 4 pages.

Canadian Office Action mailed on Nov. 5, 2019, for Canadian Patent Application No. 3,027,592, filed on Jun. 14, 2017, 4 pages.
European Extended Search Report mailed Oct. 16, 2019, for Patent Application No. 17743524.5, filed Jan. 26, 2017, 4 pages.
European Extended Search Report mailed May 7, 2019, for Patent Application No. 16863277.6, filed Nov. 10, 2016, 3 pages.
Japanese Office Action mailed on Jul. 12, 2019, for Patent Application No. 2018-516161, filed Nov. 10, 2016, 21 pages.
Sensitization (photography), definition from Wikipedia, original language German, 6 pages.
U.S. Non-Final Office Action mailed on Aug. 2, 2019, for U.S. Appl. No. 15/623,100, filed on Jun. 14, 2017, 12 pages.
U.S. Non-Final Office Action mailed on Aug. 21, 2019, for U.S. Appl. No. 15/584,405, filed May 2, 2017, 6 pages.
U.S. Non-Final Office Action mailed on Aug. 23, 2019, for U.S. Appl. No. 15/343,038, filed Nov. 3, 2016, 14 pages.
U.S. Non-Final Office Action mailed on Aug. 23, 2019, for U.S. Appl. No. 14/860,687, filed Sep. 21, 2015, 14 pages.
U.S. Non-Final Office Action mailed on Aug. 23, 2019, for U.S. Appl. No. 15/343,034, filed Nov. 3, 2016, 18 pages.
U.S. Non-Final Office Action mailed on Sep. 27, 2019, for U.S. Appl. No. 29/562,795, filed Apr. 28, 2019, 6 pages.
Brazilian Office Action mailed Mar. 16, 2020 for Patent Application No. 112013022997-7, filed Mar. 8, 2012, six pages.
Canadian Notice of Allowance mailed Oct. 29, 2019, for Patent Application No. 2,998,920, filed Nov. 10, 2016, one page.
Chinese Notice of Allowance mailed Jan. 13, 2020, for Patent Application No. 2017-10785223.7, filed Mar. 8, 2012, six pages.
European Extended Search Report mailed Jan. 14, 2020, for Patent Application No. 17812362.6, filed Jun. 14, 2017, 8 pages.
Japanese Office Action mailed Jan. 10, 2020, for Japanese Patent Application No. 2018-516161, filed Nov. 10, 2016, five pages.
U.S. Ex Parte Quayle Action mailed Mar. 23, 2020, for U.S. Appl. No. 15/584,405, filed May 2, 2017, five pages.
U.S. Final Office Action mailed Feb. 7, 2020, for U.S. Appl. No. 15/343,038, filed Nov. 3, 2016, sixteen pages.
U.S. Notice of Allowance mailed Feb. 14, 2020, for U.S. Appl. No. 14/860,687, filed Sep. 21, 2015, eight pages.
U.S. Notice of Allowance mailed Feb. 14, 2020, for U.S. Appl. No. 15/343,034, filed Nov. 3, 2016, seven pages.
U.S. Notice of Allowance mailed Mar. 12, 2020, for U.S. Appl. No. 16/441,493, filed Jun. 14, 2019, 8 pages.
Office Action dated Jul. 6, 2020, directed to CA Application No. 3,009,419; 3 pages.
Notification to Pay Restoration Fee for Unity dated Apr. 7, 2020, directed to CN Application No. 201680066060.0, 2 pages.
First Office Action dated Jul. 2, 2020, directed to CN Application No. 201680066060.0; 30 pages.
Decision to Grant dated Jul. 18, 2019, directed to EP Application No. 09819758.5; 2 pages.
Office Action dated Sep. 16, 2020, directed to EP Application No. 16 186 321.2; 4 pages.
International Preliminary Report on Patentability mailed Aug. 22, 2019, directed to International Application No. PCT/CA2017/050564; 9 pages.
International Search Report mailed Oct. 24, 2017, directed to International Application No. PCT/CA2017/050564; 6 pages.
Extended European Search Report dated Oct. 14, 2020, directed to EP Application No. 17895908.6; 8 pages.
Invitation to Pay Additional Fees and, where Applicable, Protest Fee dated Jul. 4, 2017, directed to International Application No. PCT/CA2017/050564; 2 pages.
Decision to Grant a Patent dated Jun. 29, 2020, directed to JP Application No. 2018-516161; 6 pages.
Kolaman et al. "Amplitude Modulated Video Camera-Light Separation in Dynamic Scenes," 29th IEEE Conference on Computer Vision and Pattern Recognition (CVPR), Jun. 26-Jul. 1, 2016, Las Vegas, Nevada, USA; pp. 1-9.
Moore et al., U.S. Office Action dated Feb. 4, 2020, directed to U.S. Appl. No. 15/591,909; 13 pages.
Westwick et al., U.S. Office Action dated Aug. 27, 2020, directed to U.S. Appl. No. 15/343,038; 16 pages.

(56) References Cited

OTHER PUBLICATIONS

Murray et al., U.S. Office Action dated Apr. 3, 2020, directed to U.S. Appl. No. 16/746,539; 15 pages.
Murray et al., U.S. Office Action dated Aug. 31, 2020, directed to U.S. Appl. No. 16/746,539; 16 pages.
Murray et al., U.S. Ex Parte Quayle Action dated Jul. 23, 2020, directed to U.S. Appl. No. 29/724,647; 5 pages.
Murray et al., U.S. Ex Parte Quayle Action dated Jul. 23, 2020, directed to U.S. Appl. No. 29/724,650; 5 pages.
Murray et al., U.S. Ex Parte Quayle Action dated Jul. 23, 2020, directed to U.S. Appl. No. 29/724,651; 5 pages.
Fengler et al., U.S. Notice of Allowance and Fee(s) Due mailed May 19, 2020, directed to U.S. Appl. No. 15/584,405; 9 pages.
Moore et al., U.S. Office Action dated Aug. 6, 2019, directed to U.S. Appl. No. 15/591,909; 9 pages.
Fengler et al., U.S. Office Action dated May 5, 2020, directed to U.S. Appl. No. 15/623,100; 12 pages.
Fengler et al., U.S. Notice of Allowance and Fee(s) Due mailed Aug. 18, 2020, directed to U.S. Appl. No. 15/623,100; 7 pages.
Murray et al., U.S. Notice of Allowance and Fee(s) due mailed Jul. 13, 2020, directed to U.S. Appl. No. 29/562,795; 7 pages.
Moore et al., U.S. Restriction Requirement dated Jan. 17, 2019, directed to U.S. Appl. No. 15/591,909; 7 pages.
Written Opinion of the International Searching Authority mailed Oct. 24, 2017, directed to International Application No. PCT/CA2017/050564; 7 pages.
Intention to Grant dated May 17, 2021, directed to EP Application No. 16 186 321.2; 7 pages.
Moore et al., U.S. Notice of Allowance and Fee(s) due mailed Mar. 5, 2019, directed to U.S. Appl. No. 15/348,664; 10 pages.
Moore et al., U.S. Office Action dated Nov. 9, 2021, directed to U.S. Appl. No. 16/933,900; 14 pages.
Moore et al., U.S. Office Action dated Oct. 17, 2019, directed to U.S. Appl. No. 16/441,493; 8 pages.
Notification to Grant Patent Right for Invention dated Mar. 31, 2021, directed to CN Application No. 201680066060.0; 8 pages.
Office Action dated Jun. 16, 2021, directed to EP Application No. 16 863 277.6; 5 pages.
First Office Action mailed Jul. 30, 2021, directed to JP Application No. 2020-128414; 8 pages.
Fengler et al., U.S. Advisory Action dated Dec. 20, 2019, directed to U.S. Appl. No. 15/416,876; 5 pages.
Fengler et al., U.S. Advisory Action dated Nov. 2, 2020, directed to U.S. Appl. No. 15/416,876; 5 pages.
Fengler et al., U.S. Notice of Allowance and Fee(s) Due mailed Dec. 4, 2020, directed to U.S. Appl. No. 15/416,876; 9 pages.
Fengler et al., U.S. Restriction Requirement dated Oct. 13, 2021, directed to U.S. Appl. No. 16/951,684; 7 pages.
Office Action dated Nov. 18, 2020, directed to CA Application No. 3,027,592; 3 pages.
U.S. Notice of Allowance dated Oct. 25, 2018 for U.S. Appl. No. 29/588,898, filed Dec. 23, 2016, 14 pages.
Moore et al., U.S. Office Action dated Nov. 19, 2020, directed to U.S. Appl. No. 15/591,909; 13 pages.
Moore et al., U.S. Advisory Action dated May 19, 2020, directed to U.S. Appl. No. 15/591,909; 3 pages.
Moore et al., U.S. Notice of Allowance and Fee(s) due mailed Jun. 1, 2021, directed to U.S. Appl. No. 15/591,909; 6 pages.
Murray et al., U.S. Notice of Allowance and Fee(s) Due mailed Dec. 22, 2020, directed to U.S. Appl. No. 16/746,539; 7 pages.
Office Action dated Oct. 1, 2021, directed to EP Application No. 17 895 908.6; 4 pages.
Notice of Reasons for Refusal dated Feb. 12, 2021, directed to JP Application No. 2019-540067; 13 pages.
Decision to Grant a Patent mailed Jul. 16, 2021, directed to JP Application No. 2019-540067; 6 pages.
U.S. Non-Final Office Action mailed on Apr. 3, 2019 for U.S. Appl. No. 15/416,876, filed Jan. 26, 2017, thirteen pages.
Fengler et al., U.S. Office Action dated Jul. 15, 2020, directed to U.S. Appl. No. 15/416,876; 20 pages.

U.S. Final Office Action mailed on Jul. 25, 2019, directed to U.S. Appl. No. 15/416,876; 13 pages.
Decision of Refusal dated Nov. 11, 2022, directed to JP Application No. 2020-128414; 5 pages.
Decision to Grant a Patent dated Jun. 23, 2023, directed to JP Application No. 2021-132340; 6 pages.
Extended European Search Report dated Sep. 18, 2023, directed to EP Application No. 23174549.8; 11 pages.
Extended European Search Report dated Feb. 10, 2023, directed to EP Application No. 22187529.7; 10 pages.
Fengler et al., U.S. Notice of Allowance and Fee(s) Due mailed Dec. 2, 2021, directed to U.S. Appl. No. 17/234,461; 8 pages.
Fengler et al., U.S. Notice of Allowance and Fee(s) Due mailed Jan. 10, 2024, directed to U.S. Appl. No. 17/658,815; 7 pages.
Fengler et al., U.S. Notice of Allowance and Fee(s) Due mailed May 1, 2023, directed to U.S. Appl. No. 16/951,684; 7 pages.
Fengler et al., U.S. Office Action dated Aug. 25, 2023, directed to U.S. Appl. No. 17/658,815; 14 pages.
Fengler et al., U.S. Office Action dated Feb. 24, 2022, directed to U.S. Appl. No. 16/951,684; 12 pages.
Fengler et al., U.S. Office Action dated Jan. 12, 2023, directed to U.S. Appl. No. 17/658,815; 14 pages.
Fengler et al., U.S. Office Action dated Sep. 14, 2022, directed to U.S. Appl. No. 16/951,684; 14 pages.
First Office Action dated Jun. 6, 2024, directed to CN Application No. 202110658728.3; 17 pages.
Intention to Grant dated Dec. 6, 2022, directed to EP Application No. 17 895 908.6; 5 pages.
Intention to Grant dated Feb. 25, 2022, directed to EP Application No. 17 743 524.5; 7 pages.
Intention to Grant dated Mar. 18, 2024, directed to EP Application No. 16 863 277.6; 7 pages.
Intention to Grant dated May 10, 2024, directed to EP Application No. 18 178 620.3; 8 pages.
Intention to Grant dated Oct. 30, 2023, directed to EP Application No. 16 863 277.6; 8 pages.
Kim et al., (Aug. 5, 2014). "Multi-spectral imaging with infrared sensitive organic light emitting diode," Scientific Reports 4(5946): 1-5.
Moore et al., U.S. Advisory Action dated Jan. 5, 2024, directed to U.S. Appl. No. 17/493,799; 5 pages.
Moore et al., U.S. Advisory Action dated Oct. 11, 2022, directed to U.S. Appl. No. 16/933,900; 3 pages.
Moore et al., U.S. Notice of Allowance and Fee(s) due mailed Feb. 29, 2024, directed to U.S. Appl. No. 17/493,799; 5 pages.
Moore et al., U.S. Office Action dated Apr. 13, 2023, directed to U.S. Appl. No. 17/493,799; 13 pages.
Moore et al., U.S. Office Action dated Aug. 25, 2023, directed to U.S. Appl. No. 17/493,799; 13 pages.
Moore et al., U.S. Office Action dated Dec. 13, 2022, directed to U.S. Appl. No. 16/933,900; 15 pages.
Moore et al., U.S. Office Action dated Jun. 16, 2023, directed to U.S. Appl. No. 16/933,900; 14 pages.
Moore et al., U.S. Office Action dated May 16, 2022, directed to U.S. Appl. No. 16/933,900; 13 pages.
Moore et al., U.S. Restriction Requirement dated Jan. 10, 2023, directed to U.S. Appl. No. 17/493,799; 5 pages.
Moore et al., U.S. Restriction Requirement dated May 3, 2018, directed to U.S. Appl. No. 15/348,664; 5 pages.
Notice of Filing Divisional Application (s) dated Oct. 27, 2023, directed to CN Application No. 202110658728.3; 4 pages.
Notice of Reasons for Refusal dated Apr. 1, 2022, directed to JP Application No. 2020-128414; 11 pages.
Notice of Reasons for Refusal dated Jan. 12, 2024, directed to JP Application No. 2020-128414; 6 pages.
Notice of Reasons for Refusal dated Mar. 4, 2024, directed to JP Application No. 2023-037764; 12 pages.
Notice of Reasons for Refusal dated Sep. 9, 2022, directed to JP Application No. 2021-132340; 8 pages.
Office Action dated Dec. 1, 2022, directed to EP Application No. 16 863 277.6; 6 pages.
Office Action dated Feb. 25, 2022, directed to EP Application No. 18 178 620.3; 4 pages.

(56) References Cited

OTHER PUBLICATIONS

Office Action dated Jun. 7, 2022, directed to EP Application No. 17 812 362.6; 5 pages.

Trial and Appeal Decision dated Jun. 10, 2024, directed to JP Application No. 2020-128414; 4 pages.

Westwick et al., U.S. Notice of Allowance and Fee(s) Due mailed May 12, 2023, directed to U.S. Appl. No. 17/243,002; 7 pages.

Westwick et al., U.S. Office Action dated Dec. 16, 2021, directed to U.S. Appl. No. 17/243,002; 19 pages.

Westwick et al., U.S. Office Action dated May 18, 2022, directed to U.S. Appl. No. 17/243,002; 13 pages.

Westwick et al., U.S. Office Action dated Nov. 16, 2022, directed to U.S. Appl. No. 17/243,002; 11 pages.

Notice of Reasons for Refusal dated Jun. 24, 2024, directed to JP Application No. 2023-118437; 20 pages.

Fengler et al., U.S. Restriction Requirement dated Oct. 17, 2018, directed to U.S. Appl. No. 15/623,100; 7 pages.

Fengler et al., U.S. Office Action dated Jan. 16, 2020, directed to U.S. Appl. No. 15/416,876, 13 pages.

Decision to Grant dated Apr. 28, 2023, directed to EP Application No. 17 895 908.6; 2 pages.

Decision to Grant dated Jul. 25, 2024, directed to EP Application No. 16 863 277.6; 2 pages.

Intention to Grant dated Sep. 26, 2024, directed to EP Application No. 18 178 620.3; 7 pages.

Second Office Action dated Oct. 28, 2024, directed to CN Application No. 202110658728.3; 13 pages.

Decision of Refusal dated Oct. 4, 2024, directed to JP Application No. 2023-037764; 6 pages.

Extended European Search Report dated Nov. 19, 2024, directed to EP Application No. 24195477.5; 11 pages.

Fengler et al., U.S. Restriction Requirement dated Nov. 29, 2024, directed to U.S. Appl. No. 18/364,462; 7 pages.

Decision of Refusal dated Jan. 24, 2025, directed to JP Application No. 2023-118437; 12 pages.

Fengler et al., U.S. Office Action dated Mar. 12, 2025, directed to U.S. Appl. No. 18/364,462; 21 pages.

Office Action dated Feb. 28, 2025, directed to EP Application No. 22 187 529.7; 4 pages.

Murray et al., U.S. Office Action dated Mar. 12, 2025, directed to U.S. Appl. No. 18/761,256; 12 pages.

Murray et al., U.S. Notice of Allowance and Fee(s) due mailed Jul. 3, 2025, directed to U.S. Appl. No. 18/761,256; 5 pages.

Office Action dated May 21, 2025, directed to EP Application No. 23174549.8; 5 pages.

Office Action dated Apr. 24, 2025, directed to EP Application No. 17 812 362.6; 3 pages.

Decision on Rejection dated Mar. 26, 2025, directed to CN Application No. 202110658728.3; 12 pages.

Fengler et al., U.S. Notice of Allowance and Fee(s) Due mailed Sep. 11, 2025, directed to U.S. Appl. No. 18/364,462; 7 pages.

Moore et al., U.S. Office Action dated Oct. 2, 2025, directed to U.S. Appl. No. 18/601,995; 12 pages.

Reconsideration Report by Examiner before Appeal dated Sep. 16, 2025, directed to JP Application No. 2023-118437; 8 pages.

* cited by examiner

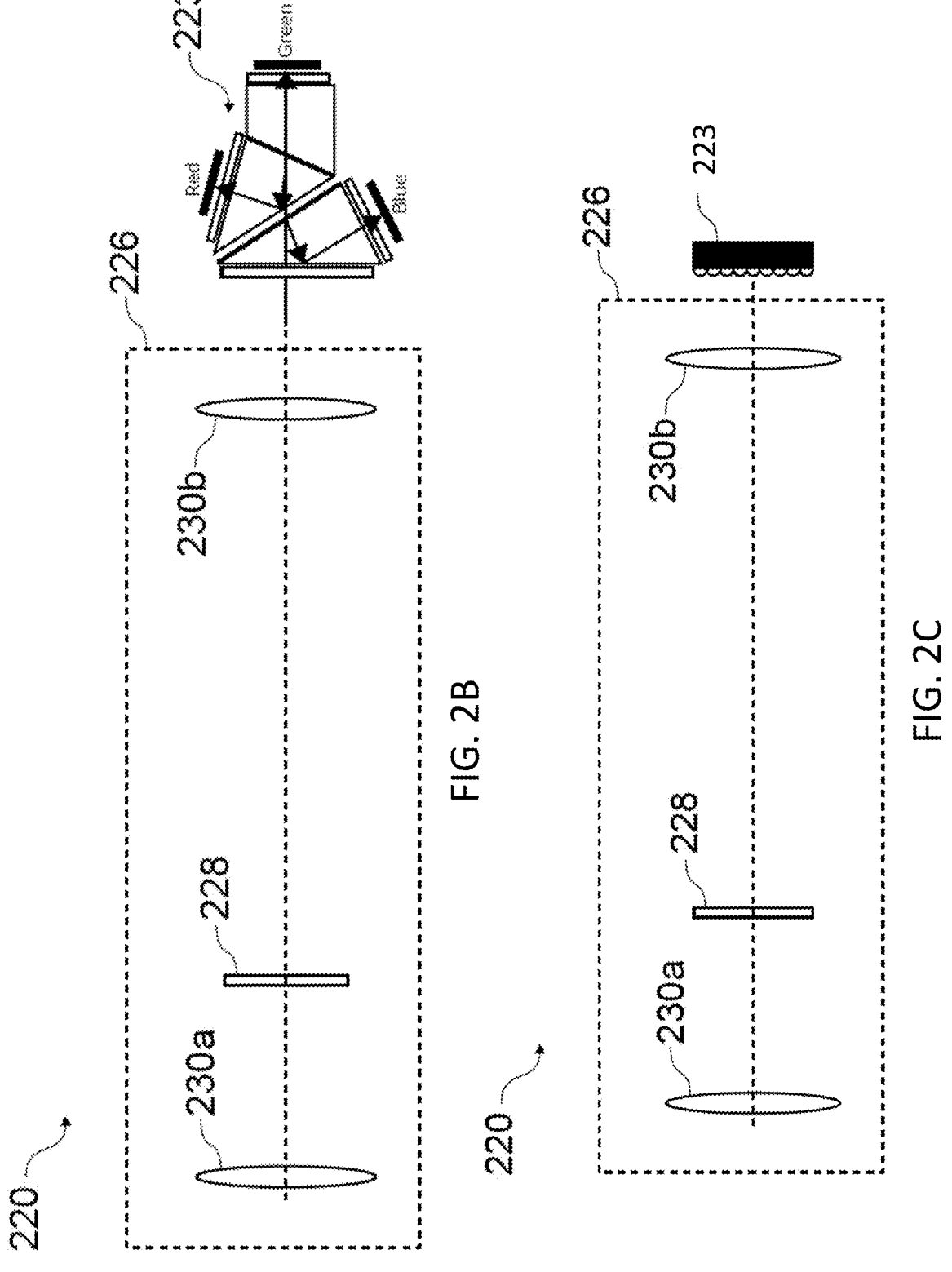

| Band | Fluorophore Examples | Ex λ (nm) | Em λ (nm) |
|------|----------------------|-----------|-----------|
| 1 | • Endogenous tissue fluorophores (collagen, elastin, NADH) <br> • 5-Aminolevulinic Acid (5-ALA) | ~405 | 530 - 630 |
| 2 | • Fluorescein <br> • Green Fluorescence Protein (GFP) <br> • Riboflavin | ~470 - 480 | ~520 |
| 3 | • Methylene Blue (MB) <br> • Porphysomes <br> • Cyanine dyes (Cathepsin-activated Cy5*, Cy5.5) | ~660 | ~690 -710 |
| 4 | • IRDye800CW <br> • CLR 1502* <br> • OTL38* | ~760 - 780 | ~790-800 |
| 5 | • Indocyanine Green (ICG) in blood | ~805 | ~830 |
| 6 | • IR1061 <br> • CH1100 | ~805 | ~1100 |
| 7 | • IR-PEG (organic nanoparticle) | ~750 - 810 | ~900 - 1150 |

* dye combined with targeting ligand

FIG. 3A

SYSTEMS AND METHODS FOR IMAGING USING A CONFIGURABLE PLATFORM

CROSS-REFERENCE TO RELATED APPLICATIONS

This application is a continuation of U.S. patent application Ser. No. 17/658,815, filed Apr. 11, 2022, which is a continuation of U.S. patent application Ser. No. 17/234,461, filed Apr. 19, 2021, now U.S. Pat. No. 11,298,024, which is a continuation of U.S. patent application Ser. No. 15/416, 876, filed Jan. 26, 2017, now U.S. Pat. No. 10,980,420, which claims priority to U.S. Provisional Application No. 62/354,611, filed Jun. 24, 2016, and U.S. Provisional Application No. 62/287,415, filed Jan. 26, 2016, each of which are hereby incorporated by reference in their entirety.

FIELD OF THE INVENTION

The present disclosure relates generally to medical imaging, and more particularly to the acquiring and processing of medical images for visualizing tissue of a subject.

BACKGROUND OF THE INVENTION

Many forms of intraoperative optical imaging are used in surgical applications, and such uses are continuing to expand. One area of particular growth involves imaging systems that excite and image fluorescence emitted by endogenous or exogenously introduced fluorophores. Fluorescence imaging capabilities have consequently been incorporated into a variety of highly specialized imaging equipment tailored for particular surgical applications, such as, for example, surgical microscopes, laparoscopy towers, vision systems for surgical robots and stand-alone wide field (e.g. laparotomy) imaging systems. However, because hospitals and other healthcare institutions desire fluorescence imaging capabilities for a broad range of surgeries, they must make a substantial investment in purchasing many specialized imaging devices to serve their varied needs.

Some limitations of intraoperative fluorescence imaging devices that are configured for use in specific surgeries have been recognized by others, but previous attempts at generating an adequate solution have fallen short of the desired outcome. Typically, such attempts consist of adapting fluorescence imaging devices specifically designed for one type of surgery for use in another type of surgery (e.g., combining an endoscopic fluorescence system with an exoscope). However, because the original product architecture for such devices was established without consideration of the new surgical application, such attempted adaptation may result in an unacceptable compromise in performance, functionality and ergonomics.

Furthermore, many optical imaging devices appear to detect only a single fluorescence excitation and emission waveband, and consequently are limited to use with only the particular fluorophores utilizing that single excitation/emission waveband. Current optical imaging devices that are capable of detecting multiple fluorescence emission wavebands appear to require multiple cameras where each camera is dedicated to a particular emission waveband, and yet an additional camera if real time visible (white) light imaging functionality is desired. However, these devices are too large and cumbersome for use in many surgical applications.

Thus, systems and methods that provide fluorescence imaging across a broad range of surgical applications are desirable. Systems and methods that provide fluorescence imaging using multiple fluorescence excitation/emission wavebands are also desirable.

BRIEF SUMMARY OF THE INVENTION

Described here are variations of fluorescence imaging systems and methods for imaging an object, where the fluorescence imaging system has a configurable platform. Generally, one variation of a fluorescence imaging system may include a white light provider that emits white light. The imaging system may include an excitation light provider that emits excitation light in a plurality of non-overlapping excitation wavebands for causing the object to emit fluorescent light. The imaging system may include an interchangeable surgery-specific component that directs the white light and excitation light to the object and collects reflected white light and emitted fluorescent light from the object. The imaging system may include a filter that blocks substantially all light in the excitation wavebands and transmits at least a substantial portion of the reflected white light and fluorescent light. The imaging system may include an image sensor assembly that receives the transmitted reflected white light and the fluorescent light.

Generally, one variation of a fluorescence imaging system may include a white light provider that emits white light, an excitation light provider that emits excitation light in a plurality of non-overlapping excitation wavebands for causing the object to emit fluorescent light, an interchangeable surgery-specific component that directs the white light and excitation light to the object and collects reflected white light and emitted fluorescent light from the object, a filter that blocks substantially all light in the excitation wavebands and transmits at least a substantial portion of the reflected white light and fluorescent light, and an image sensor assembly that receives the transmitted reflected white light and the fluorescent light. In some variations of the systems described here, at least one of the excitation wavebands may be centered at about 405 nm, about 470-480 nm, about 660 nm, about 760-780 nm, about 805 nm, or about 750-810 nm.

In some variations of the systems described here, the excitation light provider may include at least three excitation light sources. In some of these variations, the excitation light provider may include at least four excitation light sources. In some of these variations, the excitation light provider may include at least five excitation light sources. In some variations, the excitation light provider may include at least one solid state light source. In some of these variations, the excitation light provider may include a laser diode. In some of these variations, the excitation light provider may include an LED. In some variations, the excitation light provider may include a non-solid state light source. In some variations, at least a portion of the excitation light provider may be coupled to an optical filter that narrows the spectrum of light emitted from the excitation light provider.

In some variations, the white light provider may include a solid state light source. In some of these variations, the white light provider may include discrete color solid state light sources. In some of these variations, the white light provider may include red, green, and blue LEDs or laser diodes. In some variations, the white light provider may include white LEDs. In some variations, the white light provider may include a non-solid state light source.

In some variations, the filter may have an optical density of at least 4 for blocking substantially all light in the excitation wavebands. In some variations, the filter may transmit at least about 90% of the reflected white light and the fluorescent light. In some variations, the filter may have a transition region of less than about 10 nm between substantially blocked wavelengths and substantially transmitted wavelengths. In some variations, the filter may be integrated with the image sensor assembly. In some variations, the filter may be integrated with the surgery-specific component. In some variations, the filter may be configured to couple to the image sensor assembly and to the surgery-specific component.

In some variations, the image sensor assembly may include a single image sensor. In some of these variations, the image sensor may include a color image sensor. In some of these variations, the image sensor assembly may include a color filter array coupled to pixels of the color image sensor. In some variations, the image sensor may be a monochrome image sensor. In some variations, the image sensor assembly may include a plurality of image sensors. In some variations, the image sensors may be coupled to at least one spectral splitter. In some variations, the image sensor assembly may include a solid state image sensor. In some of these variations, the image sensor assembly may include CMOS, CCD, or CID technology which may or may not further include indium-gallium-arsenide or black silicon material.

In some variations, the surgery-specific component, such as an interchangeable surgery-specific component, may be configured for microsurgery. In some variations, the interchangeable surgery-specific component may be configured for laparoscopic or endoscopic surgery. In some variations, the interchangeable surgery-specific component may be configured to provide wide field illumination. In some variations, the interchangeable surgery-specific component may be configured for stereoscopic laparoscopy. In some variations, the surgery-specific component may be designed for at least two different surgical applications.

In some variations, the system may include at least one image processor that receives image signals from the image sensor assembly and processes the received image signals to generate images from the received image signals. In some variations, the system may include at least one controller that controls the system to selectively operate in a non-fluorescence mode, a fluorescence mode, and a combined non-fluorescence and fluorescence mode. In some of these variations, in the non-fluorescence mode, the controller may cause the white light provider to emit white light and the image processor may generate a white light image based on image signals associated with the reflected white light from the object. In some of these variations, in the fluorescence mode, the controller may cause the excitation light provider to emit excitation light and the image processor may generate a fluorescence emission image based on image signals associated with the fluorescent light from the object. In some of these variations, in the combined non-fluorescence and fluorescence mode, the controller may cause at least a portion of the white light or at least a portion of the excitation light to be pulsed. In some of these variations, the image processor may separate image signals from the image sensor assembly into a first set of image signals associated with the reflected white light and a second set of image signals associated with the fluorescent light, and the image processor may generate a white light image based on the first set of image signals and a fluorescence emission image based on the second set of image signals. In some variations, the system may include a display that displays at least one image generated from image signals from the image sensor assembly.

Also described here are variations of fluorescence imaging systems for imaging an object, where the fluorescence imaging system is multiplexed. Generally, one variation of a fluorescence imaging system may include a light source assembly including a white light provider that emits white light. The imaging system may include an excitation light provider that emits excitation light in a plurality of non-overlapping excitation wavebands for causing the object to emit fluorescent light. The imaging system may include at least one image sensor that receives reflected white light and emitted fluorescent light from the object. The imaging system may include an optical assembly located in the optical path between the object and the image sensor comprising a first optics region that projects the reflected white light as a white light image onto the image sensor, and a second optics region that reduces the image size of the fluorescent light, spectrally separates the fluorescent light, and projects the separated fluorescent light in fluorescent images onto different portions of the image sensor. The imaging system may include an image processor that electronically magnifies the fluorescence images.

Generally, one variation of a fluorescence imaging system may include a light source assembly including a white light provider that emits white light; an excitation light provider that emits excitation light in a plurality of non-overlapping excitation wavebands for causing the object to emit fluorescent light; at least one image sensor that receives reflected white light and emitted fluorescent light from the object; an optical assembly located in the optical path between the object and the image sensor comprising a first optics region that projects the reflected white light as a white light image onto the image sensor, and a second optics region that reduces the image size of the fluorescent light, spectrally separates the fluorescent light, and projects the separated fluorescent light in fluorescent images onto different portions of the image sensor; and an image processor that electronically magnifies the fluorescence images.

In some variations, at least one of the excitation wavebands may be centered at a wavelength falling substantially outside of the visible light spectrum (e.g., between about 450 nm and 650 nm). In some of these variations, at least one of the plurality of wavebands may be centered at about 670 nm, about 770 nm, or about 805 nm. In some of these variations, the excitation light provider may comprise a first excitation light source emitting excitation light centered at about 670 nm, a second excitation light source emitting excitation light centered at about 770 nm, and a third excitation light source emitting excitation light centered at about 805 nm. In some variations, at least one of the excitation wavebands may be centered at about 405 nm, or about 470 nm.

In some variations, the system may include a combining optical assembly coupled to the light source assembly, wherein the combining optical assembly combines the emitted white light and excitation light from the light source assembly into a single optical path. In some of these variations, the combining optical assembly may include at least one dichroic mirror. In some of these variations, the combining optical assembly may comprise optical fibers.

In some variations, the optical assembly may comprise a filter that blocks substantially all light in the excitation wavebands and transmits at least a substantial portion of reflected white light and fluorescent light from the object. In some variations, the optical assembly may comprise a beam splitter that separates the transmitted light into a first branch of reflected white light and a second branch of fluorescent light.

In some variations, the second optics region may comprise demagnification optics that reduce the image size of the fluorescent light. In some variations, the second optics region may comprise a beam splitter that spectrally separates the fluorescent light. In some variations, the beam splitter may be located in that optical path after the demagnification optics. In some variations, the beam splitter may spectrally separate the fluorescent light in paths corresponding to the excitation wavebands that generated the fluorescent light. In some variations, the second optics region may comprise an alignment component that makes the spectrally separated fluorescent light and the reflected white light follow the equivalent optical path. In some variations, the beam splitter may spectrally separate the fluorescent light into four branches of fluorescent light that are projected as four fluorescent images onto quadrants of the image sensor. In some of these variations, the ratio of magnification level of the white light image to the magnification level of each of the fluorescent light images projected onto the image sensor may be about 2:1. In some of these variations, the image processor may electronically magnify the fluorescent images by a factor of about 2.

In some variations, the first optics region and the second optics region may be different regions in a prism. In some variations, the image processor may spatially co-register the white light image and magnified fluorescent images. In some variations, the light source assembly may comprise at least one solid state light source. In some variations, the image sensor may have a spatial resolution of at least about 4K.

In some variations, the system may include a display that displays at least one image generated from image signals from the image sensor assembly.

Generally, one variation of a method for fluorescence imaging of an object may include emitting white light, emitting excitation light in a plurality of excitation wavebands for causing the object to emit fluorescent light, directing the white light and excitation light to the object, collecting reflected white light and emitted fluorescent light from the object, blocking light in the excitation wavebands and transmitting at least a portion of the reflected white light and fluorescent light, and receiving the transmitted reflected white light and fluorescent light on an image sensor assembly. In some variations, at least one of the excitation wavebands may be centered at about 405 nm, about 470-480 nm, about 660 nm, about 760-780 nm, about 805 nm, or about 750-810 nm.

In some variations, the excitation light may be emitted by an excitation light provider that comprises at least three excitation light sources.

In some variations, the excitation light may be emitted by an excitation light provider that comprises at least four excitation light sources. In some variations, the excitation light may be emitted by an excitation light provider that comprises at least five excitation light sources. In some variations, the excitation light may be emitted by an excitation light provider that comprises at least one solid state light source. In some variations, the excitation light may be emitted by an excitation light provider that comprises a laser diode. In some variations, the excitation light may be emitted by an excitation light provider that comprises an LED. In some variations, the excitation light may be emitted by an excitation light provider that comprises a non-solid state light source. In some variations, the excitation light may be emitted by an excitation light provider in which at least a portion of the excitation light provider is coupled to an optical filter that narrows the spectrum of light emitted from the excitation light provider. In some variations, the white light may be emitted by a white light provider that comprises a solid state light source. In some variations, the white light may be emitted by a white light provider that comprises discrete color solid state light sources.

In some variations, the white light may be emitted by a white light provider that comprises red, green, and blue LEDs or laser diodes. In some variations, the white light may be emitted by a white light provider that comprises white LEDs. In some variations, the white light may be emitted by a white light provider that comprises a non-solid state light source.

In some variations, blocking light in the excitation wavebands and transmitting at least a portion of the reflected white light and fluorescent light may be performed by a filter that has an optical density of at least 4 for blocking substantially all light in the excitation wavebands. In some variations, blocking light in the excitation wavebands and transmitting at least a portion of the reflected white light and fluorescent light may be performed by a filter that transmits at least 90% of the reflected white light and the fluorescent light. In some variations, blocking light in the excitation wavebands and transmitting at least a portion of the reflected white light and fluorescent light may be performed by a filter that has a transition region of less than 10 nm between substantially blocked wavelengths and substantially transmitted wavelengths.

In some variations, blocking light in the excitation wavebands and transmitting at least a portion of the reflected white light and fluorescent light may be performed by a filter that is integrated with the image sensor assembly. In some variations, blocking light in the excitation wavebands and transmitting at least a portion of the reflected white light and fluorescent light may be performed by a filter that is integrated with the interchangeable component.

In some variations, blocking light in the excitation wavebands and transmitting at least a portion of the reflected white light and fluorescent light may be performed by a filter that is configured to couple to the image sensor assembly and to the interchangeable component.

In some variations, the image sensor assembly may include a single image sensor. In some variations, the image sensor may be a color image sensor. In some variations, the image sensor assembly may comprise a color filter array coupled to pixels of the color image sensor. In some variations, the image sensor may be a monochrome image sensor. In some variations, the image sensor assembly may include a plurality of image sensors. In some variations, the image sensors may be coupled to at least one spectral splitter. In some variations, the image sensor assembly may include a solid state image sensor. In some variations, the image sensor assembly may include CMOS, CCD, or CID technology.

In some variations, the image sensor assembly may include indium-gallium-arsenide or black silicon material. In some variations, directing the white light and excitation light to the object and collecting reflected white light and emitted fluorescent light from the object may be performed by an interchangeable component. In some variations, the interchangeable component may be configured for microsurgery. In some variations, the interchangeable component may be configured for laparoscopic or endoscopic surgery. In some variations, the interchangeable component may be configured to provide wide field illumination. In some variations, the interchangeable component may be configured for stereoscopic laparoscopy. In some variations, the interchangeable component may be configured for robotic surgery. In some variations, the method may further include receiving image signals from the image sensor assembly and processing the received image signals to generate images from the received image signals.

In some variations, the method may further include selectively operating in a non-fluorescence mode, a fluorescence mode, or a combined non-fluorescence and fluorescence mode. In some variations, the method may further include while in the non-fluorescence mode, emitting white light and the generating a white light image based on image signals associated with the reflected white light from the object. In some variations, the method may further include while in the fluorescence mode, emitting excitation light and generating a fluorescence emission image based on image signals associated with the fluorescent light from the object. In some variations, the method may further include while in the combined non-fluorescence and fluorescence mode, pulsing at least a portion of the white light or at least a portion of the excitation light.

In some variations, the method may further include while in the combined non-fluorescence and fluorescence mode, temporally multiplexing at least a portion of the white light and/or at least a portion of the excitation light. In some variations, the method may further include separating image signals from the image sensor assembly into a first set of image signals associated with the reflected white light and a second set of image signals associated with the fluorescent light, and generating a white light image based on the first set of image signals and a fluorescence emission image based on the second set of image signals. In some variations, the method may further include displaying at least one image generated from image signals from the image sensor assembly. In some variations, the reflected white light and the fluorescent light received at the image sensor may be temporally multiplexed, spatially multiplexed, or both temporally multiplexed and spatially multiplexed.

Generally, one variation of a method for fluorescence imaging of an object includes emitting white light, emitting excitation light in a plurality of excitation wavebands, causing the object to emit fluorescent light, receiving reflected white light and emitted fluorescent light from the object on at least one image sensor, feeding at least part of the reflected light through an optical assembly located in an optical path between the object and the image sensor, wherein: a first optics region of the optical assembly projects reflected white light as a white light image onto the image sensor, and a second optics region reduces the image size of the fluorescent light, spectrally separates the fluorescent light, and projects the separated fluorescent light as fluorescence images onto different portions of the image sensor.

In some variations, at least one of the excitation wavebands may be centered at a wavelength falling outside of the visible light spectrum. In some variations, at least one of the plurality of excitation wavebands may be centered at about 670 nm, about 770 nm, or about 805 nm. In some variations, the excitation light may be emitted by an excitation light provider that comprises a first excitation light source emitting excitation light centered at about 670 nm, a second excitation light source emitting excitation light centered at about 770 nm, and a third excitation light source emitting excitation light centered at about 805 nm. In some variations, at least one of the excitation wavebands may be centered at about 405 nm, or about 470 nm. In some variations, the method may further include combining the emitted white light and excitation light from the light source assembly into a single optical path.

In some variations, the emitted white light and excitation light may be combined by a combining optical assembly that comprises at least one dichroic mirror. In some variations, the emitted white light and excitation light may be combined by a combining optical assembly that comprises optical fibers. In some variations, the optical assembly may include a filter that blocks light in the excitation wavebands and transmits at least a portion of reflected white light and fluorescent light from the object. In some variations, the optical assembly may include a beam splitter that separates the transmitted light into a first branch of reflected white light and a second branch of fluorescent light.

In some variations, the second optics region may include demagnification optics that reduce the image size of the fluorescent light. In some variations, the second optics region may include a beam splitter that spectrally separates the fluorescent light. In some variations, the beam splitter may be located in that optical path after the demagnification optics. In some variations, the beam splitter may spectrally separate the fluorescent light in paths corresponding to the excitation wavebands that generated the fluorescent light.

In some variations, the second optics region may include an alignment component that makes the spectrally separated fluorescent light and the reflected white light follow the same optical path. In some variations, the beam splitter may spectrally separate the fluorescent light into four branches of fluorescent light that are projected as four fluorescent images onto quadrants of the image sensor. In some variations, the ratio of magnification level of the white light image to the magnification level of each of the fluorescent light images projected onto the image sensor may be about 2:1. In some variations, the method may further include an image processor that electronically magnifies the fluorescence images. In some variations, the fluorescent images may be electronically magnified by a factor of about 2.

In some variations, the method may further include spatially co-registering the white light image and magnified fluorescent images. In some variations, the first optics region and the second optics region may be different regions in a prism. In some variations, the white light may be emitted by a light source assembly that comprises at least one solid state light source. In some variations, the image sensor may have a spatial resolution of at least about 4K. In some variations, the method may further include displaying at least one image generated from image signals from the image sensor assembly. In some variations, the method may further include temporally multiplexing at least a portion of the white light and/or at least a portion of the excitation light. In some variations, the method may further include electronically magnifying at least some of the fluorescence images.

Generally, one variation of a kit for imaging an object may include any of the systems described herein or any one of the methods described herein and a fluorescence imaging agent.

Generally, one variation of a fluorescence imaging agent may include that for use in any of the systems described herein, any of the methods described herein or any of the kits described herein. In some variations, imaging an object may include imaging an object during blood flow imaging, tissue perfusion imaging, lymphatic imaging, or a combination thereof. In some variations, blood flow imaging, tissue perfusion imaging, and/or lymphatic imaging may include blood flow imaging, tissue perfusion imaging, and/or lymphatic imaging during an invasive surgical procedure, a minimally invasive surgical procedure, or during a non-invasive surgical procedure. In some variations, the invasive surgical procedure may include a cardiac-related surgical procedure or a reconstructive surgical procedure. In some variations, the cardiac-related surgical procedure may include a cardiac coronary artery bypass graft (CABG)

procedure. In some variations, the CABG procedure may be on pump or off pump. In some variations, the non-invasive surgical procedure may include a wound care procedure. In some variations, the lymphatic imaging may include identification of a lymph node, lymph node drainage, lymphatic mapping, or a combination thereof. In some variations, the lymphatic imaging may relate to the female reproductive system.

In some variations, any of the methods, systems, or kits described herein may be used for lymphatic imaging. In some variations, any of the methods, systems, or kits described herein may be used for blood flow imaging, tissue perfusion imaging, or a combination thereof.

It will be appreciated that any one or more of the above variations, aspects, features and options, including variations, aspects, features and options of the fluorescence imaging systems, methods and kits can be combined.

BRIEF DESCRIPTION OF THE DRAWINGS

FIGS. 2B and 2C are illustrative depictions of exemplary variations of an image acquisition module in a fluorescence imaging system.

FIG. 3A is a table summarizing exemplary fluorescence excitation/emission wavebands and exemplary fluorophores (imaging agents).

DETAILED DESCRIPTION OF THE INVENTION

Figure 1:
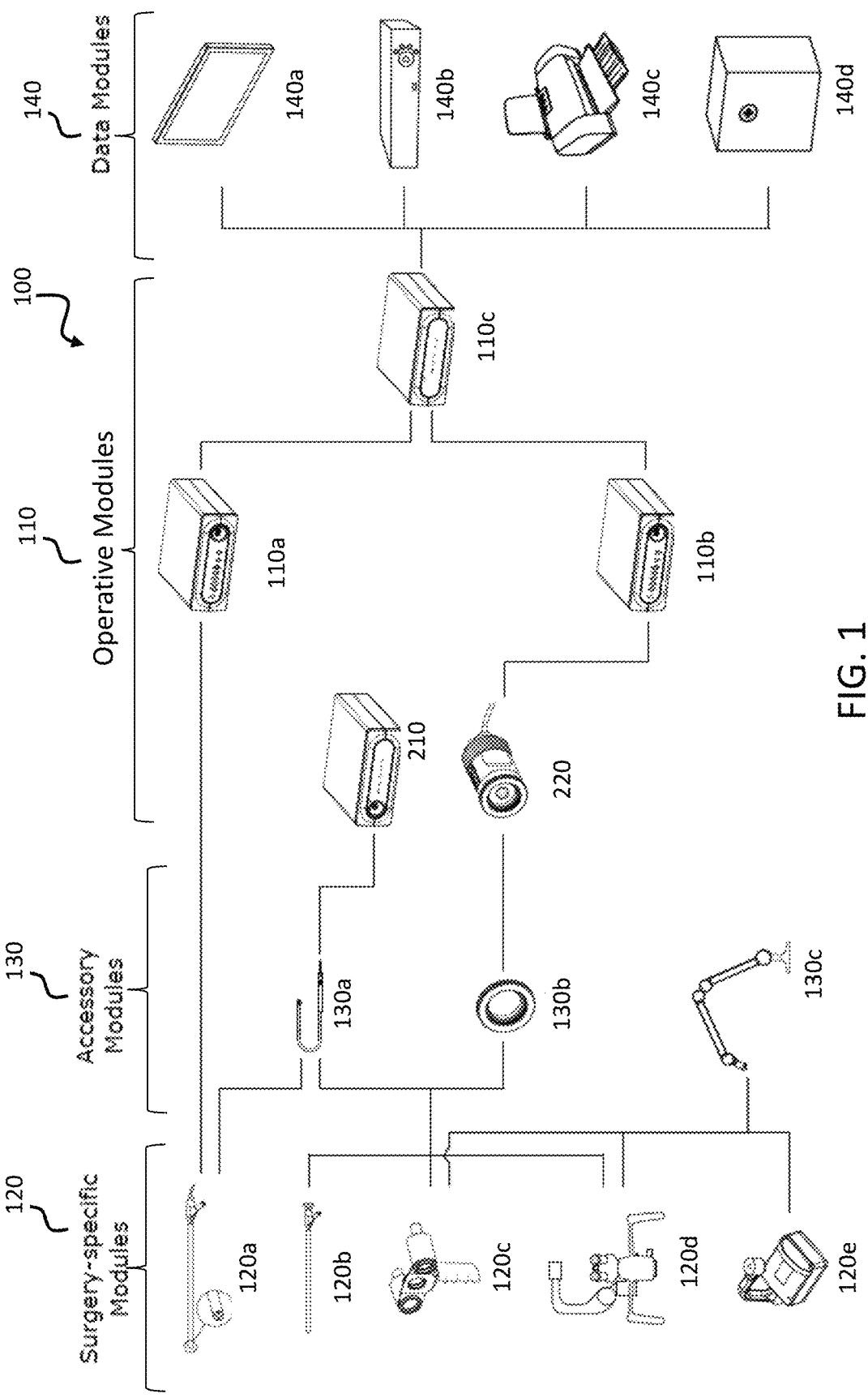
FIG. 1 is an illustrative schematic of a fluorescence imaging system with a configurable platform.

Reference will now be made in detail to implementations and variations of the invention, examples of which are illustrated in the accompanying drawings. Various fluorescence imaging systems, methods, imaging agents, and kits are described herein. Although at least two variations of imaging systems, methods (e.g., fluorescence imaging system and method with a configurable platform and multiplexed fluorescence imaging system and method), imaging agents, and kits are described, other variations of fluorescence imaging systems, methods, imaging agents, and kits may include aspects of the systems, methods, imaging agents, and kits described herein combined in any suitable manner having combinations of all or some of the aspects described.

The various systems and methods may be used for imaging an object. The object may, for example, include tissue (e.g., tissue having one or more endogenous or exogenously-introduced fluorophores), but may additionally or alternatively include any suitable substance or material to be imaged. In some variations, the systems and methods may employ a fluorescence imaging agent such as, for example, indocyanine green (ICG) dye (but other suitable imaging agents may be employed). ICG, when administered to the subject, binds with blood proteins and circulates with the blood in the tissue.

In some variations, the fluorescence imaging agent (e.g., ICG) may be administered to the subject as a bolus injection, in a suitable concentration for imaging. In some variations where the method is performed to assess tissue perfusion, the fluorescence imaging agent may be administered to the subject by injection into a vein or artery of the subject such that the dye bolus circulates in the vasculature and traverses the microvasculature. In some variations in which multiple fluorescence imaging agents are used, such agents may be administered simultaneously (e.g., in a single bolus), or sequentially (e.g., in separate boluses). In some variations, the fluorescence imaging agent may be administered by a catheter. In some variations, the fluorescence imaging agent may be administered to the subject less than an hour in advance of performing the measurements for generating the time series of fluorescence images. For example, the fluorescence imaging agent may be administered to the subject less than 30 minutes in advance of the measurements. In other variations, the fluorescence imaging agent may be administered at least 30 seconds in advance of performing the measurements. In some variations, the fluorescence imaging agent may be administered contemporaneously with performing the measurements.

In some variations, the fluorescence imaging agent may be administered in various concentrations to achieve a desired circulating concentration in the blood. For example, in some variations for tissue perfusion assessment where the fluorescence imaging agent is ICG, the fluorescence imaging agent may be administered at a concentration of about 2.5 mg/mL to achieve a circulating concentration of about 5 μM to about 10 μM in blood. In some variations, the upper concentration limit for the administration of the fluorescence imaging agent is the concentration at which the fluorescence imaging agent becomes clinically toxic in circulating blood, and the lower concentration limit is the limit for instruments used to acquire the time series of fluorescence images that detect the fluorescence imaging agent circulating in blood. In some variations, the upper concentration limit for the administration of the fluorescence imaging agent is the concentration at which the fluorescence imaging agent becomes self-quenching. For example, the circulating concentration of ICG may range from about 2 μM to about 10 mM.

Thus, in one aspect, the method may comprise administration of a fluorescence imaging agent or other imaging agent to the subject, and generation or acquisition of the time series of fluorescence images prior to processing the image data. In another aspect, the method may exclude any step of administering the fluorescence imaging agent or other imaging agent to the subject. For instance, the time series of fluorescence images may be based on measurements of autofluorescence response (e.g., native tissue autofluorescence or induced tissue autofluorescence), or measurements of a combination of autofluorescence and fluorescence arising from a fluorescence imaging agent.

In some variations, a suitable fluorescence imaging agent is an agent which can circulate with the blood (e.g., a fluorescence dye which can circulate with a component of the blood such as lipoproteins or serum plasma in the blood) and which fluoresces when exposed to appropriate excitation light energy. The fluorescence imaging agent may comprise a fluorescence dye, an analogue thereof, a derivative thereof, or a combination of these. A fluorescence dye may include any non-toxic fluorescence dye. In some variations, the fluorescence imaging agent optimally emits fluorescence in the near-infrared spectrum. In some variations, the fluorescence imaging agent is or comprises a tricarbocyanine dye such as, for example, indocyanine green (ICG). In other variations, the fluorescence imaging agent is or comprises fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, or a combination thereof, which is excitable using excitation light wavelengths appropriate to each imaging agent. In some variations, fluorescence imaging agents with long Stokes shifts (e.g., IR1061, CH1100, etc.) may be used. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations where some or all of the fluorescence is derived from autofluorescence, one or more of the fluorophores giving rise to the autofluorescence may be an endogenous tissue fluorophore (e.g., collagen, elastin, NADH, etc.), 5-aminolevulinic Acid (5-ALA), or a combination thereof.

In some variations, the fluorescence imaging agent may be provided as a lyophilized powder, solid, or liquid. The fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. Any diluent or carrier which will maintain the fluorescence imaging agent in solution may be used. As an example, ICG may be reconstituted with water. In some variations, once the fluorescence imaging agent is reconstituted, it may be mixed with additional diluents and carriers. In some variations, the fluorescence imaging agent may be conjugated to another molecule, (e.g., a protein, a peptide, an amino acid, a synthetic polymer, or a sugar) so as to enhance solubility, stability, imaging properties or a combination thereof. Additional buffering agents may optionally be added including Tris, HCl, NaOH, phosphate buffer, HEPES.

A person of skill in the art will appreciate that, although exemplary fluorescence imaging agents were described above in detail, other imaging agents may be used in connection with the systems, methods, techniques and kits described herein, depending on the optical imaging modality.

In some variations, the fluorescence imaging agent used in combination with the methods, systems and kits described herein may be used for blood flow imaging, tissue perfusion imaging, lymphatic imaging, or a combination thereof, which may performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the peri-wound, may be tracked over time with the application of the methods and systems. Examples of lymphatic imaging include identification of one or more lymph nodes, lymph node drainage, lymphatic mapping, or a combination thereof. In some variations such lymphatic imaging may relate to the female reproductive system (e.g., uterus, cervix, vulva).

In variations relating to cardiac applications, the imaging agent(s) (e.g., ICG alone or in combination with another imaging agent) may be injected intravenously through, for example, the central venous line, bypass pump and/or cardioplegia line to flow and/or perfuse the coronary vasculature, microvasculature and/or grafts. ICG may be administered as a dilute ICG/blood/saline solution down the grafted vessel such that the final concentration of ICG in the coronary artery is approximately the same or lower as would result from injection of about 2.5 mg (i.e., 1 ml of 2.5 mg/ml) into the central line or the bypass pump. The ICG may be prepared by dissolving, for example, 25 mg of the solid in 10 ml sterile aqueous solvent, which may be provided with the ICG by the manufacturer. One milliliter of the ICG solution may be mixed with 500 ml of sterile saline (e.g., by injecting 1 ml of ICG into a 500 ml bag of saline). Thirty milliliters of the dilute ICG/saline solution may be added to 10 ml of the subject's blood, which may be obtained in an aseptic manner from the central arterial line or the bypass pump. ICG in blood binds to plasma proteins and facilitates preventing leakage out of the blood vessels. Mixing of ICG with blood may be performed using standard sterile techniques within the sterile surgical field. Ten milliliters of the ICG/saline/blood mixture may be administered for each graft. Rather than administering ICG by injection through the wall of the graft using a needle, ICG may be administered by means of a syringe attached to the (open) proximal end of the graft. When the graft is harvested surgeons routinely attach an adaptor to the proximal end of the graft so that they can attach a saline filled syringe, seal off the distal end of the graft and inject saline down the graft, pressurizing the graft and thus assessing the integrity of the conduit (with respect to leaks, side branches etc.) prior to performing the first anastomosis.

Lymphatic mapping is an important part of effective surgical staging for cancers that spread through the lymphatic system (e.g., breast, gastric, gynecological cancers). Excision of multiple nodes from a particular node basin can lead to serious complications, including acute or chronic lymphedema, paresthesia, and/or seroma formation, when in fact, if the sentinel node is negative for metastasis, the surrounding nodes will most likely also be negative. Identification of the tumor draining lymph nodes (LN) has become an important step for staging cancers that spread through the lymphatic system in breast cancer surgery, for example. LN mapping involves the use of dyes and/or radiotracers to identify the LNs either for biopsy or resection and subsequent pathological assessment for metastasis. The goal of lymphadenectomy at the time of surgical staging is to identify and remove the LNs that are at high risk for local spread of the cancer. Sentinel lymph node (SLN) mapping has emerged as an effective surgical strategy in the treatment of breast cancer. It is generally based on the concept that metastasis (spread of cancer to the axillary LNs), if present, should be located in the SLN, which is defined in the art as the first LN or group of nodes to which cancer cells are most likely to spread from a primary tumor. If the SLN is negative for metastasis, then the surrounding secondary and tertiary LN should also be negative. The primary benefit of SLN mapping is to reduce the number of subjects who receive traditional partial or complete lymphadenectomy and thus reduce the number of subjects who suffer from the associated morbidities such as lymphedema and lymphocysts.

The current standard of care for SLN mapping involves injection of a tracer that identifies the lymphatic drainage pathway from the primary tumor. The tracers used may be radioisotopes (e.g. Technetium-99 or Tc-99m) for intraoperative localization with a gamma probe. The radioactive tracer technique (known as scintigraphy) is limited to hospitals with access to radioisotopes, requires involvement of a nuclear physician, and does not provide real-time visual guidance. A colored dye, isosulfan blue, has also been used, however this dye cannot be seen through skin and fatty tissue. In addition, blue staining results in tattooing of the breast lasting several months, skin necrosis can occur with subdermal injections, and allergic reactions with rare anaphylaxis have also been reported. Severe anaphylactic reactions have occurred after injection of isosulfan blue (approximately 2% of patients). Manifestations include respiratory distress, shock, angioedema, urticaria and pruritus. Reactions are more likely to occur in subjects with a history of bronchial asthma, or subjects with allergies or drug reactions to triphenylmethane dyes. Isosulfan blue is known to interfere with measurements of oxygen saturation by pulse oximetry and methemoglobin by gas analyzer. The use of isosulfan blue may result in transient or long-term (tattooing) blue coloration.

In contrast, fluorescence imaging in accordance with the various embodiments for use in SLN visualization, mapping, facilitates direct real-time visual identification of a LN and/or the afferent lymphatic channel intraoperatively, facilitates high-resolution optical guidance in real-time through skin and fatty tissue, and facilitates visualization of blood flow, tissue perfusion or a combination thereof.

In some variations, visualization, classification or both of lymph nodes during fluorescence imaging may be based on imaging of one or more imaging agents, which may be further based on visualization and/or classification with a gamma probe (e.g., Technetium Tc-99m is a clear, colorless aqueous solution and is typically injected into the periareolar area as per standard care), another conventionally used colored imaging agent (isosulfan blue), and/or other assessment such as, for example, histology. The breast of a subject may be injected, for example, twice with about 1% isosulfan blue (for comparison purposes) and twice with an ICG solution having a concentration of about 2.5 mg/ml. The injection of isosulfan blue may precede the injection of ICG or vice versa. For example, using a TB syringe and a 30 G needle, the subject under anesthesia may be injected with 0.4 ml (0.2 ml at each site) of isosulfan blue in the periareolar area of the breast. For the right breast, the subject may be injected at 12 and 9 o'clock positions and for the left breast at 12 and 3 o'clock positions. The total dose of intradermal injection of isosulfan blue into each breast may be about 4.0 mg (0.4 ml of 1% solution: 10 mg/ml). In another exemplary variation, the subject may receive an ICG injection first followed by isosulfan blue (for comparison). One 25 mg vial of ICG may be reconstituted with 10 ml sterile water for injection to yield a 2.5 mg/ml solution immediately prior to ICG administration. Using a TB syringe and a 30G needle, for example, the subject may be injected with about 0.1 ml of ICG (0.05 ml at each site) in the periareolar area of the breast (for the right breast, the injection may be performed at 12 and 9 o'clock positions and for the left breast at 12 and 3 o'clock positions). The total dose of intradermal injection of ICG into each breast may be about 0.25 mg (0.1 ml of 2.5 mg/ml solution) per breast. ICG may be injected, for example, at a rate of 5 to 10 seconds per injection. When ICG is injected intradermally, the protein binding properties of ICG cause it to be rapidly taken up by the lymph and moved through the conducting vessels to the LN. In some variations, the ICG may be provided in the form of a sterile lyophilized powder containing 25 mg ICG with no more than 5% sodium iodide. The ICG may be packaged with aqueous solvent consisting of sterile water for injection, which is used to reconstitute the ICG. In some variations the ICG dose (mg) in breast cancer sentinel lymphatic mapping may range from about 0.5 mg to about 10 mg depending on the route of administration. In some variations, the ICG does may be about 0.6 mg to about 0.75 mg, about 0.75 mg to about 5 mg, about 5 mg to about 10 mg. The route of administration may be for example subdermal, intradermal (e.g., into the periareolar region), subareolar, skin overlaying the tumor, intradermal in the areola closest to tumor, subdermal into areola, intradermal above the tumor, periareolar over the whole breast, or a combination thereof. The NIR fluorescent positive LNs (e.g., using ICG) may be represented as a black and white NIR fluorescence image(s) for example and/or as a full or partial color (white light) image, full or partial desaturated white light image, an enhanced colored image, an overlay (e.g., fluorescence with any other image), a composite image (e.g., fluorescence incorporated into another image) which may have various colors, various levels of desaturation or various ranges of a color to highlight/visualize certain features of interest. Processing of the images may be further performed for further visualization and/or other analysis (e.g., quantification). The lymph nodes and lymphatic vessels may be visualized (e.g., intraoperatively, in real time) using fluorescence imaging systems and methods according to the various embodiments for ICG and SLNs alone or in combination with a gamma probe (Tc-99m) according to American Society of Breast Surgeons (ASBrS) practice guidelines for SLN biopsy in breast cancer patients. Fluorescence imaging for LNs may begin from the site of injection by tracing the lymphatic channels leading to the LNs in the axilla. Once the visual images of LNs are identified, LN mapping and identification of LNs may be done through incised skin, LN mapping may be performed until ICG visualized nodes are identified. For comparison, mapping with isosulfan blue may be performed until 'blue' nodes are identified. LNs identified with ICG alone or in combination with another imaging technique (e.g., isosulfan blue, and/or Tc-99m) may be labeled to be excised. Subjects of the above methods may have various stages of breast cancer (e.g., IA, IB, IIA).

In some variations, such as for example, in gynecological cancers (e.g., uterine, endometrial, vulvar and cervical malignancies), ICG may be administered interstitially for the visualization of lymph nodes, lymphatic channels, or a combination thereof. When injected interstitially, the protein binding properties of ICG cause it to be rapidly taken up by the lymph and moved through the conducting vessels to the SLN. ICG may be provided for injection in the form of a sterile lyophilized powder containing 25 mg ICG (e.g., 25 mg/vial) with no more than 5.0% sodium iodide. ICG may be then reconstituted with commercially available water (sterile) for injection prior to use. According to an embodiment, a vial containing 25 mg ICG may be reconstituted in 20 ml of water for injection, resulting in a 1.25 mg/ml solution. A total of 4 ml of this 1.25 mg/ml solution is to be injected into a subject (4×1 ml injections) for a total dose of ICG of 5 mg per subject. The cervix may also be injected four (4) times with a 1 ml solution of 1% isosulfan blue 10 mg/ml (for comparison purposes) for a total dose of 40 mg. The injection may be performed while the subject is under anesthesia in the operating room. In some variations the ICG dose (mg) in gynecological cancer sentinel lymph node detection and/or mapping may range from about 0.1 mg to about 5 mg depending on the route of administration. In some variations, the ICG dose may be about 0.1 mg to about 0.75 mg, about 0.75 mg to about 1.5 mg, about 1.5 mg to about 2.5 mg, or about 2.5 mg to about 5 mg. The route of administration may be for example cervical injection, vulva peritumoral injection, hysteroscopic endometrial injection, or a combination thereof. In order to minimize the spillage of isosulfan blue or ICG interfering with the mapping procedure when LNs are to be excised, mapping may be performed on a hemi-pelvis, and mapping with both isosulfan blue and ICG may be performed prior to the excision of any LNs. LN mapping for Clinical Stage I endometrial cancer may be performed according to the NCCN Guidelines for Uterine Neoplasms, SLN Algorithm for Surgical Staging of Endometrial Cancer; and SLN mapping for Clinical Stage I cervical cancer may be performed according to the NCCN Guidelines for Cervical Neoplasms, Surgical/SLN Mapping Algorithm for Early-Stage Cervical Cancer. Identification of LNs may thus be based on ICG fluorescence imaging alone or in combination or co-administration with a colorimetric dye (isosulfan blue) and/or radiotracer.

Visualization of lymph nodes may be qualitative and/or quantitative. Such visualization may comprise, for example, lymph node detection, detection rate, anatomic distribution of lymph nodes. Visualization of lymph nodes according to the various embodiments may be used alone or in combination with other variables (e.g., vital signs, height, weight, demographics, surgical predictive factors, relevant medical history and underlying conditions, histological visualization and/or assessment, Tc-99m visualization and/or assessment, concomitant medications). Follow-up visits may occur on the date of discharge, and subsequent dates (e.g., one month).

Lymph fluid comprises high levels of protein, thus ICG can bind to endogenous proteins when entering the lymphatic system. Fluorescence imaging (e.g., ICG imaging) for lymphatic mapping when used in accordance with the methods and systems described herein offers the following example advantages: high-signal to background ratio (or tumor to background ratio) as NIR does not generate significant autofluorescence, real-time visualization feature for lymphatic mapping, tissue definition (i.e., structural visualization), rapid excretion and elimination after entering the vascular system, and avoidance of non-ionizing radiation. Furthermore, NIR imaging has superior tissue penetration (approximately 5 to 10 millimeters of tissue) to that of visible light (1 to 3 mm of tissue). The use of ICG for example also facilitates visualization through the peritoneum overlying the para-aortic nodes. Although tissue fluorescence can be observed with NIR light for extended periods, it cannot be seen with visible light and consequently does not impact pathologic evaluation or processing of the LN. Also, florescence is easier to detect intra-operatively than blue staining (isosulfan blue) of lymph nodes.

Fluorescence Imaging System with a Configurable Platform

A fluorescence imaging system may be built upon a platform that can be operator-configured for use in a variety of surgical applications (e.g., microsurgery, open field/laparotomy, minimally invasive surgery (laparoscopy/arthroscopy), robotic surgery applications, scintigraphy, etc., or a combination thereof) and that can simultaneously be operator-configured for use with fluorophores (imaging agents) having fluorescence excitation/emission wavebands from the UV through the visible and NIR spectrums, or a selected subset of this range. Previous intraoperative fluorescence imaging devices appear to have historically been conceived and developed with a specific surgical application in mind, and even devices that attempt to add some degree of user-configurability are either limited to one or two surgical configurations or to one or two fluorescence wavebands.

In some variations, as shown in FIG. 1, the fluorescence imaging system 100 may be structured as an assembly of modular components including one or more operative modules 110 and one or more modules 120. The modules 120 may be surgery-specific (e.g., for a single type of surgery and/or allow selection for a different type of surgery), and may further be referred to as surgery-specific modules 120. In some variations, the system 100 may include one or more accessory modules 130 and/or data modules 140. Operative modules 110 may include components that provide white light for illumination and/or light for fluorescence excitation, and components that generate images from reflected white light and/or fluorescence emission light. Surgery-specific modules 120 may couple to one or more of the operative modules in order to establish imaging device configurations that are designated for specific types of surgeries. Accessory modules 130 may be interconnected with some or all of the other modules and may provide mechanical support or enclosure for one or more of the modules, aid in the interconnection/adaptation of other modules, and/or perform suitable functions not provided by the other modules. Data modules 140 may be interconnected with some or all of the other modules and provide additional functions such as enabling image and data display, recording, and/or printing. Although the components of the system are primarily described herein as grouped in these modules, in some variations, the various components may be organized and grouped in any suitable manner (that is, the various components described herein may be combined and arranged in assemblies and subassemblies different from the modules described herein).

In some variations, a fluorescence imaging system for imaging an object may include: a white light provider that emits white light, an excitation light provider that emits excitation light in a plurality of excitation wavebands for causing the object to emit fluorescent light, an interchangeable surgery-specific component that directs the white light and excitation light to the object and collects reflected white light and emitted fluorescent light from the object, a filter that blocks substantially all light in the excitation wavebands and transmits at least a substantial portion of the reflected white light and fluorescent light, and an image sensor that receives the transmitted reflected white light and the fluorescent light. In some variations, the excitation light provider emits non-overlapping excitation wavebands for causing the object to emit fluorescent light. As used herein, non-overlapping wavebands include substantially non-overlapping wavebands whereby the signal strength of any overlapping portion is minimal relative to the center frequency signal strength. For example, in some variations, the signal strength of any overlapping portion is at least one order of magnitude less, at least two orders of magnitude less, at least four orders of magnitude less, or at least 10 orders of magnitude or less than the center frequency signal strength.

Operative Modules

In some variations, the operative modules of the fluorescence imaging system 100 may include an illumination module 210, an optical image acquisition module 220, a controller module (and/or a 3D controller module), a processor module (and/or a 3D processor module), and/or a post processor/data manager module.

Illumination Module

Figure 2A:
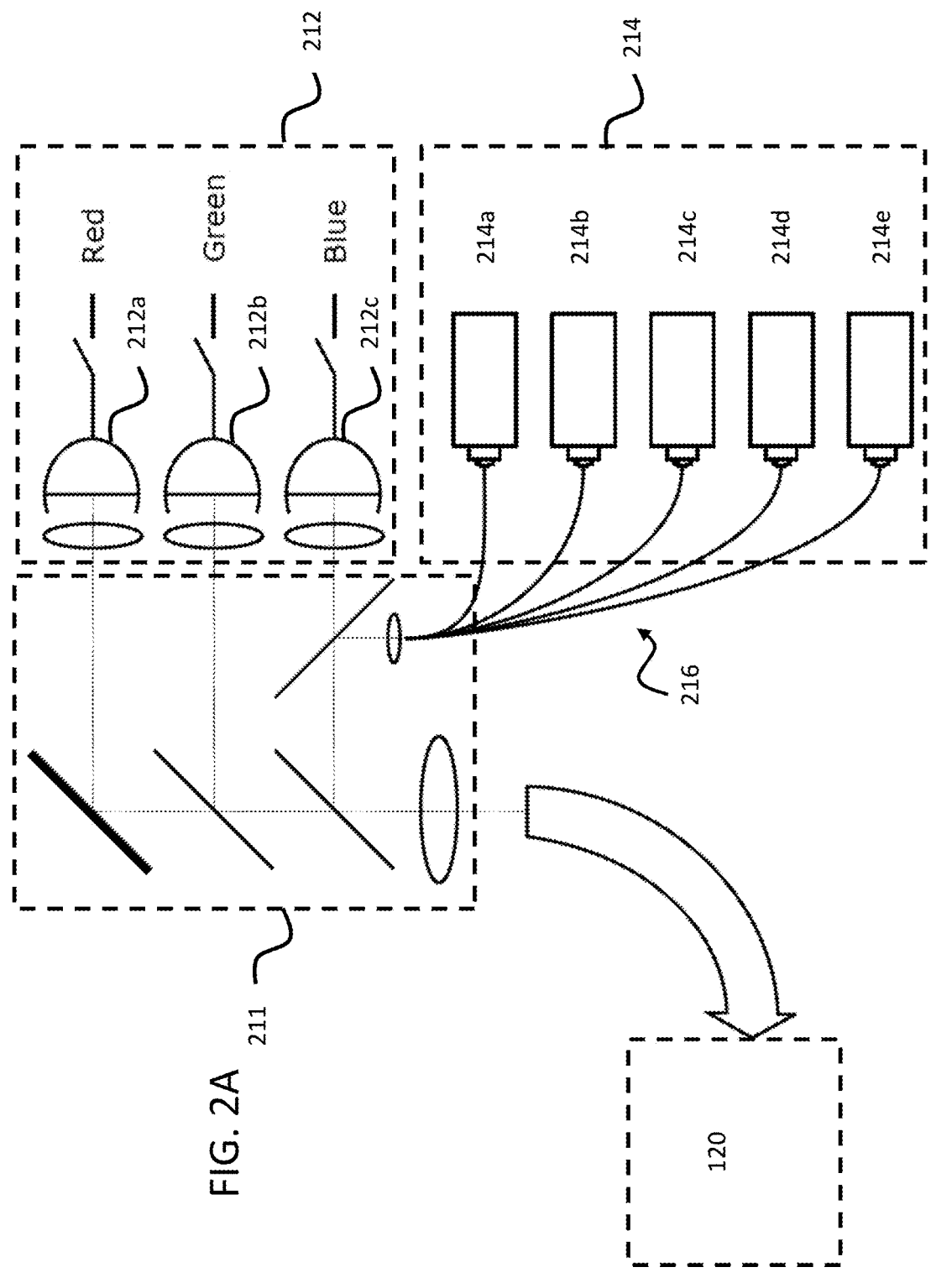
FIG. 2A is an illustrative depiction of an exemplary illumination module in a fluorescence imaging system.

As shown in FIG. 2A, the illumination module 210 may contain a white light provider 212 (with one or more light sources 212a, 212b, and 212c) that emits visible (white) light, an excitation light provider 214 (with one or more excitation light sources 214a, 214b, 214c, 214d, and 214e) that emits excitation light, and optics 211 for manipulating the white light and/or excitation light.

The white light provider 212 may include multiple discrete color light sources (e.g., 212a, 212b, and 212c) that in combination provide white light, or may include one or more white light sources. Additionally, the white light provider may include light sources that are solid state (e.g., LEDs, laser diodes, etc.) and/or non-solid state. For example, in one variation, the white light provider may include a combination of discrete color solid state sources such as red, green, and blue LEDs and/or diode lasers. In another variation, the white light provider may include white LEDs. In yet another variation, the white light provider may include one or more broad spectrum non-solid state sources such as arc lamps, which in some variations may be combined with color correction filters. In another variation, the white light provider may include any suitable combination of the above.

Figure 3B:
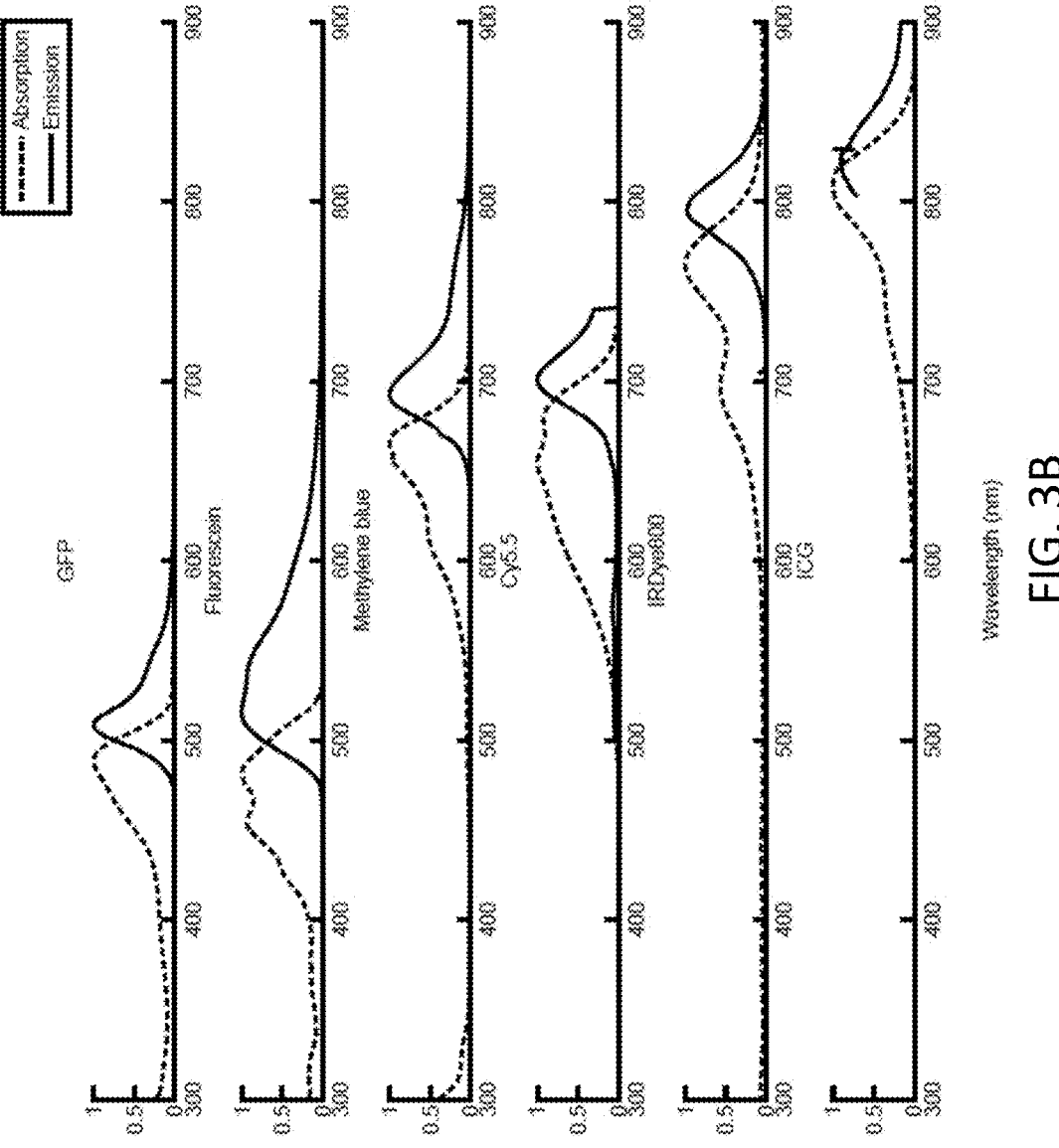
FIG. 3B is a plot of absorption and emission spectra for selected fluorophores described in FIG. 3A.
Figures 4A, 4B:
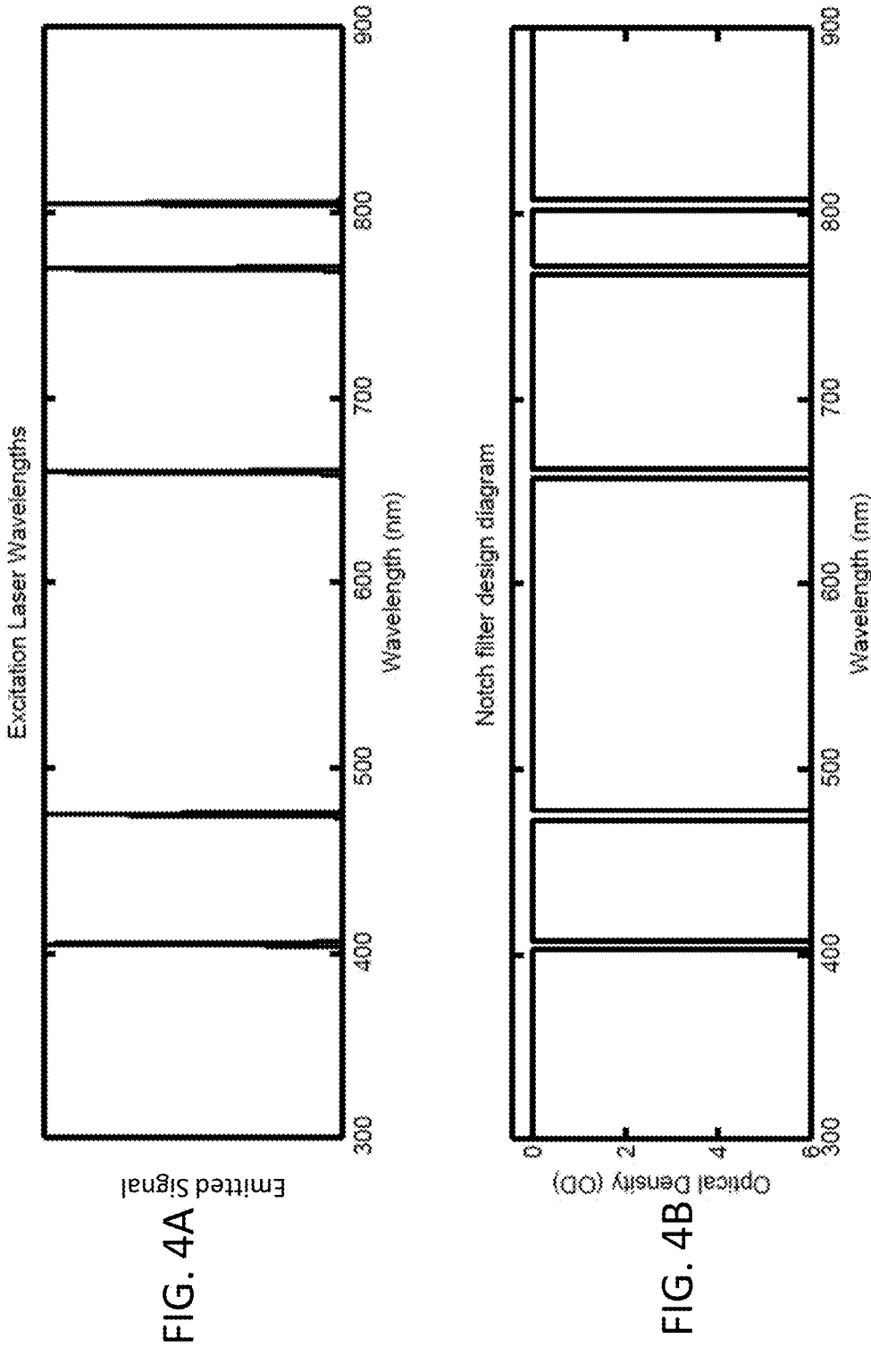
FIG. 4A is an illustrative diagram of the spectrum of excitation light emitted by an exemplary illumination module.
FIG. 4B is an illustrative diagram of the spectrum of light that is blocked by an exemplary fluorescence excitation light blocking filter.

The excitation light provider may include one or more light sources (e.g., 214a-214d) that emit light in multiple wavebands for fluorescence excitation. The multiple wavebands are preferably non-overlapping or sufficiently separated from each other such that a single multi-band fluorescence excitation blocking filter can be used, as described further below. As a result, the need for moving multiple blocking filters into and out of the imaging path may be eliminated in some variations. In some variations, the excitation light provider may emit fluorescent light in a plurality of non-overlapping excitation wavebands within the ultraviolet (UV), visible, and near-infrared (NIR) spectrum. Each excitation waveband is designated to excite a corresponding endogenous or exogenously-introduced fluorophore, and to result in a corresponding approximate emission waveband of fluorescent light emitted from the fluorophore. In an exemplary embodiment, the excitation light provider may emit light in three or more of the excitation wavebands shown in FIG. 3A. For example, as shown in FIG. 4A, the excitation light provider may emit light in Band 1 (about 405 nm excitation light), Band 2 (about 470-480 nm excitation light), Band 3 (about 660 nm excitation light), Band 4 (about 760-780 nm excitation light), and Band 5 or 6 (about 805 nm excitation light). The excitation light provider may additionally or alternatively emit light in Band 7 (about 750-810 nm excitation light). However, the excitation light provider may emit light in any suitable number (e.g., 2, 3, 4, 5, 6 or all 7) of Bands 1, 2, 3, 4, 5, 6 and 7 summarized in FIG. 3A, and in any suitable combination. The absorption and fluorescent emission spectra of selected exemplary fluorophores from FIG. 3A are illustrated in FIG. 3B. Furthermore, the excitation light provider may additionally or alternatively include one or more light sources that emit light in other suitable, sufficiently separated wavebands other than those summarized in FIG. 3A.

As shown in FIG. 2A, the excitation light provider may include multiple light sources (e.g., 214a, 214b, 214c, 215d, etc.) where each light source is configured to emit light in a defined excitation waveband. Additionally, the excitation light provider may include light sources that are solid state (e.g., LEDs, laser diodes, etc.) and/or non-solid state. In one variation, the excitation light provider may include narrow spectrum, solid state sources, such as laser diodes. In another variation, the excitation light provider may include broader spectrum solid state sources, such as LEDs. In yet another variation, the excitation light provider may include non-solid state sources, such as arc lamps. Broad spectrum light sources (solid state or non-solid state) may be coupled with output spectrum narrowing optical filters that limit and determine the spectrum of light emitted from the light source/optical filter subassembly.

As shown in FIG. 2A, the illumination module may include optics 211 and/or 216, which may include light combining and projection optics (e.g., lenses, mirrors, dichroics, fiber optics, etc.). In some variations, these optics may combine the light emitted by the white light provider and excitation light provider into a single optical path that enables light from the multiple light sources to be output through a single connection port. For example, as shown in FIG. 2A, each of the excitation light sources may be coupled to an optical fiber, and the optical fibers may be bundled into a single output connection port configured to receive an output fiber optic or liquid light guide. In other variations, the optics may organize the light emitted by the white light provider and/or excitation light provider into two, three, or any suitable number of optical paths for output. The output of the illumination module may be coupled to one or more of the other modules, such as the surgery-specific module, as described below.

In some variations, the illumination module may be configured such that some of the multiple excitation light sources are arranged separately within the module and light from these excitation light sources is directed into a common module light path at separate points or from separate orientations.

Figure 2D:
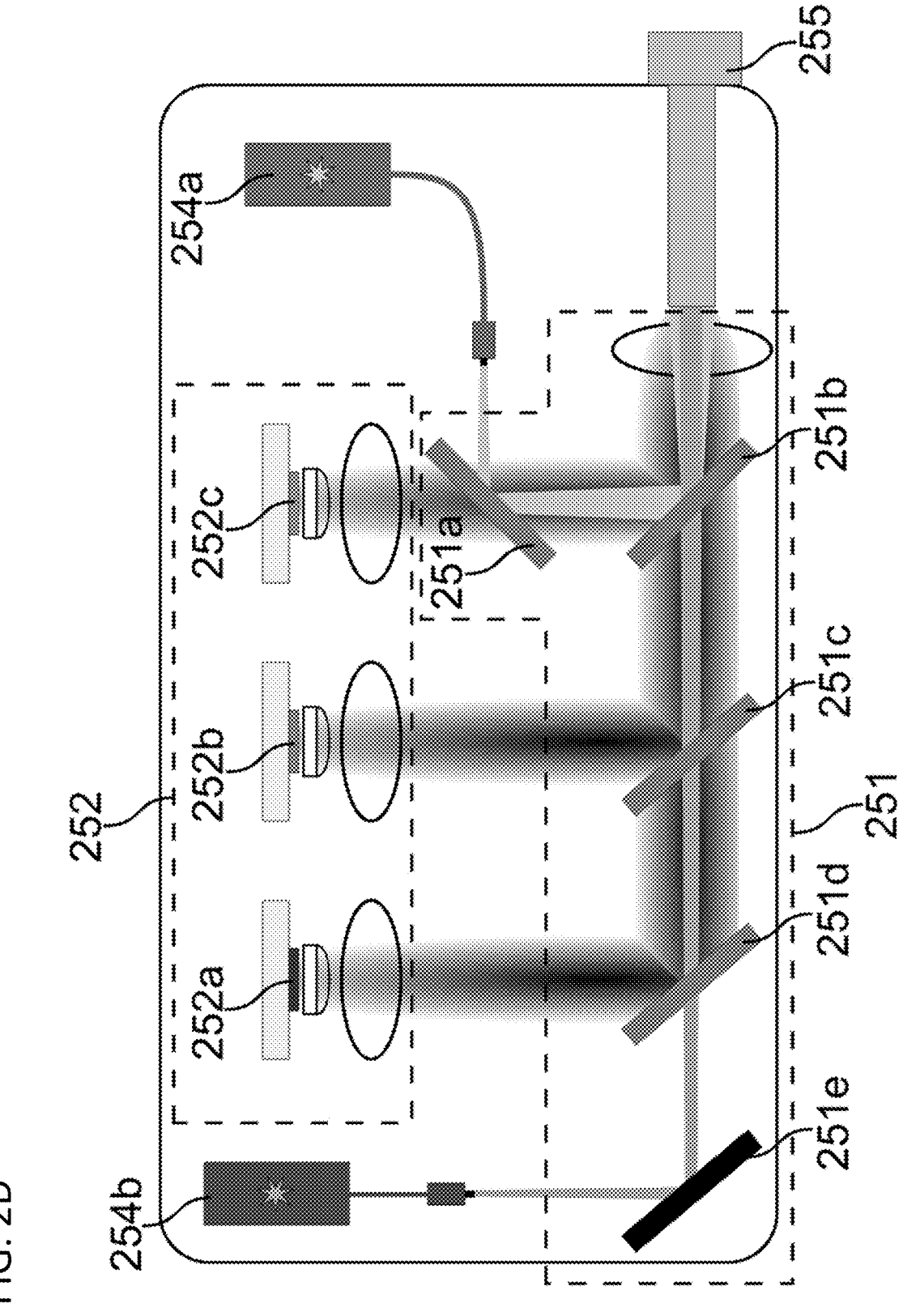
FIGS. 2D and 2E are illustrative depictions of other variations of exemplary illumination modules in a fluorescence imaging system.

In one example, as shown in FIG. 2D, the illumination module may include a first excitation light source 254a, a second excitation light source 254b, and a white light provider 252, with light from each being directed into a common illumination module light path that exits via port 255 to be connected to a light guide. Light from the excitation light source 254a may be directed into the common light path via a dichroic mirror 251a placed in the light path ahead of a blue light source 252c, and light from the excitation light source 254b may be directed into the common light path via a mirror 251e placed behind a set of dichroic mirrors 251b-d for directing light from the white light provider 252 into the common light path. In one embodiment, the first excitation light source 254a may emit a narrow spectrum of light with wavelength about 805 nm (e.g., for excitation of ICG), and the second excitation light source 254b may emit a narrow spectrum of light with wavelength about 675 nm (e.g., for excitation of methylene blue).

Figure 2E:
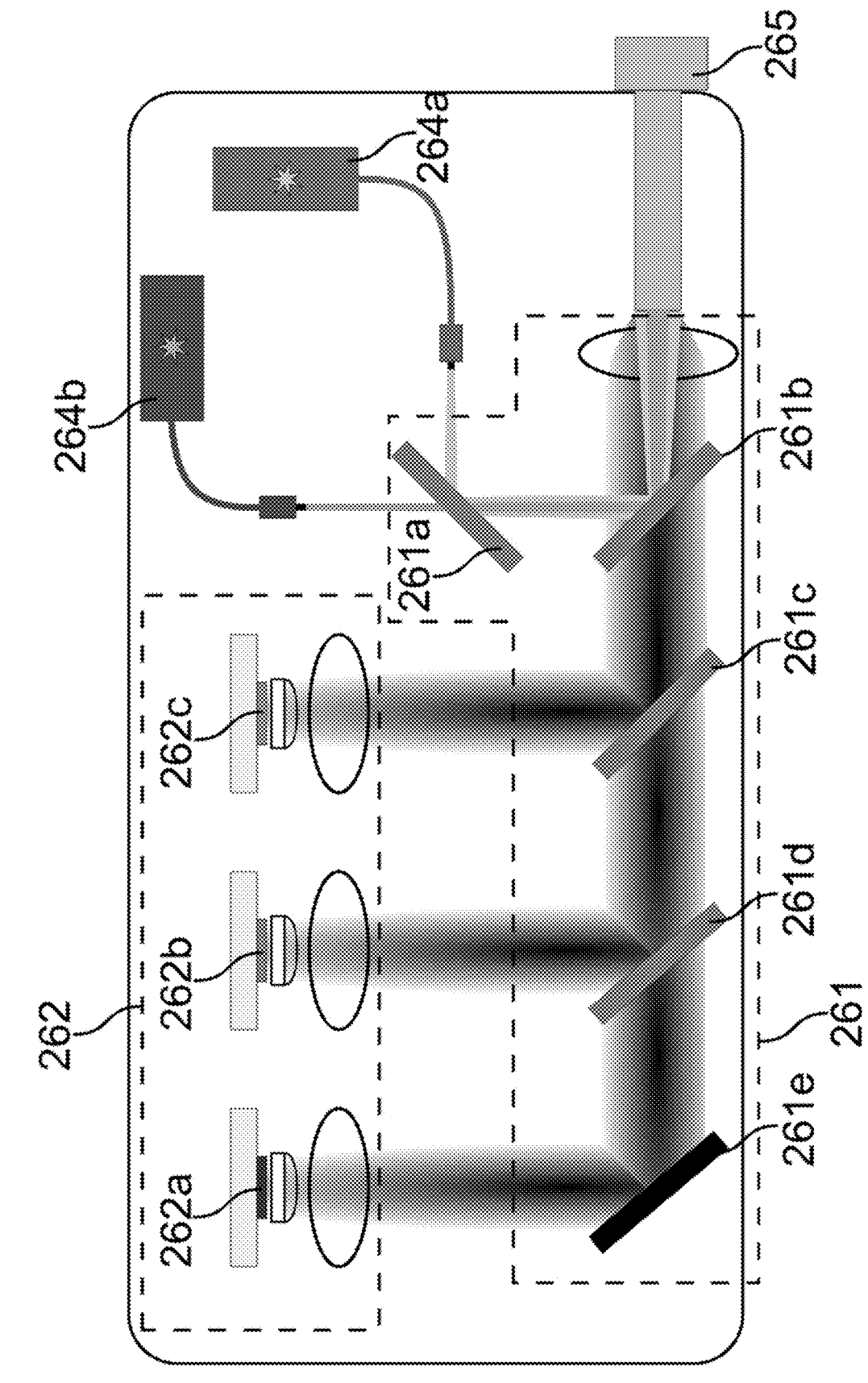

In another example, as shown in FIG. 2E, the illumination module may include a first excitation light source 264a, a second excitation light source 264b, and a white light provider 262, with light from each being directed into a common illumination module light path that exits via port 265 to be connected to a light guide. Light from the excitation light source 264a may be directed into the common light path by reflection via dichroic mirror 261a and dichroic mirror 261b placed in the light path ahead of the white light provider 262, while the light source 264b may be directed into the common light path via transmission through dichroic mirror 261a and reflection via dichroic mirror 261b. In one embodiment, the first excitation light source 264a may emit a narrow spectrum of light with wavelength about 805 nm (e.g., for excitation of ICG), and the second excitation light source 264b may emit a narrow spectrum of light with wavelength about 675 nm (e.g., for excitation of methylene blue).

Optical Image Acquisition Module

As shown in FIGS. 2B-2C, the optical image acquisition module 220 may include camera optics 226 and an image sensor assembly 223. In some variations, the camera optics 226 may include at least one fluorescence excitation light blocking filter 228 and projection optics (e.g., 230a and 230b) to project light onto the image sensor assembly 223. As best shown in FIGS. 2B and 2C, the fluorescence excitation light blocking filter 228 may be located in the optical path between the object being imaged and the image sensor assembly 223, in order to substantially exclude excitation light from reaching the image sensor assembly. For instance, the fluorescence excitation light blocking filter may be physically integrated as part of the camera optics in the image acquisition module. In another variation, the fluorescence excitation light blocking filter may be integrated in a separate optical coupling accessory that is mounted to the input of the image acquisition module and is used to couple any one or more of the surgery-specific modules to the image acquisition module. In another variation, the fluorescence excitation light blocking filter may be integrated with the surgery-specific modules. However, the fluorescence excitation light blocking filter may be located in any suitable place in the optical path between the object being imaged and the image sensor assembly.

Blocking Filter and Camera Optics

The fluorescence excitation light blocking filter 228 may block substantially all light in the excitation wavebands (e.g., excitation light that may be reflected or remitted from the object being imaged) and transmit at least a substantial portion of the white light reflected by the object and fluorescent light emitted by the fluorophores in the object. The fluorescence excitation light blocking filter 228 may be a multi-band notch filter to block light in the non-overlapping excitation wavebands. For example, as shown in FIG. 4B, in a system in which the illumination module emits light at excitation wavebands according to Bands 1, 2, 3, 4, 5, and 6 described in FIG. 3A, the fluorescence excitation light blocking filter may selectively substantially block light in Bands 1, 2, 3, 4, 5, and 6 while substantially transmitting light in all other wavebands. Similarly, in a system in which the illumination module additionally emits light at excitation wavebands according to Bands 1-7 described in FIG. 3A, the fluorescence excitation light blocking filter may selectively substantially block light in Bands 1-7, while substantially transmitting light in wavebands other than one or more of Bands 1-7. In some variations, the fluorescence excitation light blocking filter may be characterized by an optical density (OD) of at least about 4 when blocking the fluorescence excitation wavebands of the illumination spectrum. For instance, the fluorescence excitation light blocking filter may have an OD of 4, 5, or 6, or greater. In some variations, the fluorescence excitation light blocking filter may be characterized as having high transmission (e.g., about 90% or greater) in parts of the spectrum other than the excitation wavebands. Furthermore, in some variations, the fluorescence excitation light blocking filter may be characterized as having steep transition regions (e.g., a transition width less than about 10 nm) between substantially transmitted and substantially blocked portions of the light spectrum. However, the fluorescence excitation light blocking filter may have any suitable OD for blocking fluorescence excitation wavebands, any suitable transmission rate in the non-excitation waveband portions of the spectrum, and any suitable transition region between substantially transmitted and substantially blocked portions of the light spectrum.

Figure 9:
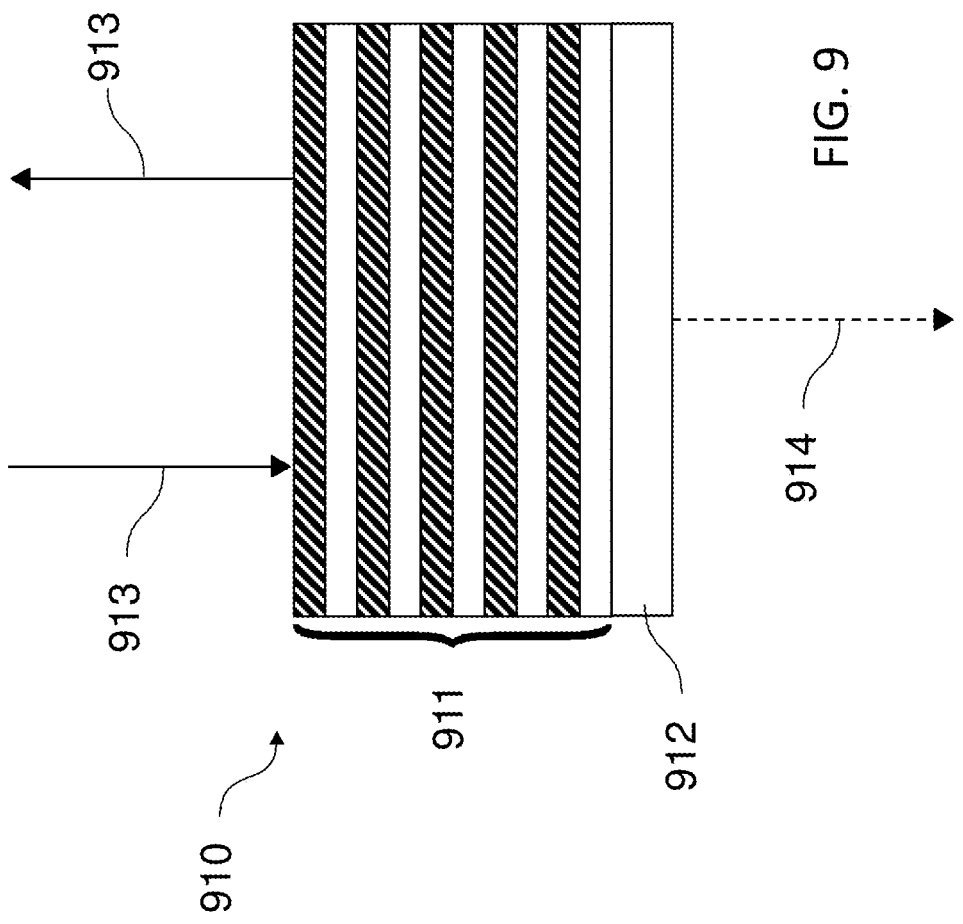
FIG. 9 is an illustrative schematic of a multi-band fluorescence excitation light blocking filter.

For instance, the fluorescence excitation light blocking filter 228 may include at least one substrate (e.g., glass substrate) with one or more dielectric coatings, which may be configured, alone or in combination, to substantially block light in a selected waveband (e.g., by including a material with a refractive index suitable for preventing transmission of the selected waveband through the coating). By including multiple dielectric blocking coatings, the fluorescence excitation light blocking filter 228 may substantially block or prevent passage of light in a plurality of selected fluorescence excitation wavebands corresponding to the filter characteristics of multiple dielectric coatings, while substantially transmitting light in other wavelengths. For example, as shown in FIG. 9, the fluorescence excitation light blocking filter may be a multi-band notch filter 910 having multiple dielectric coatings 911 with alternating high and low refractive indexes on a glass substrate 912, which collectively block multiple wavebands of light corresponding to excitation of multiple types of fluorophores. Additionally or alternatively, multiple single-notch blocking filters with different dielectric coatings may be combined (e.g., placed in series) so as to block multiple wavelengths.

As shown in the two variations of FIGS. 2B and 2C, the camera optics 226 may include projection optics (e.g., 230a and 230b) that project light onto the image sensor assembly 223. More specifically, the projection optics may project onto the image plane of the image sensor assembly light that is transmitted by the fluorescence excitation blocking filter (including reflected white light and emitted fluorescent light). For example, the projection optics may include various lenses and/or mirrors to direct the transmitted light onto the image sensor assembly, and/or any other suitable optical components.

Image Sensor Assembly

The image sensor assembly 223 in the optical image acquisition module 220 may include one or more image sensors and various sensor electronics (not shown). In some variations, the image sensor assembly 223 may include solid state image sensors, but in other variations the image sensor assembly may additionally or alternatively include any suitable non-solid state image sensors. In some variations, the solid state image sensors may be at least high definition (HD) or ultra-high definition (4K) in spatial resolution, but in other variations the image sensors may have any suitable resolution.

The image sensor assembly 223 may include one or more image sensors configured to detect light at least in the UV, visible and/or near-infrared I (NIR-I) wavebands (e.g., below about 900 nm). In particular, in one variation, the image sensor assembly 223 may include a single solid state image sensor comprising technology such as silicon-based CMOS technology, CCD technology, CID technology, etc. For example, the image sensor may be a monochrome image sensor. As another example, as shown in FIG. 2C, the image sensor may be a color image sensor with an appropriate color filter array (CFA) whose elements are deposited on the sensor pixels. The CFA may include, for example, a Bayer pattern with RGB (red, green, blue), CMYG (cyan, magenta, yellow, green), or WRGB (white, red, green, blue) filters. In another variation, as shown in FIG. 2B, the image sensor assembly may consist of three (or other suitable number) solid state image sensors each including CMOS technology, CCD technology, CID technology, etc., which may be arranged on (or in the optical path following) a Philips prism or other spectral splitting technology.

In some variations, the image sensor assembly 223 may additionally or alternatively include one or more image sensors configured to detect light at least in the near-infrared II (NIR-II) waveband (e.g., above about 900 nm). Image sensors that detect NIR-II light may be used, for example, to image tissue at a greater depth beneath the surface of tissue than other image sensors (e.g., sensors that only detect UV, visible, and/or NIR-I light).

Figure 10:
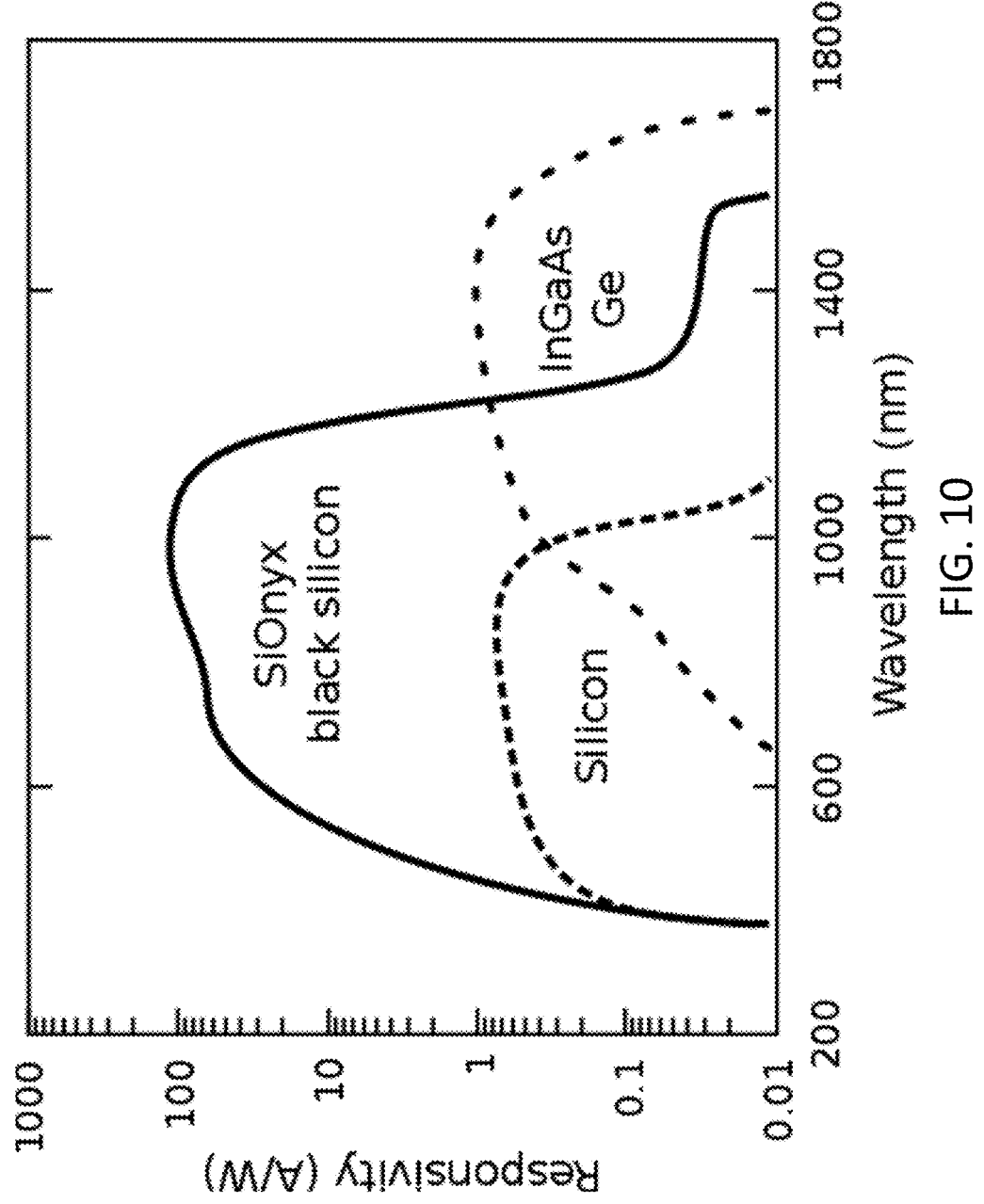
FIG. 10 is a plot of responsivity to different wavebands offered by silicon-based detectors, SiOnyx black silicon detectors, and indium-gallium-arsenide (InGaAs) detectors.

In one example, the image sensor assembly 223 may include at least one indium gallium arsenide (InGaAs) image sensor and/or germanium (Ge) image sensor configured to detect light at least in the NIR-II waveband. As shown in FIG. 10, an InGaAs image sensor or Ge image sensor may detect light with wavelengths generally between about 650 nm and about 1700 nm, with high detection sensitivity for light generally in the NIR-II waveband (e.g., between about 900 nm and 1700 nm). In some variations, the InGaAs image sensor or Ge image sensor may be used in combination with an image sensor that detects light outside of the NIR-II waveband (e.g., light in the visible and/or NIR-I wavebands) such that the image sensor assembly 223 is configured to detect a wider spectrum of light for visible and/or fluorescence imaging.

As another example, the image sensor assembly 223 may include at least one "black silicon" image sensor (e.g., XQE series of CMOS image sensors produced by SiOnyx LLC). As shown in FIG. 10, black silicon image sensors may detect light with wavelengths generally between about 400 nm and about 1600 nm, with high detection sensitivity for light generally including visible and NIR light between about 600 nm and about 1200 nm, which is further into the NIR-II waveband than what is detected with some other silicon image sensors. In some variations, a single black silicon image sensor may be used for both reflected visible light color imaging and for fluorescence imaging in the NIR-I and/or NIR-II wavebands. In these variations, the image sensor signals corresponding to reflected visible light images may be extracted and formed into color images through spatial means or temporal image processing methods. For instance, the black silicon image sensor may have a CFA coupled to or deposited on its sensor pixels, where color images (reflected visible light images) may be formed by spatial image processing techniques (e.g., demosaicing and spatial interpolation between pixels of the same color, as further described below). As another example, in variations in which a single black silicon image sensor is used for both reflected visible light color imaging and for fluorescence imaging in the NIR-I and/or NIR-II wavebands, the black silicon image sensor may lack a CFA but provide for formation of color images through temporally-based image processing techniques (e.g., synchronized pulsing and image sensor readout schemes, as further described below).

Figures 11A, 11B:
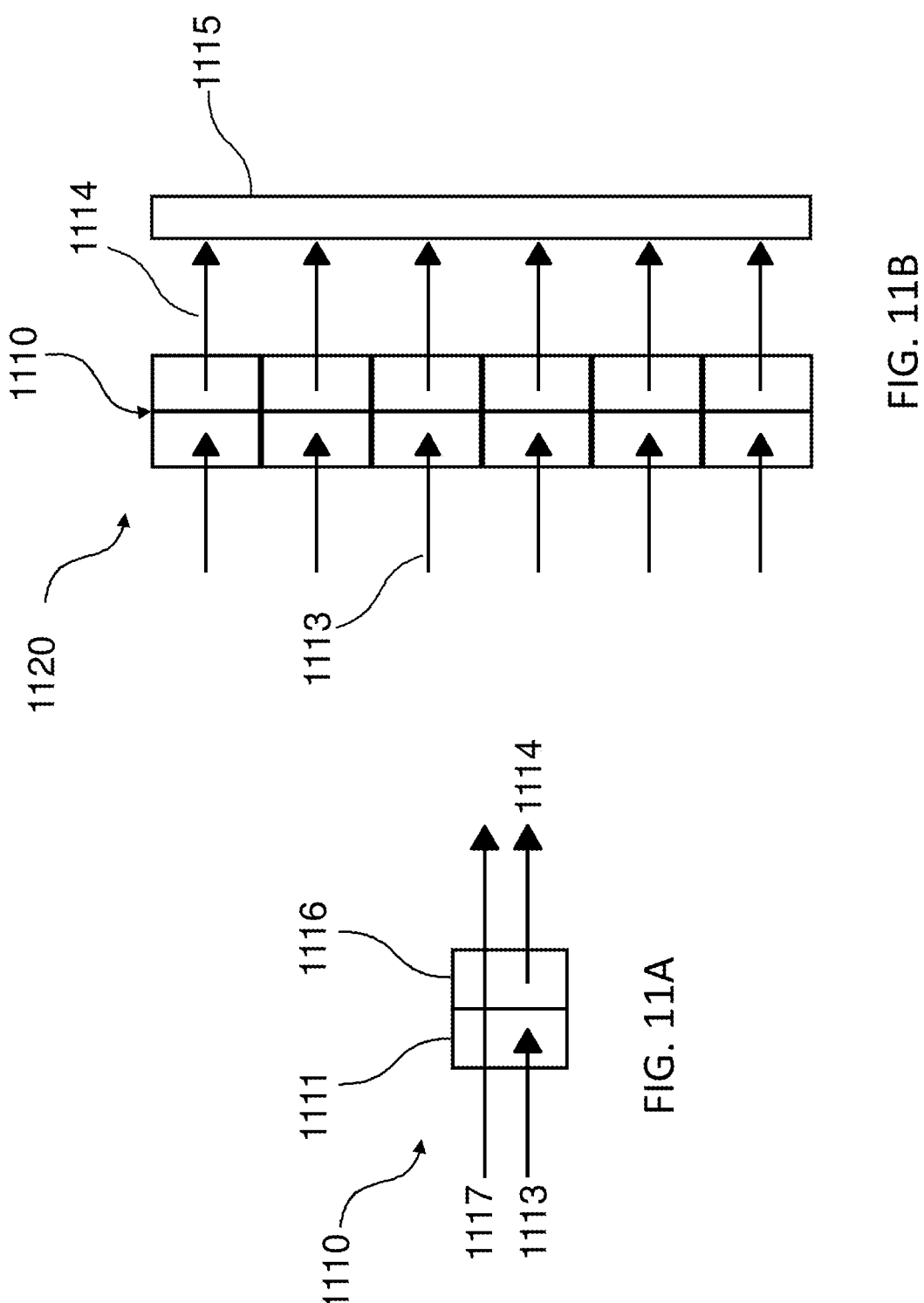
FIG. 11A is a schematic of a NIR-to-visible light upconverter.
FIG. 11B is a schematic of a NIR-to-visible upconverter array in combination with an image sensor.

As another example, the system may include at least one upconverter that transforms incident light in at least the NIR-II waveband into visible light. For example, as shown in FIG. 11A, an upconverter 1110 may include an NIR photodetector 1111 and an organic light-emitting diode 1116 (OLED) coupled to the photodetector 1111, where the photodetector 1111 and OLED 1116 are configured to up-convert incident NIR light 1113 (e.g., NIR-I and/or NIR-II light) into converted visible light 1114. For example, the photodetector 1111 and OLED 1116 may be configured in a manner similar to that described in U.S. Patent Pub. No. 2012/0286296 or in U.S. Patent Pub. No. 2014/0217284, the contents of which are incorporated in their entirety by this reference. However, the system may additionally or alternatively include other suitable NIR-to-visible upconverters. The upconverter 1110 may, in some variations, be further configured to transmit incident visible light 1117. The converted visible light 1114 and/or transmitted visible light 1117 may subsequently be received and detected by one or more sensors in the image sensor assembly. In some variations, the system may include multiple upconverters in an array. For example, as shown in FIG. 11B, a NIR-to-visible upconverter array 1120 may include a plurality of upconverters 1110 that receive incident NIR light 1113, convert the incident NIR light 1113 into visible light, and emit converted visible light 1114 toward at least one image sensor 1115. The image sensor 1115 may, for example, be a silicon-based CMOS or CCD sensor. In some variations, the upconverter array 1120 may further transmit incident visible light such that the image sensor 1115 detects both the transmitted visible light including information for the white light image and the converted visible light for the fluorescence image signals.

At least one image sensor that detects light in at least the UV, visible, and/or NIR-I wavebands may be combined with at least one image sensor that detects light in at least the NIR-II waveband. For example, the image sensor assembly may include one or more image sensors that detect fluorescence emission in any of Bands 1-7 shown in FIG. 3A, in any combination. In some of these variations in which the image sensor assembly is configured for broad spectrum imaging in the UV, visible, NIR-I, and/or NIR-II spectrums, the optics in the optical image acquisition module 220, any accessory modules 130 in the image path, and/or the surgery-specific modules 120 may be coated to substantially transmit light in these wavebands (with the exception of wavelengths blocked by the fluorescence excitation light blocking filter, etc.). Furthermore, in some of these variations, the optical design of these modules may be corrected to provide images that display minimal optical aberration across the transmitted spectrum.

In some variations, the image sensor assembly may include multiple image sensors arranged on (or in the optical path following) a Philips prism or other spectral splitting technology. The prism or other beamsplitters may receive incident light (which may include UV, visible, NIR-I, and/or NIR-II light, etc.) and spectrally distribute the incident light onto the multiple image sensors such that each image sensor receives a subspectrum of light transmitted by the fluorescence excitation light blocking filter. These sensors may be arranged in several different configurations including, but not limited to, a two-sensor, three-sensor, four-sensor, or five-sensor configurations, such that each image sensor receives a subspectrum of the light transmitted by the fluorescence excitation blocking filter.

Figures 12A, 12B, 12C, 12D:
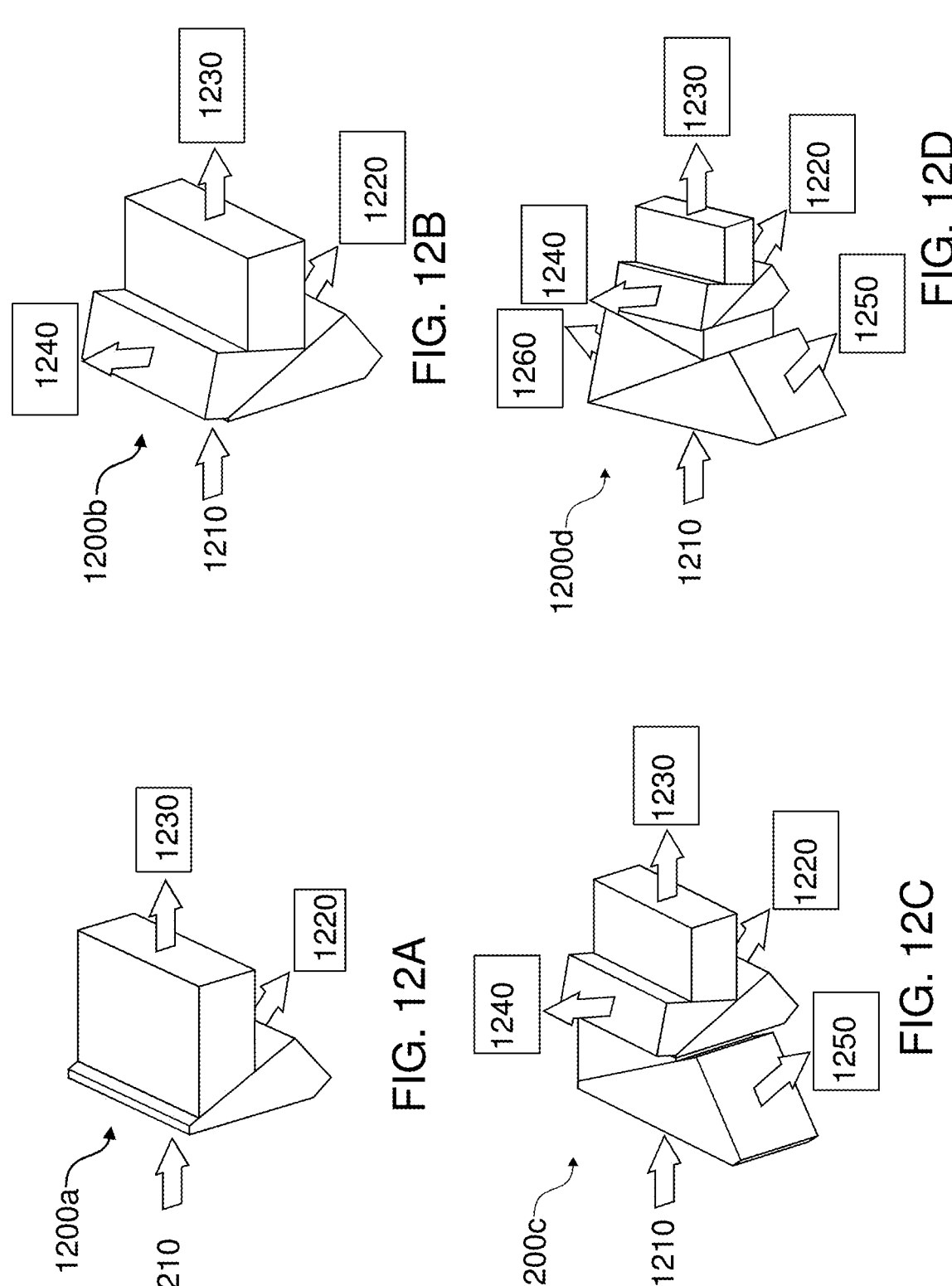
FIGS. 12A-12D are illustrative depictions of variations of beam-splitting prism and sensor configurations.

In one variation, the image assembly may include a two-sensor prism configuration including a beam splitter that divides incident light into two subspectrums of light. For example, as shown in FIG. 12A, the two-sensor prism configuration may include a beam splitter 1200*a* that receives and spectrally divides incident light 1210 transmitted by the fluorescence excitation light blocking filter into a first branch toward a first sensor 1220 and a second branch toward a second sensor 1230. For instance, first sensor 1220 may be configured to detect NIR-I and/or NIR-II light for the fluorescence image and second sensor 1230 may be a color image sensor with a CFA or a monochrome image sensor configured to detect visible light for the white light image. However, the two-sensor prism configuration may include sensors configured to detect any suitable subspectrums of light that are formed by the beam splitter.

In another variation, the image assembly may include a three-sensor prism configuration including a beam splitter that divides incident light into three subspectrums of light. For example, as shown in FIG. 12B, the three-sensor prism configuration may include a beam splitter 1200*b* that receives and spectrally divides incident light 1210 transmitted by the fluorescence excitation light blocking filter into a first branch toward a first sensor 1220, a second branch toward a second sensor 1230, and a third branch toward a third sensor 1240. For instance, the first sensor 1220 may be configured to detect blue light, the second sensor 1230 may be configured to detect green light, and the third sensor 1240 may be configured to detect red light, where the signals for detected blue, green, and red light may be combined for a full white light or color image. As another example, the first sensor 1220 may be configured to receive NIR-I light for a first fluorescence image, the second sensor 1230 may be a color sensor with a CFA configured to receive visible light for the white light image, and third sensor 1240 may be configured to receive NIR-II light for a second fluorescence image. However, the three-sensor prism configuration may include sensors configured to detect any suitable subspectrums of light that are formed by the beam splitter.

In another variation, the image assembly may include a four-sensor prism configuration including a beam splitter that divides incident light into four subspectrums of light. For example, as shown in FIG. 12C, the four-sensor prism configuration may include a beam splitter 1200*c* that receives and spectrally divides incident light 1210 transmitted by the fluorescence excitation light blocking filter into a first branch toward a first sensor 1220, a second branch toward a second sensor 1230, a third branch toward a third sensor 1240, and a fourth branch toward a fourth sensor 1250. For instance, the first sensor 1220 may be configured to detect blue light, the second sensor 1230 may be configured to detect green light, the third sensor 1240 may be configured to detect red light, and the fourth sensor 1250 may be configured to detect NIR-I or NIR-II light. In this example, the signals for detected blue, green, and red light may be combined for a full white light or color image, while the signals for the detected NIR-I or NIR-II light may be for a fluorescence image. However, the four-sensor prism configuration may include sensors configured to detect any suitable subspectrums of light that are formed by the beam splitter.

In another variation, the image assembly may include a five-sensor prism configuration including a beam splitter that divides incident light into five subspectrums of light. For example, as shown in FIG. 12D, the five-sensor prism configuration may include a beam splitter 1200*d* that receives and spectrally divides incident light 1210 transmitted by the fluorescence excitation light blocking filter into a first branch toward a first sensor 1220, a second branch toward a second sensor 1230, a third branch toward a third sensor 1240, a fourth branch toward a fourth sensor 1250, and a fifth branch toward a fifth sensor 1260. For instance, the first sensor 1220 may be configured to detect blue light, the second sensor 1230 may be configured to detect green light, the third sensor 1240 may be configured to detect red light, the fourth sensor 1250 may be configured to detect NIR-I light, and the fifth sensor 1260 may be configured to detect NIR-II light. In this example, the signals for detected blue, green, and red light may be combined for a full white light or color image, while the signals for the detected NIR-I and NIR-II light may be for fluorescence images. However, the four-sensor prism configuration may include sensors configured to detect any suitable subspectrums of light that are formed by the beam splitter.

Sensor Electronics

Sensor electronics may include sensor readout control electronics that adjust the operation of the sensor. The image sensor assembly may additionally or alternatively include image signal management electronics (e.g., amplifier, digitizer, memory, serializer, etc.) to prepare the electronic image signal for transmission to the controller and/or image processor module. However, in some variations, these electronics may be located outside of the image sensor assembly itself, and instead in any suitable location (e.g., as part of the controller, etc.).

Other Modules

As shown in FIG. 1, the system may include a controller module, a 3D controller module, a processor module, a 3D processor module, and/or a post-processor/data manager module 110*c*. The controller module may communicate with, control, and synchronize the operation of the illumination module and the optical image acquisition module, and/or any other components that involve coordination for capturing images. The controller module may include an internal clock to enable control of the various elements and help establish correct timing of illumination and sensor shutters.

The processor module may receive the electronic image signal from the image acquisition module and process (e.g., in real-time or near real-time) the signal to create images and/or other data, such as for output to display and/or recording. In some variations, the controller module and/or processor module may be embodied on any computer or computing means such as, for example, a tablet, laptop, desktop, networked computer, dedicated standalone microprocessor, etc. For instance, the controller module and/or processor module may include one or more central processing units (CPU). In some variations, the controller module and processor module may be integrated as a combined controller and processor module 110*b* as shown in FIG. 1.

In some variations in which the system includes a stereoscopic surgery-specific module (e.g., stereoscopic videoscope or other stereoscopic surgical device as described further below), the system may include a 3D controller module and/or 3D processor module for robotics applications (in this case the regular controller processor may not be utilized) which subsequently outputs a 3D image data signal to the appropriate 3D compatible accessory modules (displays, recorders, etc.). In some variations, the 3D controller module and 3D image processing module may be integrated as a combined 3D controller and 3D processor module 110*a* as shown in FIG. 1.

The post-processor/data manager module 110*c* may receive the images from the processor (or 3D processor) and perform additional processing steps, such as overlaying of white light images and fluorescence images, or otherwise modifying images, as further described below with respect to the operation of the fluorescence imaging system. The post processor/data manager module 110*c* may additionally or alternatively manage the output of image data generated (e.g., with respect to the data modules 140). Although the post-processor/data manager module 110*c* may be embodied in a physical unit separate from the controller module and/or image processor (or 3D controller module and/or 3D image processor) as pictured in FIG. 1, in other variations, the post-processing module 110*c* may be integrated with any of the other modules. Furthermore, the post-processor/data manager module 110*c* may be divided into separate modules (e.g., one post-processor module and one data manager module).

Surgery-Specific Modules

As shown in FIG. 1, the fluorescence imaging system may include one or more surgery-specific modules 120. Each surgery-specific module may be primarily designated for a particular kind or category of surgical application, and may be interchangeable with other surgery-specific modules and/or selectable such that the fluorescence imaging system is a platform configurable by an operator (e.g., clinician) for a particular kind of surgical procedure. In many instances, the surgery-specific modules may be largely opto-mechanical in nature, but need not be. The surgery-specific modules may interconnect indirectly (e.g., via light guide 130*a*) or directly with one or more of the modules to direct the white light and excitation light to the object and collect reflected white light and emitted fluorescent light from the object. In some variations, an accessory module (e.g., light guide) may transmit the reflected white light and emitted fluorescent light to the image acquisition module. In other variations, the surgery-specific module may directly transmit the reflected white light and fluorescence emission to the image acquisition module without a separate accessory module.

One variation of the surgery-specific module may include a surgical microscope 120*d* with the appropriate magnification and working distance for microsurgical applications. The surgical microscope may be configured for electronic image capture with the optical image acquisition module, and/or may also provide a direct viewing binocular option.

Another variation of the surgery-specific module may include a laparoscope/endoscope 120*b*, such as for minimally invasive or endoscopic surgeries.

Another variation of the surgery-specific module may include an open field illumination/imaging module 120*c*, such as for laparotomy/open field surgery. In some variations, the open field illumination/imaging module may be handheld and/or supported by a positioning/supporting arm or robotic arm 130*c*. In these variations, the handheld aspects, and/or the positioning arm or robotic arm may be provided in an accessory module (or integrated as part of the surgery-specific module).

Another variation of the surgery-specific module may include a stereoscopic videoscope 120*a*, such as for robotics applications. For example, a stereoscopic device may interconnect two image acquisition modules to a stereoscopic laparoscope, either with or without a separate optical coupler (which may be an accessory module or integrated in the surgery-specific module). In some variations, the stereoscopic device may include a dedicated stereoscopic camera.

Another variation of the surgery-specific module may include a scintigraphy module 120*e*. Further variations include modules designated or specially-designed for other suitable kinds of surgical applications.

In some variations, the surgery-specific modules and optical image acquisition module may be integrated. For instance, the camera optics and sensor assembly of the optical image acquisition module may be integrated with the surgery-specific module (e.g., laparoscope/endoscope module, surgical microscope module, wide field illumination/imaging module, stereoscopic laparoscope module for robotic surgery applications, etc.). In these variations, at least some of the same remaining operative modules (and the one or more accessory modules to interconnect these with the factory-integrated image acquisition and surgery-specific modules) may be utilized.

Accessory Modules

One or more accessory modules 130 may be interconnected with the operative and/or surgery-specific modules and provide additional functions. One variation of an accessory module includes an optical connection or light guide 130*a* (e.g., fiber optic, liquid light guide, etc.) for delivering light from the illumination module to the surgery-specific module. Another variation of an accessory module includes an optical connection or light guide (e.g., fiber optic, liquid light guide, etc.) for delivering light captured by the surgery-specific module to the imaging acquisition module. Another variation of an accessory module includes a coupler 130*b* that couples one or more of the surgery-specific modules (e.g., 120*a*, 120*b*, 120*c*, and/or 120*d*, etc.) to the optical image acquisition module 220. The coupler may, for example, mount to the surgery-specific module and the optical image acquisition module to indirectly join these two modules together. The coupler may or may not include an optical connection or light guide for delivering light to and/or from the surgery-specific module. Yet other variations of accessory modules may provide mechanical support (e.g., support arm 130*c*) or enclosure for one or more of the modules, aiding in the interconnection/adaptation of other modules, and/or other suitable functions not provided by the operative modules or surgery-specific modules.

Data Modules

The system may include one or more data modules 140 that receive image data. As shown in FIG. 1, one variation of a data module includes a video display 140*a* or other monitor (e.g., computer monitor, touch screen, etc.) that enables display of substantially real-time and/or recorded image and data to a clinician, patient, or other user. Another variation of a data module includes a recorder 140*b* (e.g., hard disk, flash memory, other tangible non-transitory computer readable medium, etc.) or other data storage device that can store images and/or other data. Another variation of a data module includes a printer 140c for creating hard copies of images and/or other data for further visualization, archiving, record-keeping, or other purposes. Yet another variation of a data module includes a picture archiving and communication system 140d (PACS) which may, for example, store data in standard Digital Imaging and Communications in Medicine (DICOM) format or any other suitable format. Other variations of data modules include systems for communicating and/or storing image data in any suitable manner.

Operation of the Fluorescence Imaging System

The operation of an intraoperative fluorescence imaging system, such as a system configured as an interconnected set of operative modules, one or more surgery-specific modules, and one or more accessory modules as described above, will now be described. In some variations, the imaging system may be a multi-mode system in that it can operate in any one of a non-fluorescence mode, fluorescence mode, and a combined fluorescence and non-fluorescence mode. Each of these modes is described below. In other variations, the imaging system may be a single mode system that operates only in the fluorescence mode, which may be similar to the fluorescence mode in the multi-mode system operation described below.

In a non-fluorescence mode of operation, the fluorescence imaging system may provide real time full color visible (white) light image data for display on a video monitor and/or for recording. In this mode, the illumination module provides broad visible spectrum light output (e.g., via solid state components such as laser diodes, filtered LEDs, filtered non-solid state light sources, etc., or a combination of these) which may be coupled to and transmitted by the surgery-specific module and projected onto the surface to be illuminated. The broad visible spectrum light reflected from the illuminated surface may be captured by the surgery-specific module and transmitted to the image acquisition module that transduces the image data. The transduced electronic image signal may be subsequently transmitted to the image processor that processes and outputs for display and/or recording in real time, with negligible latency. The displayed and/or recorded reflected white light image data may have a high color fidelity, such that it is a highly accurate color depiction of the surface that is reflecting the light. These images may be displayed and/or recorded in full color and at high definition (HD) or ultra-high definition (UHD or 4K) resolution (or other suitable resolution). This full color, white light imaging mode may be optional for some surgeries, such as those in which the surgeon has a direct line of site to the surgical area and/or does not require an anatomical context in which to assess the fluorescence image data.

In a fluorescence mode of operation, the fluorescence imaging system provides real time fluorescence emission image data for display on a video monitor and/or for recording. In this mode, the illumination module provides fluorescence excitation light output (e.g., via solid state components such as laser diodes, filtered LEDs, filtered non-solid state light sources, etc. or a combination of these) which may be coupled to and transmitted by the surgery-specific module and projected onto the surface to be illuminated. The fluorescence emission emanating from the excited fluorophores within the illuminated area may be captured by the surgery-specific module and transmitted to the image acquisition module that transduces the image data. The transduced electronic image signal may be subsequently transmitted to the image processor that processes and outputs for display and/or recording in real time, with negligible latency. The displayed and/or recorded fluorescence emission image data may be monochrome (e.g., black and white or grayscale) or pseudo-colored (e.g., via a color map based on intensity or some other signal parameter) and may be displayed and/or recorded in a monochrome or pseudo-colored fashion at high definition (HD) or ultra-high definition (UHD or 4K) resolution (or other suitable resolution). This fluorescence emission imaging mode may be a stand-alone mode for surgeries in which the surgeon has a direct line of sight to the surgical area and/or does not require an anatomical context in which to assess the fluorescence image data.

In a combination non-fluorescence and fluorescence mode of operation, the fluorescence imaging system simultaneously provides the options of (a) real time full color visible (white) light image data, (b) real time fluorescence emission image data, and (c) a combination of real time full color visible (white) light image data and real time fluorescence emission image data for display on a video monitor and/or for recording. In this combination mode, the illumination module operates simultaneously in two illumination modes to provide both broad visible spectrum light output and fluorescence excitation light output (e.g., via solid state components such as laser diodes, filtered LEDs, filtered non-solid state light sources, etc. or a combination of these). This illumination may be transmitted by the surgery-specific module and projected onto the surface to be illuminated. The visible light output and the fluorescence light output are pulsed so that different wavebands are illuminating the area to be imaged at different times. The pulsing scheme may be such that the broad visible spectrum light and fluorescence excitation light are both pulsed or that only one of the illumination modes (either the broad visible spectrum light or the fluorescence excitation light) is pulsed. Alternatively, some portion of either the broad visible spectrum light and/or fluorescence excitation light may be pulsed.

As a result of the pulsed illumination modes, the illumination of the area to be imaged by broad visible spectrum light and fluorescence excitation light may be composed of any of four kinds of illumination: (1) where the light output is pulsed for both illumination modes such that the illumination modes are partially or completely separated in time; (2) where the light output for one illumination mode is continuous and the other mode is pulsed; (3) where a wavelength portion of the light output for one illumination mode is continuous and the other mode is pulsed; and (4) where the light output is continuous for both illumination modes. The surgery-specific module captures the broad visible spectrum light reflected from the illuminated surface and the fluorescence emission emanating from the fluorophores within the illuminated area, and transmits this reflected light and fluorescence emission to the image acquisition module that transduces the image data. The transduced electronic image signal is subsequently transmitted to the image processor, which separates the image signal associated with the reflected broad visible spectrum light from the image signal associated with the fluorescence emission. The processing scheme in the image processor is synchronized and matched to the pulsing scheme in the illumination module (e.g., via the controller) to enable this separation of the image signals. The rate of pulsing and image processing may be such that the processed image signals are output for display and/or recording in real time, with negligible latency.

Figures 17A, 17B:
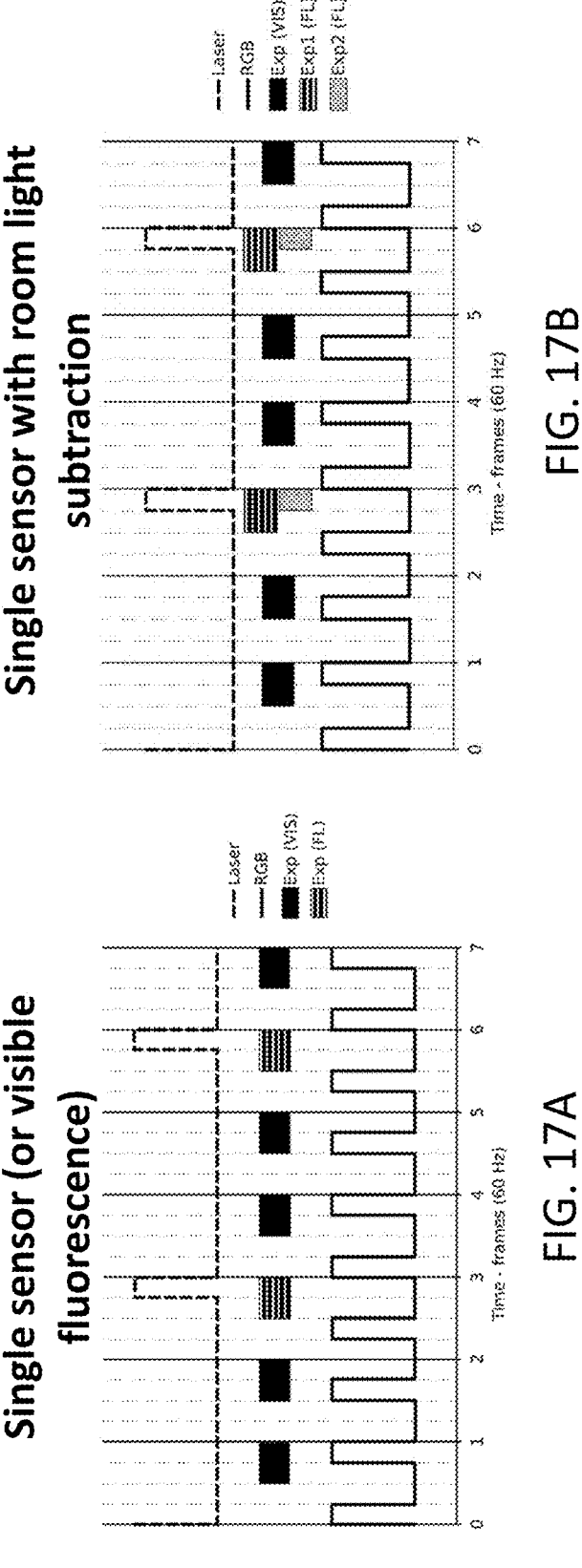
FIGS. 17A-17C are diagrams of exemplary illumination and image acquisition timing schemes for a fluorescence imaging system.
Figure 17C:
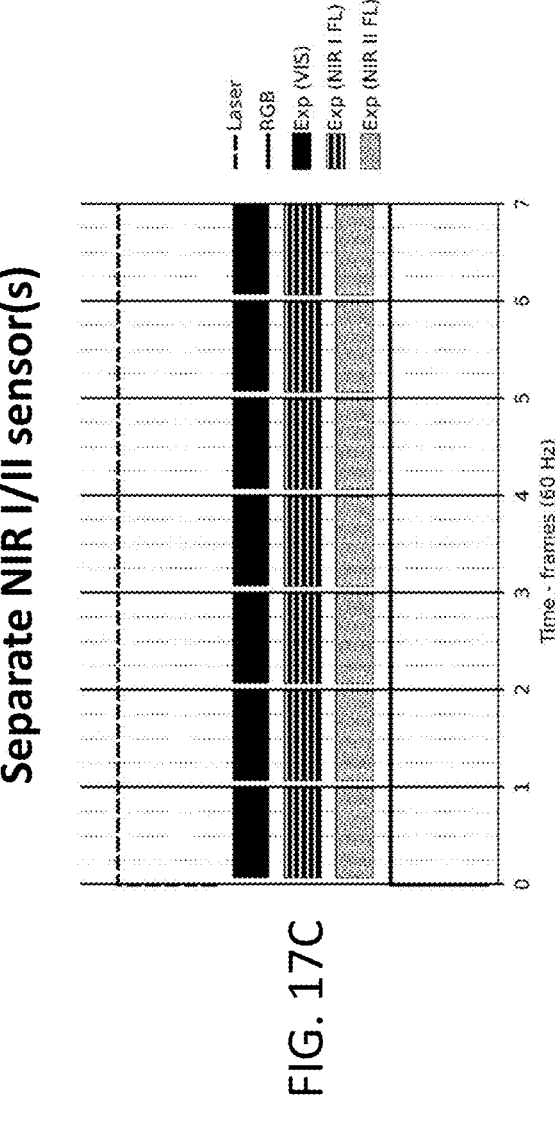

For example, as shown in FIGS. 17A and 17B, in some variations (e.g., in which the image acquisition module includes a single image sensor that may receive visible light and/or fluorescence emission), the pulsed light output for both the visible light ("RGB") and fluorescence ("Laser") illumination modes may be synchronized with the acquisition of visible light ("Exp (VIS)") and fluorescence emission ("Exp (FL)"), respectively, by the image sensor. As shown in FIG. 17B, in some variations the system may further compensate for background illumination (e.g., room lighting) in substantially similar wavelengths as the fluorescence emission. In these variations, visible light and fluorescence emission imaging may be performed while reducing the risk of confounding the fluorescence emission with background lighting. For instance, the system may include at least one image sensor configured to detect background light corresponding to the same or similar wavelengths as the fluorescence emission, such that the signal for this detected background light can be subtracted from signals provided by any sensor that detects the fluorescence emission. Alternatively, as shown in FIG. 17C, in some variations (e.g., in which the image acquisition module includes one or more fluorescence emission image sensors in addition to a reflected visible light image sensor), continuous light output for both the visible light and fluorescence illumination modes may correspond with the separate, continuous acquisition of visible light ("Exp (VIS)"), NIR-I fluorescence emission ("Exp (NIR I FL)"), and/or NIR-II fluorescence emission ("Exp (NIR II FL)") by the image sensors. Additional examples of such pulsing and image processing schemes have been described in U.S. Pat. No. 9,173,554, filed on Mar. 18, 2009 and titled "IMAGING SYSTEM FOR COMBINED FULL-COLOR REFLECTANCE AND NEAR-INFRARED IMAGING," the contents of which are incorporated in their entirety by this reference. However, other suitable pulsing and image processing schemes may be used.

The image data from the broad visible spectrum light may be processed by any suitable color image processing methods according to the nature of the image acquisition module. In variations in which the image acquisition module includes a color camera with a single solid state image sensor and a color filter array deposited on the sensor surface, the image processing method may include de-mosaicing the color image signal, followed by amplification, A/D conversion, and/or storage in color image memory. The typical (but not the only) signal format after such processing is luminance/chrominance ($Y_c$, $c_r$ $c_b$) format. In variations in which the image acquisition module includes a color camera with three solid state image sensors mounted on a Philips (RGB) prism (or other beam splitting element), the image processing method may include receiving a direct readout of the red, green, and blue color image from the camera, followed by amplification, A/D conversion, and/or storage in color image memory. The typical (but not the only) signal format after such processing is luminance/chrominance ($Y_c$, $c_r$ $c_b$) format.

The processed image data may be output in a multi-window (e.g., tiled, matrix) display and/or recorded in high definition (HD) or ultra-high definition (UHD or 4K) resolution (or any suitable resolution), with negligible latency. The color image data and fluorescence image data may be simultaneously output in separate channels for display and/or recording. Similar to the white light images in the non-fluorescence-only mode, the displayed and/or recorded reflected white light image data may have a high color fidelity, such that it is a highly accurate color depiction of the surface that is reflecting the light. Similar to the fluorescence images in the fluorescence-only mode, the displayed and/or recorded fluorescence emission image data may be monochrome (e.g., black and white or grayscale) or pseudo-colored (e.g., via a color map based on intensity or some other signal parameter) and may be displayed and/or recorded in a monochrome or pseudo-colored fashion. Additionally or alternatively, the white light image data and the fluorescence image data may be overlaid or otherwise combined. For example, the fluorescence emission image data may be used to modify the chrominance ($c_r$, $c_b$) in the white light image data such that pixels with higher fluorescence signal intensity are increasingly saturated by a non-naturally occurring color (e.g., green in biological systems).

Method for Fluorescence Imaging

In some variations, the method for fluorescence imaging an object may include emitting white light, emitting excitation light in a plurality of excitation wavebands for causing the object to emit fluorescent light, directing the white light and excitation light to the object and/or collecting reflected white light and emitted fluorescent light from the object, blocking substantially all light in the excitation wavebands and transmitting at least a substantial portion of the reflected white light and/or the fluorescent light, and receiving the transmitted reflected white light and fluorescent light on an image sensor assembly. In some variations, the white light and excitation light may be directed to the object and/or reflected white light and emitted fluorescent light may be collected from the object by a component (e.g., an inter-changeable, surgery-specific component). In some variations, the reflected white light and fluorescent light received at the image sensor assembly may be temporally and/or spatially multiplexed. In some variation, excitation light is emitted in a plurality of non-overlapping excitation wavebands for causing the object to emit fluorescent light.

In some variations, the method may include receiving image signals from the image sensor assembly, and processing the received image signals to generate images from the received image signals. In some variations, the method may include controlling the white light provider and/or excitation light provider to operate in a non-fluorescence mode, a fluorescence mode, or a combined non-fluorescence and fluorescence mode. In these variations, the processing steps may include separating image signals from the image sensor assembly into a first set of image signals associated with the reflected white light and a second set of image signals associated with the fluorescent light. The processing steps may further include generating a white light image based on the first set of image signals and a fluorescence emission image based on the second set of image signals.

Other aspects of the method include performing any of the various steps and functions described above with respect to the operation of the fluorescence imaging system with a configurable platform, and/or the functions of various components therein.

Multiplexed Fluorescence Imaging System

Figure 5:
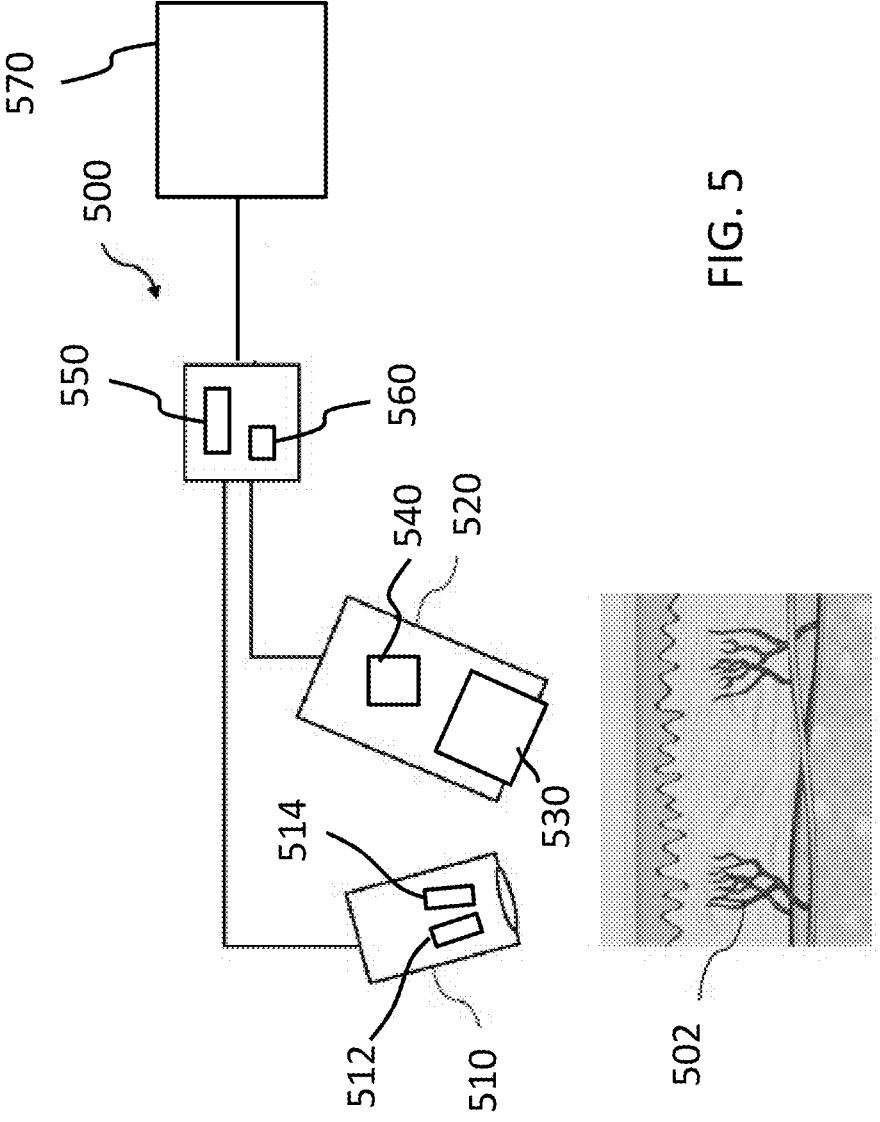
FIG. 5 is a schematic illustration of a multiplexed fluorescence imaging system.

As shown in FIG. 5, in some variations, a multiplexed fluorescence imaging system 500 for imaging an object includes: a light source assembly 510 including a white light provider 512 that emits white light and an excitation light provider 514 that emits excitation light in a plurality of excitation wavebands for causing the object 502 to emit fluorescent light; a camera 520 with at least one image sensor 540 that receives reflected white light and emitted fluorescent light from the object; an optical assembly 530 located in the optical path between the object and the image sensor, wherein the optical assembly 530 includes a first optics region that projects the reflected white light as a white light image onto the image sensor and a second optics region that reduces the image size of the fluorescent light, spectrally separates the fluorescent light, and projects the separated fluorescent light as fluorescence images onto different portions of the image sensor; and an image processor 550 that electronically magnifies the fluorescence images. As a result, the white light image and multiple fluorescent light images may be simultaneously projected onto an image plane (for one or more image sensors) in a single camera in a spatially and temporally multiplexed manner. As a result, the multiplexed fluorescence imaging system 500 can, simultaneously and in real time, acquire fluorescence emission images at multiple wavelengths within the visible and NIR spectrum, as well as acquire full color reflected light (white light) images. Furthermore, this functionality may be achieved with the use of only a single camera, thereby reducing bulk of the overall system and enabling the system to be used in a greater variety of surgical applications. In some variations, the excitation light provider 514 emits excitation light in a plurality of non-overlapping excitation wavebands for causing the object 502 to emit fluorescent light Although the components of the system are primarily described below as grouped in particular assemblies, in some variations, the various components may be organized and grouped in any suitable manner (that is, the various components described herein may be combined and arranged in assemblies and subassemblies different from those described herein). Furthermore, in some variations, the components may be combined in a single physical system (e.g., an imaging system for use in a clinical setting). In other variations, some or all of the components (e.g., the image processor) may be located separate from the other components, such as on a computer system at an off-site location that is remote from a clinical site or otherwise not embodied in the same physical unit as the other components.

Light Source Assembly

As shown in FIG. 5, in some variations, the multiplexed fluorescence imaging system 500 may include a light source assembly 510 including a white light provider 512 and an excitation light provider 514.

The white light provider 512 emits white light for illumination of the object to be imaged. In some variations, the white light provider includes one or more solid state emitters such as LEDs and/or laser diodes. For example, the white light provider may include blue, green, and red LEDS or laser diodes that in combination generate visible (white) light illumination. In some variations, these light sources are centered around the same wavelengths (e.g., ~460 nm, ~530 nm, and ~635 nm) around which the camera (described further below) is centered. For example, in variations in which the camera includes a single chip, single color image sensor having an RGB color filter array deposited on its pixels, the blue, green, and red light sources may be centered around the same wavelengths around which the RGB color filter array is centered. As another example, in variations in which the camera is a three-chip, three-sensor (RGB) color camera system, the blue, green, and red light sources may be centered around the same wavelengths around which the blue, green, and red image sensors are centered.

The excitation light provider 514 emits fluorescence excitation light in a plurality of excitation wavebands that are non-overlapping. One or more of the excitation wavebands may be selected such that it falls outside of the visible white light spectrum used for imaging (between about 450 nm and about 650 nm), so that a fluorescence excitation light blocking filter (described further below) substantially blocking any remitted/reflected excitation wavelengths in the imaging path does not also substantially block white light reflected from the object, and therefore will not substantially interfere with the generation of a white light image. In some variations, at least some of the excitation wavebands may at least partially overlap with the visible spectrum, which may result in some compromise of reflected white light ultimately imaged (since some of the reflected white light may be blocked simultaneously with any remitted/reflected excitation light whose wavelength overlaps with the reflected white light), but such excitation wavebands may nevertheless be suitable. For example, in variations in which the excitation light provider emits excitation light in a waveband centered at about 470 nm, a fluorescence excitation light blocking filter that substantially blocks any remitted/reflected excitation light in that waveband may also at least partially block cyan wavelengths, which is only a segment of the entire white light spectrum.

In some variations, the excitation light provider 514 may emit light in excitation wavebands centered at (i) about 670 nm to excite Cy5, Cy5.5, Methylene Blue, porphysomes, etc.; (ii) about 770 nm to excite NIR fluorophores such IRDye800, etc. and/or NIR-II fluorophores such as IR-PEG, etc.; (iii) about 805 nm to excite ICG (Indocyanine Green) or analogues such as IfCG, etc. and/or NIR-II fluorophores such as IR1061 or CH1100, etc.; (iv) about 405 nm to excite tissue auto-fluorescence, etc.; and/or (v) about 470 nm to excite Fluorescein, Vitamin B2, etc. In one exemplary embodiment, the excitation light provider emits light in excitation wavebands (i), (ii), and (iii) described above. In another exemplary embodiment, the excitation light provider emits light in excitation wavebands (i), (ii), (iii), and one or both of wavebands (iv) and (v). However, the excitation light provider may emit light in any number and any combination of wavebands (i), (ii), (iii), (iv), and (v). The excitation light provider may additionally or alternatively emit light centered around any suitable wavelength.

In some variations, the excitation light provider 514 includes solid state light sources, such as laser diodes or LEDs. Solid state elements may have a number of advantages in the multiplexed fluorescence imaging system described herein. In particular, solid state elements can be rapidly switched on and off, and their duty cycle (time on vs. time off) can be altered electronically. Additionally, laser diodes emit light along relatively narrow spectral lines which can be effectively and precisely blocked with one or more commensurately narrow excitation light blocking filters in the imaging path when Stokes shifts are short, such that the one or more excitation light blocking filters do not substantially interfere with the collection of other wavelengths when imaging. Finally, solid state light sources provide various other practical advantages including lifetime, cost, energy efficiency, ease of adjusting color preferences, etc. However, the excitation light provider may additionally or alternatively include non-solid state light sources in any suitable combination.

In some variations, the light source assembly 510 may be configured as a series of white light and excitation light emitters whose collimated outputs are folded into a combined optical path by one or more dichroic mirrors and/or other suitable optical components. The excitation light sources (e.g., laser diodes, etc.) may be fiber-coupled so that the light output from the distal end of the optical fibers can be bundled or otherwise easily positioned for collimation and folding into a single optical path. This arrangement may enable a relatively compact configuration that contributes to a more compact fluorescence imaging system, and which may be more easily cooled for thermal management purposes (e.g., by using a single heat spreader plate). However the outputs of the white light and excitation light emitters may be organized and transmitted out of the light source assembly in any suitable manner.

Optical Assembly and Camera

As shown in FIG. 5, the multiplexed fluorescence imaging system may include an optical assembly 530 and a camera system 520 with at least one image sensor assembly 540. The optical assembly 530 may transmit, in an illumination optical path, the white light and the excitation light from the light source assembly to the object being imaged. The optical assembly 530 may also receive, in an imaging optical path, reflected visible (white) light and emitted fluorescent light in the corresponding wavebands for the fluorophores in the object that are excited by the light source assembly. In some variations, the optical assembly 530 may manipulate the reflected white light and/or fluorescence light as described further below, and output the light to the camera system. After receiving the white light and fluorescent light, the camera system may transduce the received light into electrical image signals for the image processor (described below) to process.

The optical assembly 530 may take various form factors depending on the surgical application. For example, the optical assembly may include a lens assembly for wide field (e.g., open surgery) illumination and imaging. As another example, the optical assembly may include a surgical microscope for illuminating and imaging a microscopic field of view. As another example, the optical assembly may include an endoscope for illuminating and imaging a surface interior to the body through a small surgical opening or via a natural orifice/lumen. In some variations, the optical assembly may be interchangeable, similar to one or more of the surgery-specific modules described above in the fluorescence system having a configurable platform. Due to the size and/or weight of the light source assembly, the light from the light source assembly may be generally transmitted to the optical assembly by a light guide (e.g., optical fiber, liquid light guide, etc.), but the light from the source assembly may be transmitted to and from the optical assembly in any suitable manner.

In some variations, the optical assembly 530 and the camera system 520 may be separate components. For example, the optical assembly may be part of a surgical microscope with a removable camera. As another example, the optical assembly may be part of a rigid laparoscope with a camera mounted proximally (e.g., camera mounted on the eyepiece, etc.). In other variations, the optical assembly 530 may be integrated with the camera system 520. For example, the optical assembly may be integrated with a wide field camera system for use in open surgery/laparotomy, where the optical assembly and camera system may be mounted on a support arm, be hand held, or be positionable in any suitable manner. As another example, the optical assembly may be integrated in a video endoscope in which the camera is mounted at the distal end of the scope.

As shown in the exemplary variations depicted in FIGS. 6A, 6B, 7, 8, and 16A-16C, the combination of the optical assembly and camera, whether separate or integrated, may include various optical components located in the optical path between the object and one or more image sensors in the camera. In particular, the optical assembly may include an optics region that projects the reflected white light as a white light image onto the image sensor in the camera, and an optics region that reduces the image size of the fluorescence light, spectrally separates the fluorescent light, and projects the separated fluorescence light as fluorescence images onto different portions of the image sensor in the camera. As a result, the white light image and multiple fluorescent light images may be simultaneously projected onto an image plane (with one or more image sensors) in a single camera, in a spatially and temporally multiplexed manner. The optical assembly may include additional optical components such as beam splitters, mirrors, etc. that also manipulate white light and/or emitted fluorescent light before the light is projected onto the image sensor.

Figure 6A:
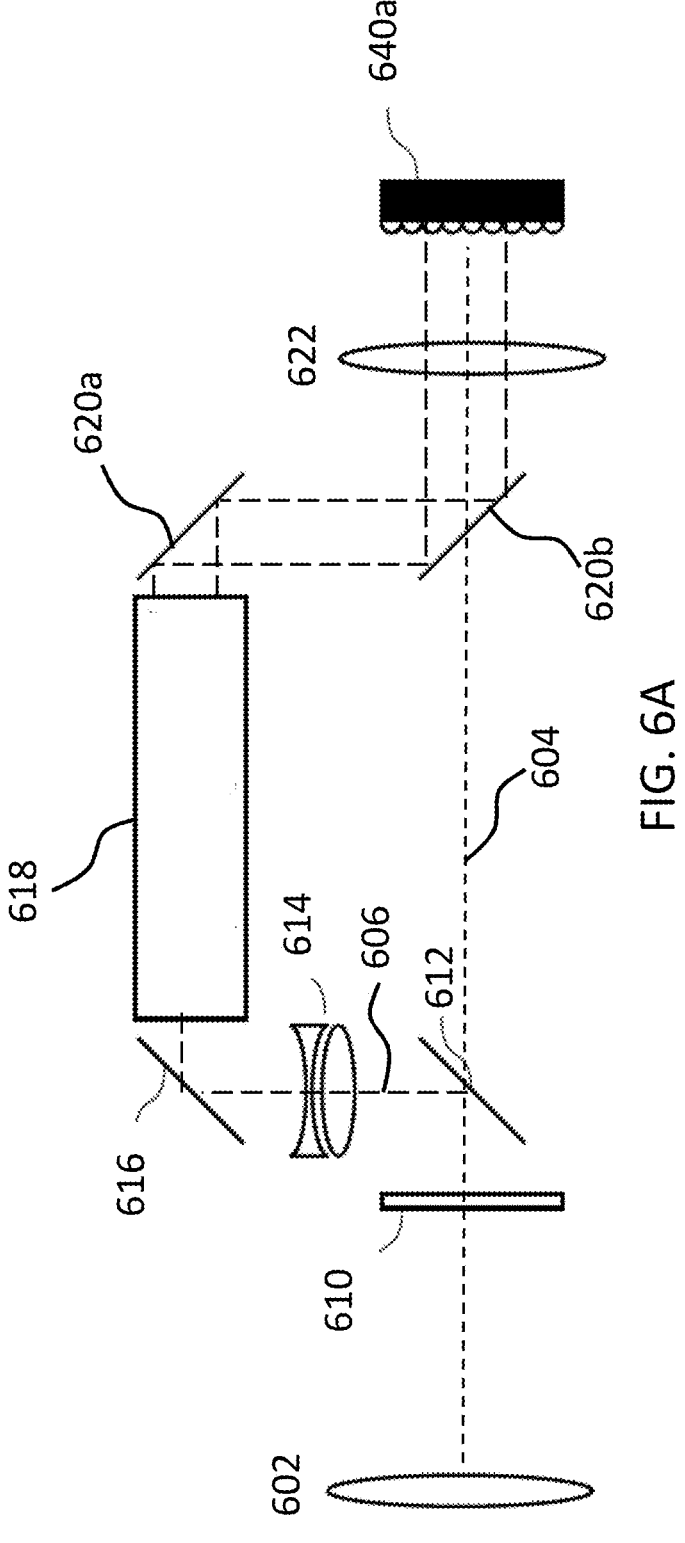
FIG. 6A is an illustrative depiction of one variation of an exemplary optical assembly in a fluorescence imaging system.
Figure 6B:
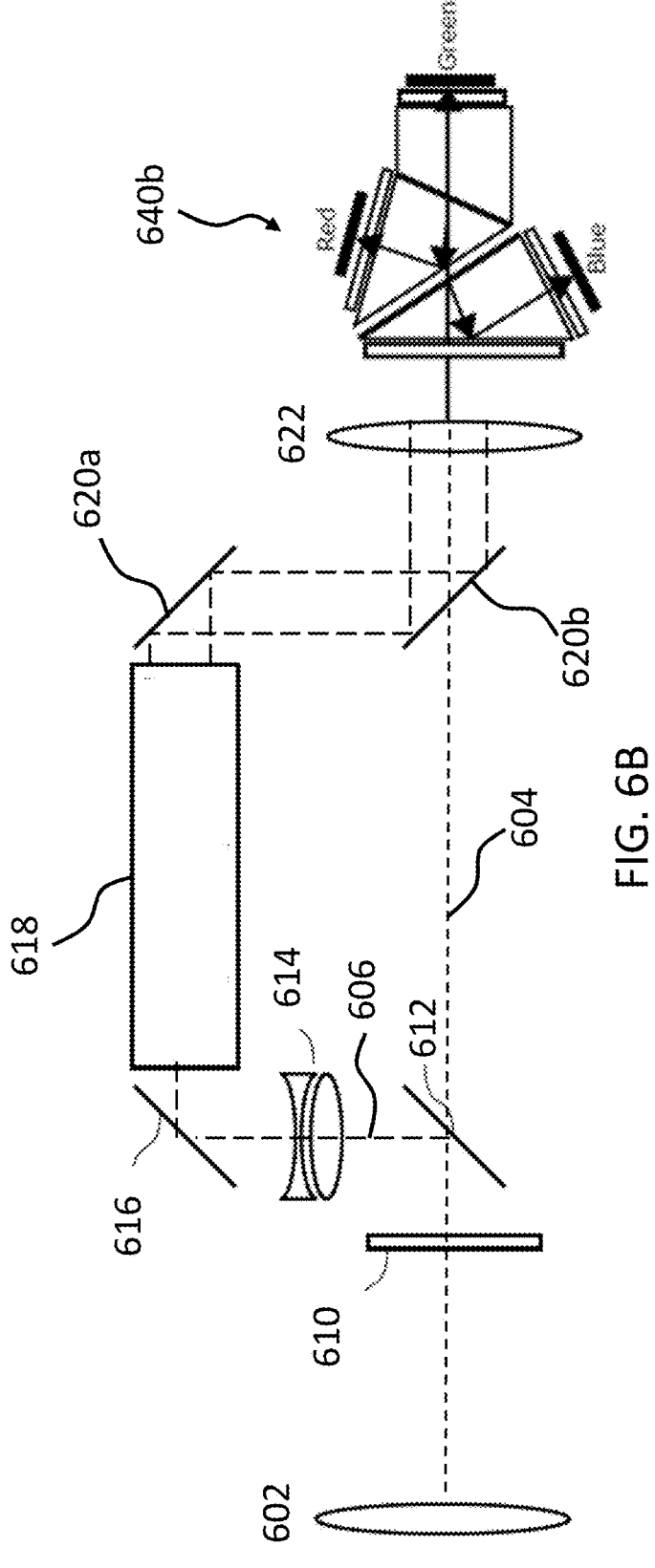
FIG. 6B is an illustrative depiction of another variation of an exemplary optical assembly in a fluorescence imaging system.

As shown in FIGS. 6A-6B, in some variations, the optical assembly may include a field lens 602 and/or other input optics that capture light traveling in the imaging path from the object toward the camera. This light may include, for example, reflected white light illumination, reflected or remitted excitation light illumination, emitted fluorescent light originating from excited fluorophores in the object, and/or other light in other wavebands that are traveling in the imaging path.

As shown in FIGS. 6A-6B, in some variations, the optical assembly may include a fluorescence excitation light blocking filter 610 that substantially exclude excitation light from reaching the image sensor. The fluorescence excitation light blocking filter may be a multi-band notch filter that blocks substantially all fluorescence excitation light produced by the light source assembly (which may be reflected or remitted from the object), but passes at least a substantial portion of visible (white) light for color imaging and at least a substantial portion of the fluorescence emission bands of fluorophores excited by the fluorescence excitation light. The filter 610 may be located in the optical imaging path between the fluorophores in the object and the one or more image sensors in the camera system, such that only the reflected white light and the emitted fluorescent light will be projected onto the one or more image sensors. In some variations, the filter may be located in a portion of the optical path in which the light rays have a minimal cone angle. In some variations, the filter may be a multi-layer interference filter, though in other variations the filter may have any suitable construction.

The optical assembly may include additional optics regions for performing various beam shaping functions described below. In some variations, the optical assembly may include a dichroic or other kind of beam splitter that may separate the light transmitted by the fluorescence excitation light blocking filter into white light and fluorescent light components. In particular, the beam splitter may divide the optical path into at least two legs or branches: one branch for reflected visible (white) light that is transmitted by the fluorescence excitation light blocking filter, and at least one branch for emitted fluorescence light that is transmitted by the fluorescence excitation light blocking filter. However, the beam splitter 612 may further divide (or not further divide) the fluorescent light transmitted by the fluorescence excitation light blocking filter into multiple fluorescent optical paths. In one variation, as shown in FIGS. 6A and 6B, a dichroic splitter 612 may transmit visible light 604 and reflect fluorescence light 606, thereby diverting fluorescence light to a different path (e.g., one that is offset from the optical axis of the image sensor).

As shown in FIGS. 6A-6B, in some variations, the optical assembly may include demagnification optics 614 that reduce the image size of the emitted fluorescent light. The demagnification optics may include, for example, one or more lens systems that reduce the size of the fluorescence images. Once reduced, the multiple fluorescence images can subsequently be detected simultaneously with the white light image by the same image sensor assembly, as further described below. In an exemplary embodiment, the demagnification optics reduce the image dimensions of the emitted fluorescent light by an approximate factor of 2, thereby causing the dimensions of each of the fluorescence images to be about one-half the corresponding dimensions of the white light image (i.e., such that each of the fluorescence images has an image area about one-fourth the image area of the white light image). In other variations, the demagnification optics may reduce the image dimensions of the emitted fluorescent light by any suitable factor, which may or may not depend on the number of excitation/emission wavebands used by the system. In some instances, the demagnified fluorescent light may be redirected or otherwise shaped by other optical components such as mirror 616 that redirects the fluorescent light toward beam splitter 618. However, in variations in which multiple fluorophores having non-overlapping emitted light wavebands are excited by a common excitation wavelength, then the beam splitter 618 may divide the fluorescence emission into light paths corresponding to the distinct emission wavebands.

Figure 13B:
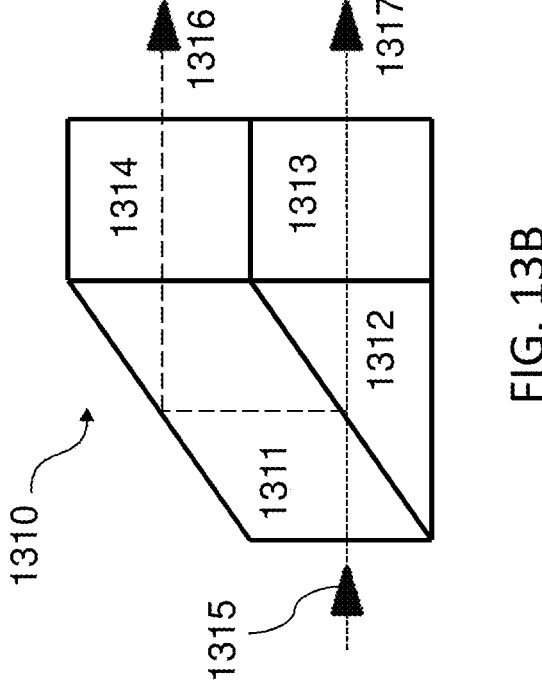
FIGS. 13A and 13B are perspective and right-side views of a schematic of a vertical beam-splitting prism.
Figure 13A:
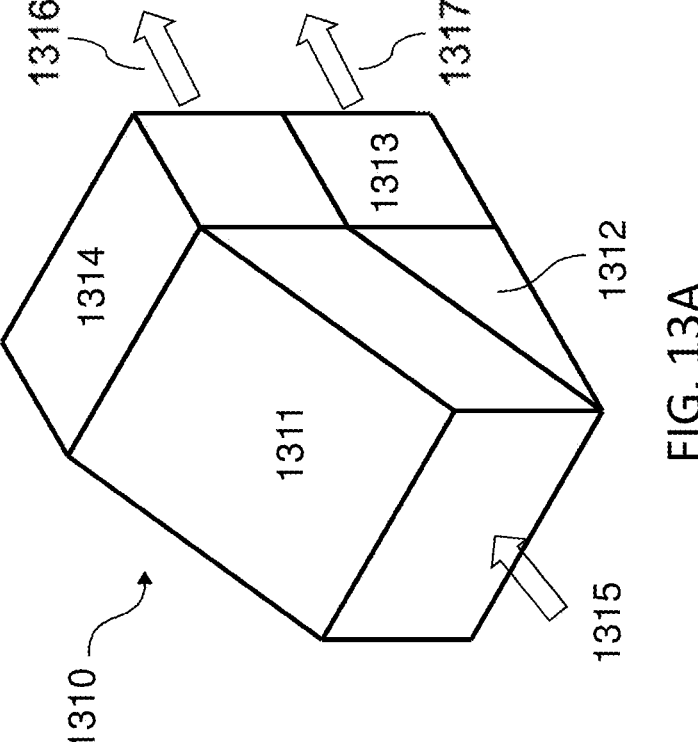
Figures 14A, 14B:
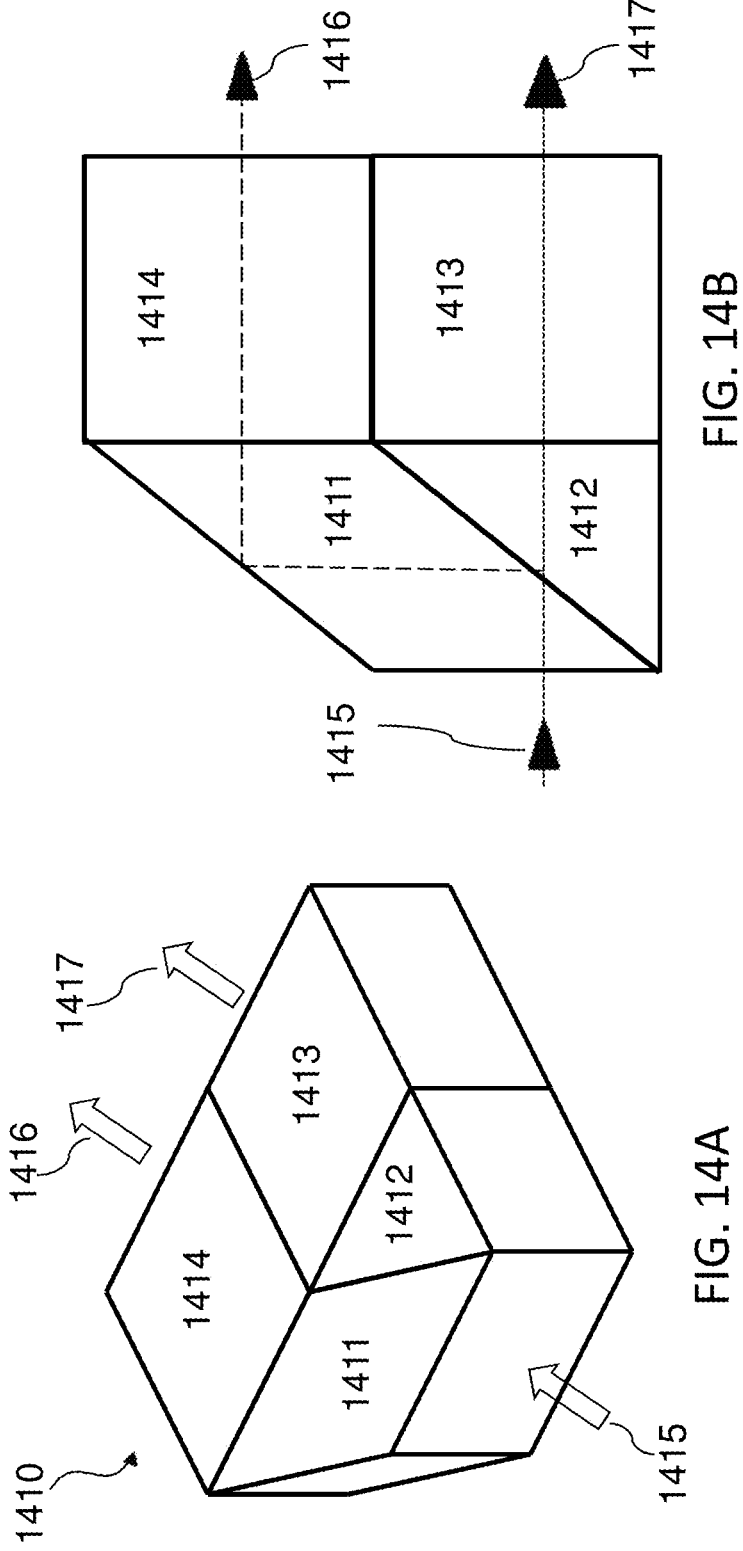
FIGS. 14A and 14B are perspective and top views of a schematic of a horizontal beam-splitting prism.

As shown in FIGS. 6A-6B, in some variations, the optical assembly may include one or more additional beam splitters 618 that further separate the fluorescence emission optical path following the demagnification optics. The beam splitters 618 may include one or more dichroic mirrors, prisms, other suitable beam splitters, or any suitable combination or assembly thereof. The beam splitter 618 may be designed and/or selected to spectrally separate the fluorescence emission generated by the excitation wavelengths (e.g., at ~670 nm, ~770 nm and ~805 nm, etc.) into separate, demagnified fluorescent image paths. For instance, a beam-splitting prism may include multiple portions (e.g., components) that have dimensions and/or include a material chosen (based on factors such as refractive index) in order to equalize the optical path length for all split beam paths. For example, a vertical beam-splitting prism may be used to divide the fluorescence emission into multiple light paths to be offset vertically. As shown in FIGS. 13A and 13B, a vertical beam-splitting prism 1310 may include multiple portions (e.g., 1311, 1312, 1313, and 1314) that spectrally separate incident light 1315 into at least two vertically offset light paths 1316 and 1317. Additionally or alternatively, a horizontal beam-splitting prism 1410 may be used to divide the fluorescence emission into multiple light paths to be offset horizontally. As shown in FIGS. 14A and 14B, a horizontal beam-splitting prism may include multiple portions (e.g., 1411, 1412, 1413, and 1414) that spectrally separate incident light 1415 into at least two horizontally offset light paths 1416 and 1417.

Figure 15:
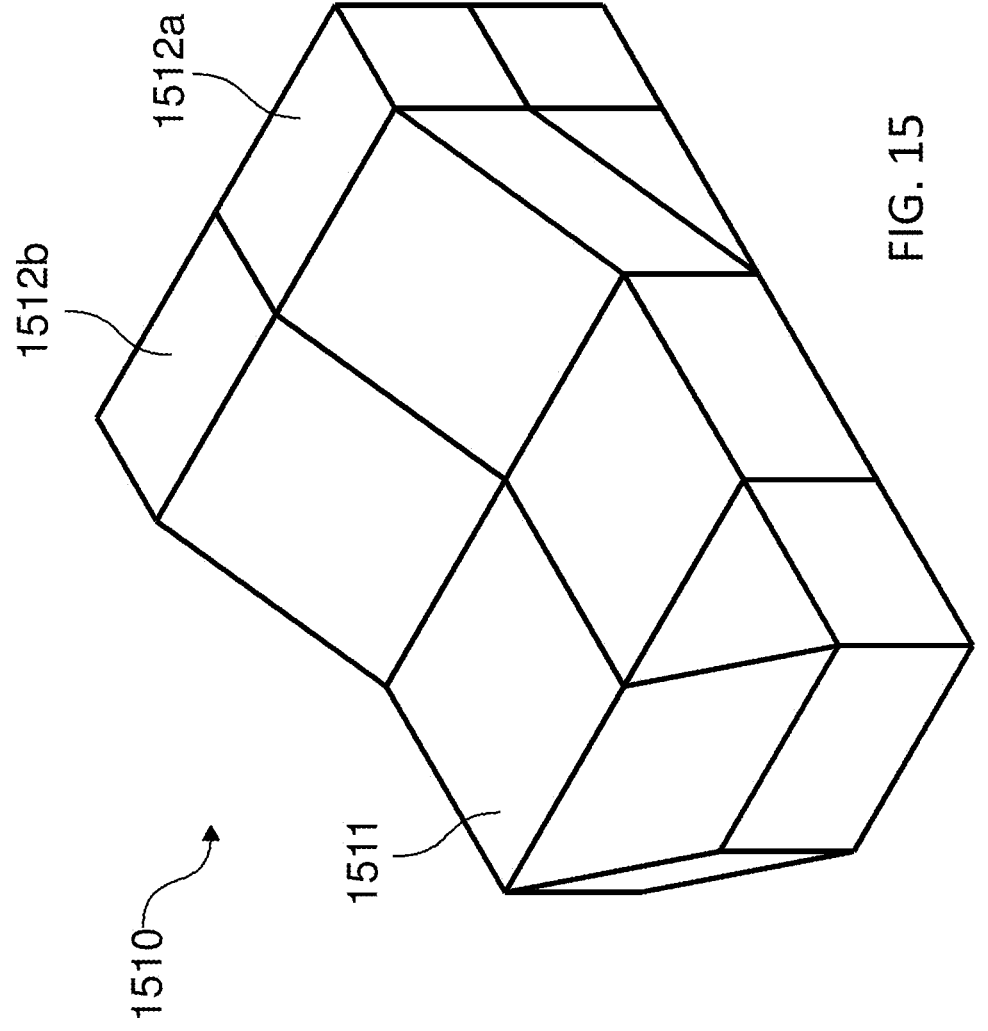
FIG. 15 is a perspective view of a schematic of a beam-splitting prism assembly.

In an exemplary embodiment, the beam splitter 618 divides the fluorescence emission into four light paths corresponding to four excitation wavelengths that generated the fluorescence emission. In some variations, this may be achieved with a beam-splitting prism assembly 1510 including a combination of prism beam splitters. For example, as shown in FIG. 15, a beam-splitting prism assembly 1510 may include one horizontal beam-splitting prism 1511 (similar to horizontal beam-splitting prism 1410) in combination with two vertical beam-splitting prisms 1511a and 1511b (similar to vertical beam-splitting prism 1310). In particular, the horizontal beam splitting prism 1511 may split an incident fluorescent light branch into two horizontally offset fluorescent light branches, each of which is received by a respective vertical beam-splitting prism 1512a or 1512b. Each of the two vertical beam-splitting prisms 1512a and 1512b may subsequently split its received fluorescent light branch into two vertically offset fluorescent light branches, thereby resulting in four fluorescence light branches. These four fluorescent light branches may then be directed onto four quadrants of the image plane at an image sensor.

In some variations, the optical assembly may include an alignment component system containing at least one dichroic element or other alignment component that realigns the multiple fluorescence emission optical paths and the visible light optical path prior to the image sensor(s), such that separate fluorescence images are projected onto different portions of the image plane at the sensor. As shown in FIGS. 6A and 6B, in variations in which the fluorescence light was previously diverted away from the visible light, such an alignment component system may fold fluorescence emission optical paths back into the visible light optical path. In particular, the alignment component system may include mirror 620a and dichroic mirror 620b that reflect the multiple fluorescence branches into the same optical path as the white light branch 604. As a result, the alignment components may cause the white light and the spectrally separated fluorescent light to follow the same optical path toward the image sensor(s) 640, and the optical assembly as a whole may project the full-sized white light image and the demagnified fluorescence images simultaneously onto the image sensor(s) in the camera. In an exemplary embodiment (e.g., where the fluorescence images are demagnified by an approximate factor of two), the alignment component system may cause the four demagnified fluorescence images to be projected onto four (4) quadrants of the image plane at the sensor(s) 640. However, the alignment component system may cause the fluorescence images to be projected on any suitable portions of the image plane.

As shown in FIGS. 6A-6B, in some variations, the optical assembly may include projection optics 622 for the visible (white) light that project the visible (white) light image into the image plane at the one or more image sensors in the camera sensor and/or for the demagnified, spectrally separated fluorescence light. The projection optics 622 may include, for example, any suitable combination of lenses, mirrors, filters, or other optical components suitable for projecting the light onto the one or more image sensors.

Figure 16A:
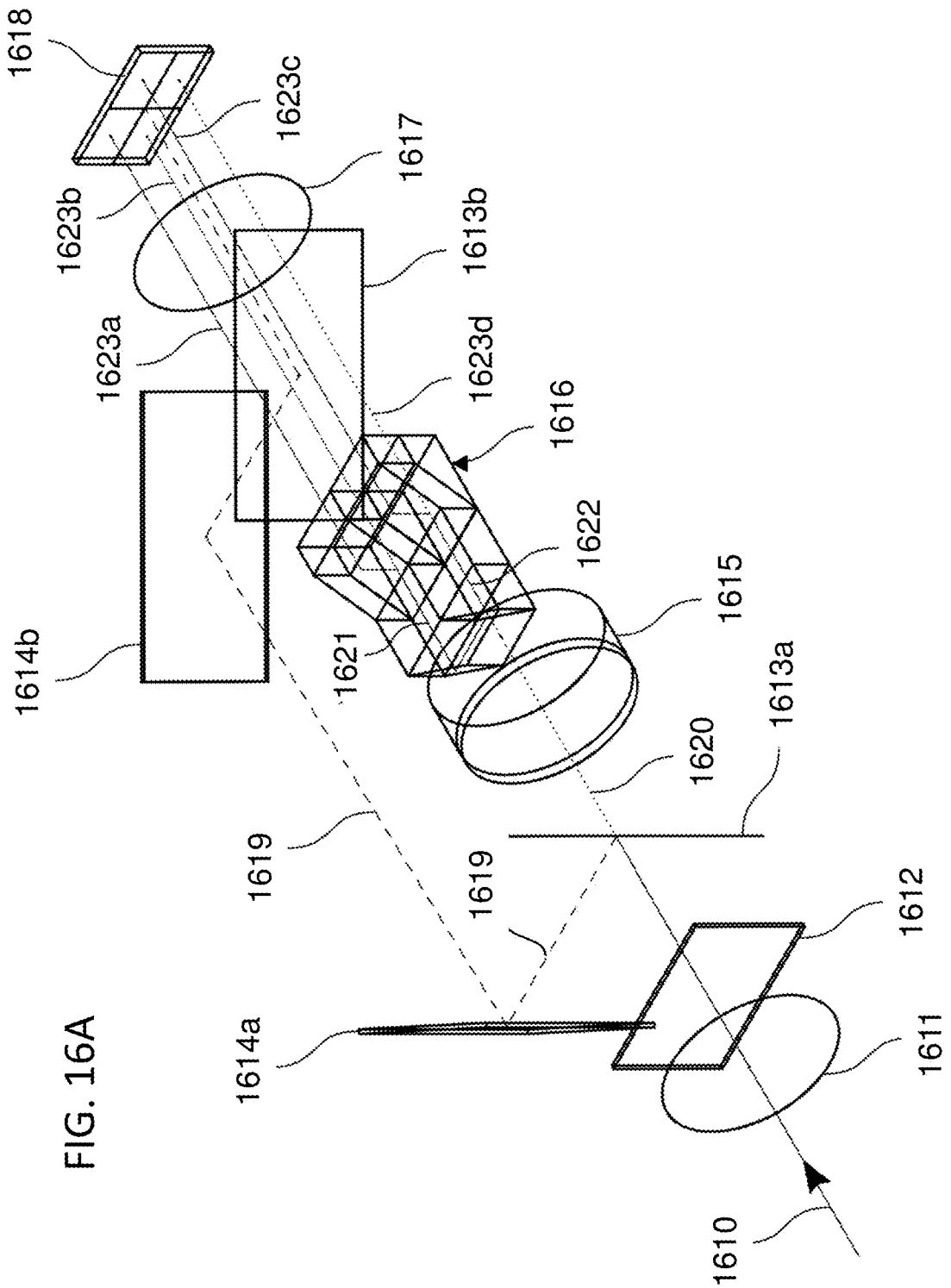
FIGS. 16A-16C are perspective, top, and right-side views of a schematic of another variation of an exemplary optical assembly in a fluorescence imaging system.
Figures 16B, 16C:
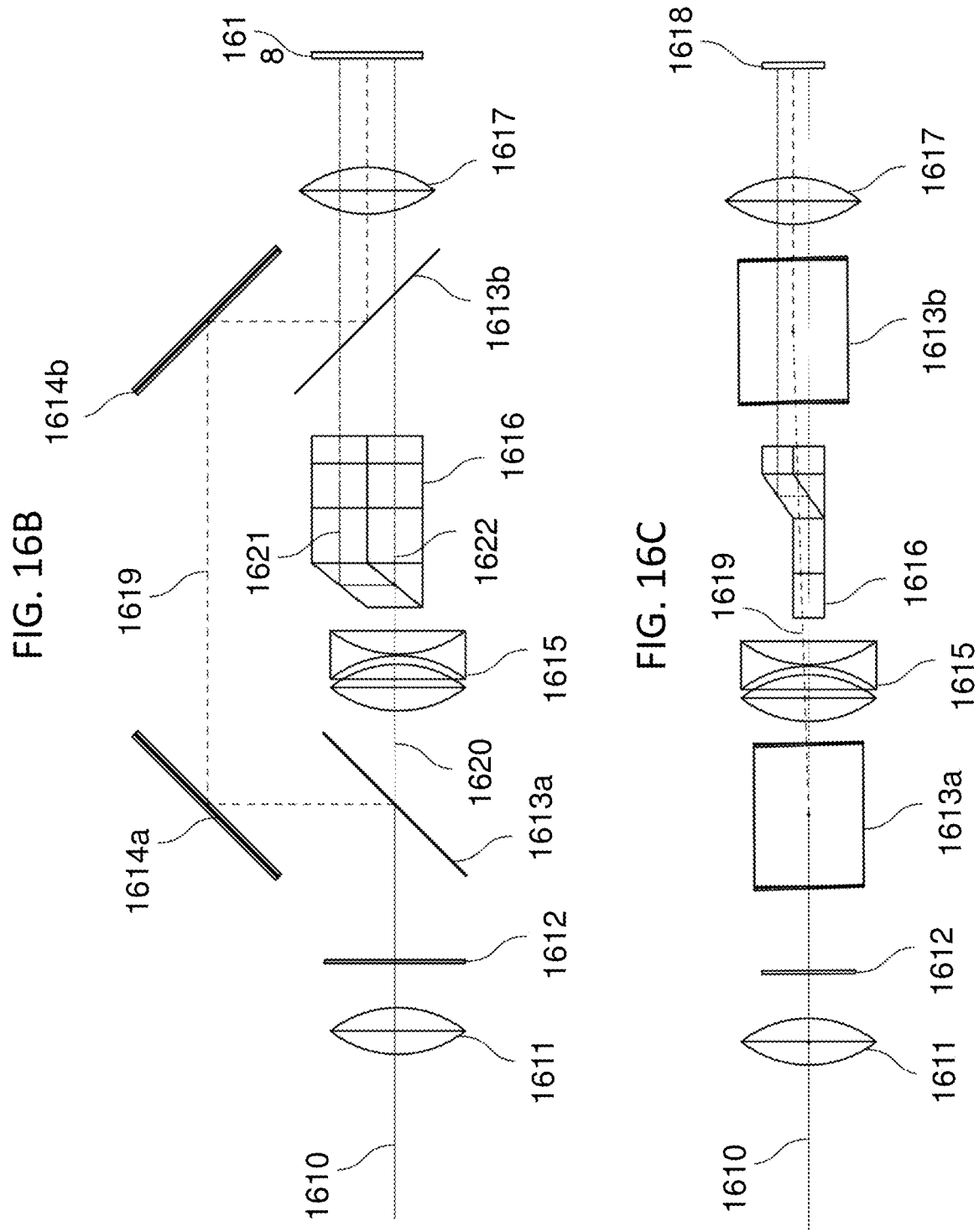

In another variation as shown in FIGS. 16A-16C, the optical assembly may be similar to that depicted in FIGS. 6A-6B except described below. In particular, incident light 1610 (e.g., excitation light, visible light, emitted fluorescence light, etc.) passes through field lens 1611 or other input optics, and then through fluorescence excitation light blocking filter 1612 that prevents passage of fluorescence excitation light. In contrast to the dichroic splitter 612 shown in FIGS. 6A and 6B, dichroic splitter 1613a transmits fluorescence light 1620 and reflects visible light 1619, thereby diverting the visible light to a different path (e.g., one that is offset from the optical axis of the image sensor). The fluorescence light branch 1620 transmitted by the dichroic splitter 1613a continues into demagnification optics 1615 and beam splitter assembly 1616 which spectrally divides the demagnified fluorescence light into four branches 1623a, 1623b, 1623c, and 1623d. The visible light branch 1619 reflected by the dichroic splitter 1613a may be diverted by components such as mirror 1614a to maintain substantially equal optical path length for the visible and fluorescence light paths. An alignment component system (e.g., mirror 1614b and dichroic mirror 1613b) may fold the visible light branch 1619 into the same optical path as the four fluorescence branches such that the visible light and fluorescence light pass through projection optics 1617. Projection optics 1617 projects the visible (white) light image onto the center of the image plane at image sensor 1618 and projects the four fluorescence images onto four quadrants of the image plane at the image sensor. However, the alignment component system may cause the fluorescence images to be projected on any suitable portions of the image plane.

Although the above components are primarily described as arranged in a particular order in the optical path, the optical assembly components may be arranged such that the various beam splitting, demagnification, and alignment steps (or subset thereof) may occur in any suitable manner and combination. For example, in some variations, the beam splitter (#1) may further split the emitted fluorescence light into multiple branches (e.g., two, three, four, etc.) before the demagnification optics. For example, the beam splitter may divide the emitted fluorescence light such that each branch of fluorescent light corresponds to a respective excitation waveband (e.g., about 670 nm, about 770 nm, about 805 nm, etc.) that caused the fluorophores in the object to emit the fluorescent light. In these variations, the optical assembly may include multiple sets of demagnification optics, each of which may reduce the image size of a respective fluorescent optical branch. In these variations, the optical assembly may omit one or more beam splitters (#2) since no further division of the fluorescent light may be necessary following demagnification.

The camera of the fluorescence system may include an image sensor assembly for transducing the full color visible (white) light optical image and de-magnified fluorescence emission images projected onto the four quadrants of the sensor/sensor assembly. The image sensor assembly may have high definition or ultra-high definition spatial resolution (e.g., 4K or higher resolution). In some variations, as shown in FIG. 6A, the image sensor assembly may include a single sensor 640a (e.g., with a color filter array). In some variations, as shown in FIG. 6B, the image sensor assembly may include a three-sensor assembly 640b, which may be coupled to a Philips prism or other spectral splitting technology. In some variations, the camera may include an image sensor assembly similar to that described above in the fluorescence imaging system with a configurable platform. However, the camera may include any suitable kind of image sensor assembly.

In some variations, some or all of the optics regions for performing the various beam functions described above (e.g., projecting the reflected white light as a white light image onto the image sensor, reducing the image size of the fluorescence light, spectrally separating the fluorescence light, projecting the separated fluorescence light as fluorescence images onto different portions of the image sensor, etc.) may be combined in one or more prisms, in addition to or instead of separate components. The one or more prisms may be made of any suitable kind of optical glass or other suitable kind of material that transmits light.

Figure 7:
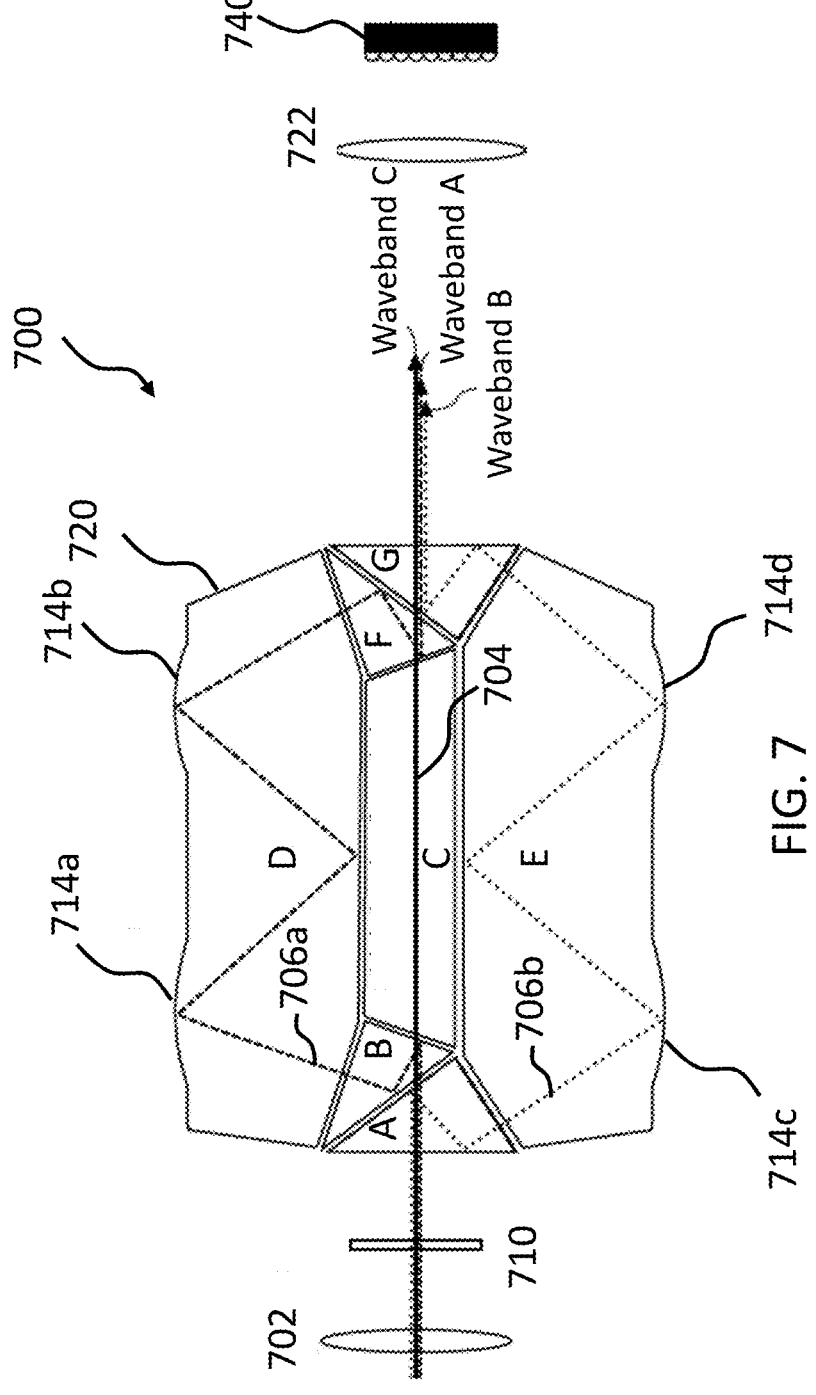
FIG. 7 is an illustrative depiction of another variation of an exemplary optical assembly in a fluorescence imaging system.

FIG. 7 illustrates one variation in which an optical assembly 700 includes a prism 720. Field lens 702 and fluorescence excitation light blocking filter 710 may be similar to field lens 602 and filter 610 described above with respect to FIGS. 6A-6B. Prism 720 may have facets or other structures that split the incoming light into at least two legs or branches: one branch 704 for reflected visible (white) light, a second branch 706a for fluorescence light of one emission waveband, and a third branch 706b for fluorescence light of another emission waveband. In particular, region A spectrally splits fluorescent light of Waveband A into branch 706a, region B spectrally splits fluorescent light of Waveband B into branch 706b, and white light of Waveband C passes into region C in branch 704.

Prism 720 may further include regions D and E, which define beam-shaping prism faces including demagnification optics (e.g., 714a, 714b, 714c, and 714d, etc.). In some variations, each concave or other suitable demagnifying prism face may demagnify by a factor of about the square root of 2, such that in order to reduce the dimensions of a fluorescence image by an overall factor of 2, the fluorescence image may interact with two beam-shaping prism faces (e.g., branch 706a is shaped by prism faces 714a and 714b, while branch 706b is shaped by prism faces 714c and 714d). However, the fluorescent light may interact with any suitable number of beam-shaping prism faces to achieve any suitable level of demagnification. Generally speaking, these demagnification optics may result in demagnified fluorescence emission images, similar to demagnification optics 614 described above with respect to FIGS. 6A-6B.

Prism 720 may further include regions F and G, which may fold the multiple fluorescence emission optical paths back into the visible light optical path prior to the image sensor(s) 740, similar to mirrors 620a and 620b described above with respect to FIGS. 6A-6B. The optical assembly may further include projection optics 722 and one or more image sensors 740, which may be similar to projection optics 622 and image sensor(s) 640a and/or 640b described above with respect to FIGS. 6A-6B.

The various regions A-G of prism 720 may have differing indices of refraction to compensate for differing travel distances for the white light branch 704 and the fluorescent light branches 706a and 706b. In other words, the differing indices of refraction may substantially equalize the travel time/optical path length for the white light branch 704 and the fluorescent light branches 706a and 706b. In particular, regions D and E may have a lower index of refraction than region C, such that light traveling through regions D and E will reach projection optics 722 and image sensor(s) 740 at the same time as light traveling through region C. However, the regions A-G of prism 720 may have any suitable combination of materials with varying index of refraction such that the white light branch 704 and fluorescent light branches 706a and 706b have about equal travel times. Furthermore, in other variations, the prism 720 may have additional or fewer regions corresponding to different numbers of excitation/emission wavebands of fluorescent light that will be separated, demagnified, and projected onto the image sensor (e.g., two additional regions similar to regions D and E, for shaping four separate paths of fluorescent light for four excitation/emission wavebands). Additionally, in some variations, prism 720 may comprise multiple prisms in combination.

Figure 8:
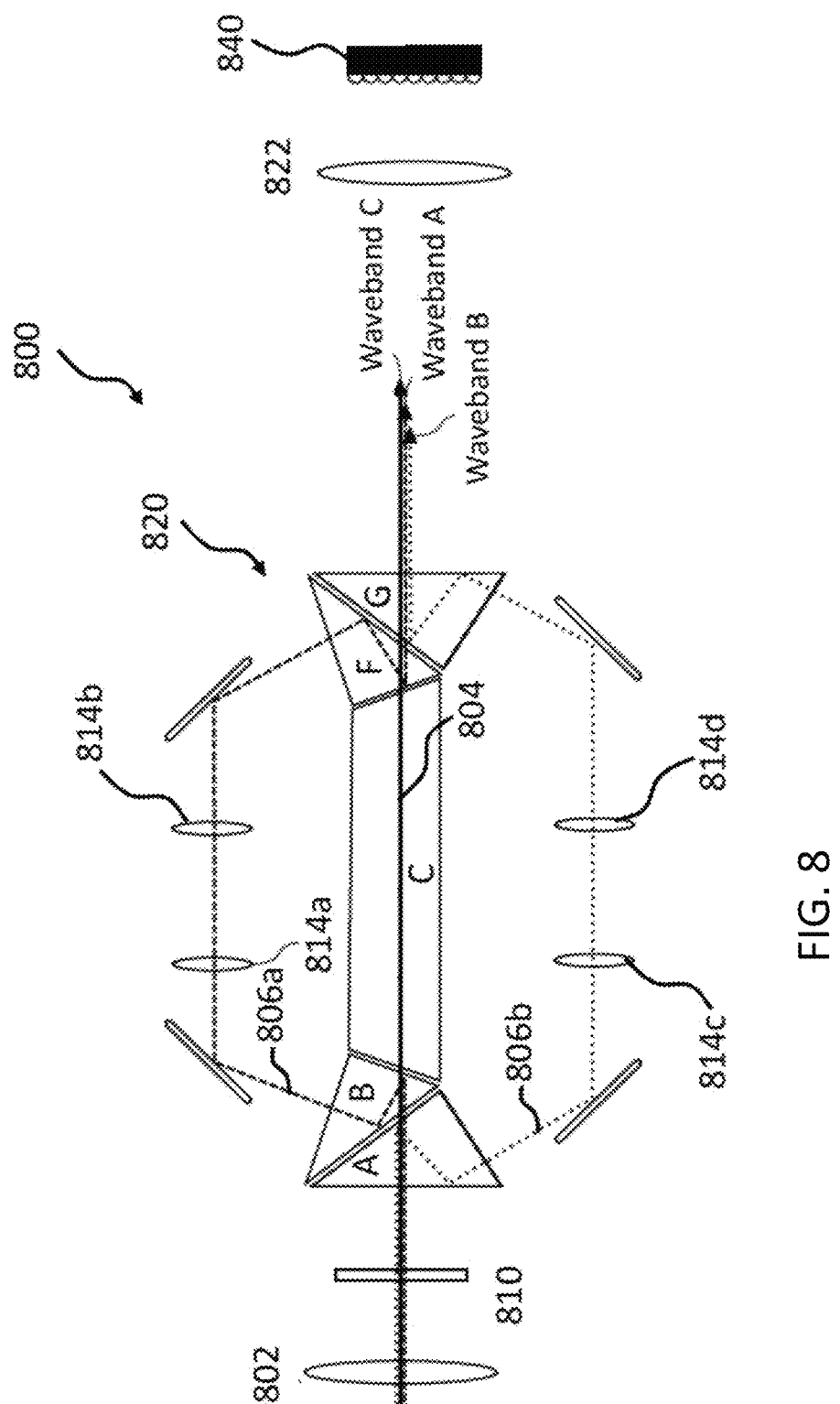
FIG. 8 is an illustrative depiction of another variation of an exemplary optical assembly in a fluorescence imaging system.

FIG. 8 illustrates another variation of an optical assembly 800 which is similar to optical assembly 700 depicted in FIG. 7 and described above, with at least the following differences where noted below. Field lens 802, filter 810, projection optics 822, and image sensor(s) 840 may be similar to field lens 702, filter 710, projection optics 722, and image sensor(s) 740 described above with respect to FIG. 7, respectively. Furthermore, prism 820 may include regions A, B, C, F, and G similar to the corresponding regions in prism 720. However, prism 820 may omit regions D and E in prism 720 (and omit demagnification optics regions 714a, 714b, 714c, and 714d), and instead prism 820 may include other separate demagnification optics (e.g., 814a, 814b, 814c, and 814d) to demagnify the image sizes of fluorescent light in branches 806a and 806b. Similar to the prism 720, region C of prism 820 may have a higher index of refraction to equalize the travel time/optical path length for the white light branch 804 and fluorescent light branches 806a and 806b.

Yet other variations of the optical assembly may include any suitable combination of the variations shown in FIGS. 6A, 6B, 7, 8, and/or 16A-16B, and/or may include additional optics to separate the fluorescent light into more than the three branches described in the above examples.

Controller and Image Processor

As shown in FIG. 5, the multiplexed fluorescence imaging system 500 may include a controller 560 and an image processor 550. The controller 560 may control the light source assembly 510 such that either the white light provider 512, or fluorescence excitation light provider 514, or both, are strobed at a high frequency (e.g., 60 Hz or greater), preferably in synchronous operation with the image acquisition by the camera. The white light and the excitation light may be pulsed at the same or different frequencies. The camera may have an appropriately matching sensor read-out frequency and acquire either separate white light and fluorescence emission images, and/or a known combination of visible light and fluorescence emission images which can be separated by further image processing (e.g., by comparing image frames with strobed illumination/excitation light on and off). The high speed strobing of the illumination and read-out of the camera sensors may enable the fluorescence emission and full color white light image data to be simultaneously displayed in real time.

The image processor 550 may receive the transduced image signals from the camera and process them into white light and fluorescence images. In particular, the image processor may electronically magnify the fluorescence images to restore their image size to about their original size before demagnification. The electronic magnification may cause the image size of the fluorescence images to be about the same size as the white light image. In some variations, the image processor may spatially co-register the magnified fluorescence images with the white light image.

Display and Other Data Components

As shown in FIG. 5, in some variations, the multiplexed fluorescence imaging system may include one or more data components 570 such as a display, recorder, or other data storage device, printer, and/or PACS similar to the data modules described above with respect to the fluorescence imaging system with configurable platform. The multiplexed fluorescence imaging system may additionally or alternatively include any other suitable systems for communicating and/or storing image data.

In some variations, the white light images and/or fluorescence images may be displayed on a high definition or ultra-high definition display (e.g., on a monitor having 4K or higher spatial resolution). The fluorescence images may be displayed in one or more of multiple manners. The manner in which the fluorescence images are displayed may be selected by an operator in a user interface. In one variation, the fluorescence images can be individually displayed as monochrome images. In another variation, the chroma of each of the fluorescence images can be mapped to different contrasting color for each fluorescence emission, where the mapped color is chosen to be one that is not likely to occur naturally in the body (e.g., green, purple, etc.). The fluorescence images can then be individually or collectively combined with the full color, visible (white) light image for display. In another variation, the intensity of the fluorescence signal in a fluorescence image can be normalized by scaling the brightness (luma) of each of the fluorescence images with the co-registered reflected red light image signal (i.e., the red portion of the full visible (white) light image), and then displayed with a color map selected to emphasize specific ranges of fluorescence intensity.

Similarly, in some variations, one or more of the other data components (e.g., data storage module or recorder, printer, PACS, etc.) can communicate and/or store the white light images and the fluorescence images as they appear in any of the above-described manners.

Method for Fluorescence Imaging an Object

A method for fluorescence imaging an object may include emitting white light, emitting excitation light in a plurality of excitation wavebands, causing the object to emit fluorescent light, receiving reflected white light and emitted fluorescent light from the object on an at least one image sensor, and feeding at least part of the reflected light through an optical assembly located in an optical path between the object and the image sensor. The method may include projecting reflected white light as a white light image onto the image sensor. The method may include reducing the image size of the fluorescent light, spectrally separating the fluorescent light, and projecting the separated fluorescent light as fluorescence images onto different portions of the image sensor. In some variations, the method includes electronically magnifying (e.g., with an image processor) at least some of the fluorescence images. In some embodiments, excitation light is emitted in a plurality of non-overlapping excitation wavebands.

A kit may include any part of the systems described herein (including components of variations of the fluorescence imaging system with a configurable platform, components of variations of the multiplexed fluorescence imaging system, or combinations of components thereof) and a fluorescence imaging agent such as, for example, a fluorescence dye such as ICG or any suitable fluorescence imaging agent. The kit may include instructions for use of at least some of its components (e.g., for using the fluorescence imaging agent, operating the fluorescence imaging system, maintaining the fluorescence imaging system, etc). In yet further aspects, there is provided a fluorescence imaging agent such as, for example, a fluorescence dye, for use in the systems and methods described herein.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description, features are described herein as part of the same or separate embodiments, however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:

1. A system for fluorescence imaging of an object, comprising:

an image sensor assembly comprising at least one image sensor; and an illuminator configured to emit excitation light in a plurality of excitation wavebands for causing the object to emit fluorescence light, wherein the plurality of excitation wavebands comprises a plurality of visible light wavebands, the illuminator comprising:

at least one first fluorescence excitation light emitter configured to emit fluorescence excitation light having a first waveband of the plurality of visible light wavebands, at least one second fluorescence excitation light emitter configured to emit fluorescence excitation light having a second waveband of the plurality of visible light wavebands, the second waveband being different than the first waveband, wherein the illuminator is configured to activate the at least one first fluorescence excitation light emitter independently of the at least one second fluorescence excitation light emitter, and at least one imaging light emitter configured to emit imaging light for reflected light imaging of the object; and an optical assembly configured to transmit imaging light reflected from the object and fluorescence light emitted from the object to the image sensor assembly, the optical assembly comprising at least one notch filter configured to block light in the plurality of fluorescence excitation wavebands while transmitting the fluorescence light and imaging light reflected from the object that is not in the plurality of fluorescence excitation wavebands, wherein the optical assembly is configured to project the fluorescence light and the imaging light reflected from the object that is not in the plurality of fluorescence excitation wavebands onto the at least one image sensor of the image sensor assembly, wherein at least a portion of the fluorescence light and at least a portion of the imaging light reflected from the object that is not in the plurality of fluorescence excitation wavebands are projected onto the same image sensor of the image sensor assembly.

2. The system of claim 1, wherein the at least one notch filter comprises a single multi-band notch filter configured to block the light in the plurality of fluorescence excitation wavebands.

3. The system of claim 1, wherein the plurality of fluorescence excitation wavebands are non-overlapping.

4. The system of claim 1, wherein the at least one notch filter comprises a plurality of single-notch blocking filters placed in series, each single-notch blocking filter configured to block light in a selected waveband of the plurality of fluorescence excitation wavebands.

5. The system of claim 1, wherein the plurality of fluorescence excitation wavebands comprises one or more of an ultraviolet (UV) waveband and a near-infrared (NIR) waveband.

6. The system of claim 1, wherein the plurality of fluorescence excitation wavebands comprises one or more of: 405 nm, 470-480 nm, 660 nm, 760-780 nm, and 750-810 nm.

7. The system of claim 1, wherein the at least one notch filter has an optical density of 4-6.

8. The system of claim 1, wherein the at least one notch filter has a transmission rate of at least 90% in transmitting light in at least one waveband other than the plurality of fluorescence excitation wavebands.

9. The system of claim 8, wherein the at least waveband other than the plurality of fluorescence excitation wavebands comprises at least a portion of a visible light spectrum.

10. The system of claim 2, wherein the at least one notch filter has a transition width of less than 10 nm between a transmitted portion and a blocked portion of a light spectrum.

11. The system of claim 1, wherein the at least one notch filter comprises at least one substrate comprising one or more dielectric coatings configured to block light in at least one waveband of the plurality of fluorescence excitation wavebands.

12. The system of claim 11, wherein the at least one substrate comprises a glass substrate.

13. The system of claim 12, wherein the at least one notch filter comprises a multi-band notch filter that comprises a plurality of dielectric coatings with alternating high and low refractive indexes on the glass substrate.

14. The system of claim 11, wherein the at least one notch filter comprises a plurality of single-notch blocking filters, each single-notch blocking filter comprising a different dielectric coating configured to block a selected waveband of the plurality of fluorescence excitation wavebands.

15. The system of claim 1, wherein the optical assembly is configured to project a plurality of fluorescence images onto the at least one image sensor, each fluorescence image projected onto a different portion of the at least one image sensor.

16. The system of claim 1, wherein the at least one notch filter is located in a portion of an optical imaging path between the object and the image sensor assembly in which light rays of the fluorescence light emitted by the object have a minimum cone angle.

17. The system of claim 1, wherein the optical assembly is configured to reduce an image size of the fluorescence light, spectrally separate the fluorescence light, and project the spectrally separated fluorescence light onto the at least one image sensor.

18. The system of claim 1, wherein the imaging light reflected from the object that is not in the plurality of fluorescence excitation wavebands comprises white light.

19. The system of claim 18, wherein, the optical assembly is configured to project the transmitted white light as a white light image onto the at least one image sensor of the image sensor assembly.

20. The system of claim 1 wherein the illuminator is configured to generate white light simultaneously with at least one of the plurality of fluorescence excitation wavebands.

21. The system of claim 1, comprising a surgery-specific component configured to direct the light in the plurality of fluorescence excitation wavebands to the object and to receive the light emitted from the object.

22. The system of claim 21, wherein the surgery-specific component is an interchangeable component comprising a surgical microscope, a laparoscope, an endoscope, an open field illumination and imaging module, a stereoscopic videoscope, or a scintigraphy module.

23. The system of claim 21, wherein at least one of the image sensor assembly and the optical assembly are integrated into the surgery-specific component.

24. The system of claim 1, comprising a controller configured to selectively control a fluorescence mode of the system.

25. The system of claim 1, comprising an image processor configured to generate a fluorescence emission image based on image signals received from the image sensor assembly and associated with the fluorescence light emitted from the object.

26. A method for fluorescence imaging, comprising:

generating, by at least one first fluorescence excitation light emitter of an illuminator of an imaging system, light in a first excitation waveband to cause a first fluorescence light emission from a first target, wherein the first excitation waveband is a first visible light waveband;

blocking, by at least one notch filter of the imaging system, the light in the first excitation waveband while transmitting the first fluorescence light emission to at least one image sensor of the imaging system;

generating, by at least one second fluorescence excitation light emitter of the illuminator, light in a second excitation waveband to cause a second fluorescence light emission from a second target, wherein the second excitation waveband is a second visible light waveband, the second waveband being different than the first waveband, and wherein activation of the at least one second fluorescence excitation light emitter is independent of activation of the at least one first fluorescence excitation light emitter;

blocking, by the at least one notch filter of the imaging system, the light in the second excitation waveband while transmitting the second fluorescence light emission to the at least one image sensor of the imaging system;

generating, by an imaging light emitter of the illuminator, imaging light that reflects from the first target; and transmitting, by the at least one notch filter of the imaging system, the imaging light reflected from the first target that is not in the first excitation waveband or in the second excitation waveband onto the at least one sensor of the imaging system, wherein at least a portion of the first fluorescence light emission and at least a portion of the imaging light reflected from the first target that is not in the first excitation waveband or in the second excitation waveband are projected onto the same image sensor of the imaging system.

27. The method of claim 26, comprising switching a fluorescence mode of the illuminator to cause the illuminator to switch from generating the light in the first excitation waveband to generating the light in the second excitation waveband.

28. The method of claim 26, wherein the at least one notch filter comprises a single multi-band notch filter.

29. The method of claim 26, wherein the first excitation waveband and the second excitation waveband are non-overlapping.

30. The method of claim 26, wherein the at least one notch filter comprises a plurality of single-notch blocking filters positioned in series.

31. The method of claim 26, comprising transmitting white light by the at least one notch filter.

* * * * *